United States Patent
Patel et al.

(10) Patent No.: US 12,031,135 B2
(45) Date of Patent: Jul. 9, 2024

(54) p63 INACTIVATION FOR THE TREATMENT OF HEART FAILURE

(71) Applicant: Baylor College of Medicine, Houston, TX (US)

(72) Inventors: Vivekkumar B. Patel, Houston, TX (US); Hongran Wang, Houston, TX (US); Vivek P. Singh, Houston, TX (US); Erin Lynn Reineke, Houston, TX (US); Megumi Mathison, Houston, TX (US); Austin J. Cooney, Houston, TX (US); Todd Rosengart, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 0 days.

(21) Appl. No.: 17/813,493

(22) Filed: Jul. 19, 2022

(65) Prior Publication Data

US 2022/0348921 A1  Nov. 3, 2022

Related U.S. Application Data

(63) Continuation of application No. 15/552,253, filed as application No. PCT/US2016/018735 on Feb. 19, 2016, now Pat. No. 11,421,229.

(Continued)

(51) Int. Cl.
*C12N 15/86* (2006.01)
*A61K 9/00* (2006.01)
(Continued)

(52) U.S. Cl.
CPC .......... *C12N 15/113* (2013.01); *A61K 9/0019* (2013.01); *A61K 31/47* (2013.01);
(Continued)

(58) Field of Classification Search
CPC .. C12N 15/113; C12N 15/1135; C12N 15/86; C12N 5/0657; C12N 2320/31; C12N 2501/60; A61K 31/713; A61K 48/0058
See application file for complete search history.

(56) References Cited

U.S. PATENT DOCUMENTS

2007/0044164 A1  2/2007  Dickins et al.
2010/0093090 A1  4/2010  Deng et al.
(Continued)

FOREIGN PATENT DOCUMENTS

EP  1693451 A1  8/2006
WO  2009073618 A2  6/2009
(Continued)

OTHER PUBLICATIONS

Alexandrov et al., "DNp63 regulates select routes of reprogramming via multiple mechanisms", Cell Death and Differentiation (2013) 20, 1698-1708.

(Continued)

*Primary Examiner* — Terra C Gibbs
(74) *Attorney, Agent, or Firm* — Norton Rose Fulbright US LLP

(57) ABSTRACT

Embodiments of the disclosure include methods and compositions for in situ cardiac cell regeneration, including transdifferentiation of cardiac cells to cardiomyocytes. In particular embodiments, in situ cardiac cell regeneration encompasses delivery of p63 shRNA and one or both of Hand2 and myocardin, and in specific embodiments further includes one or more of Gata4, Mef2c, and Tbx5. In specific aspects of the disclosure, adult cardiac fibroblasts are reprogrammed into cardiomyocytes using viral vectors that harbor p63 shRNA and one or both of the transcription factors Hand2 and myocardin.

18 Claims, 31 Drawing Sheets

Methods: Experiment #1

Day 1 - Cells seeded
Day 0 - Infection
Day 2 - Media changed
Day 20 – FACS

Cells:
 Mouse embryonic fibroblasts
 wild type, p63-/-
 H92c rat neonatal cardiomyoblasts

Factors:
 Rat lentivirus GMT
 Rat lentivirus GFP

Reprogramming media: IMDM + Glutamax, Medium 199, 10% fetal bovine serum, 1% non-essential amino acids, 1% antibiotic

Antibodies:
 Primary – ABCAM mouse mAb to cTnT (ABCAM, ab8295)
 Secondary – Goat pAb to MsAb IgG (ABCAM, Alexa Fluor 647, ab150115)

Related U.S. Application Data

(60) Provisional application No. 62/118,573, filed on Feb. 20, 2015.

(51) Int. Cl.

| | | |
|---|---|---|
| *A61K 31/47* | (2006.01) | |
| *A61K 31/713* | (2006.01) | |
| *A61K 38/17* | (2006.01) | |
| *A61K 48/00* | (2006.01) | |
| *C07K 14/47* | (2006.01) | |
| *C07K 14/82* | (2006.01) | |
| *C12N 5/077* | (2010.01) | |
| *C12N 15/113* | (2010.01) | |

(52) U.S. Cl.
CPC ........ *A61K 31/713* (2013.01); *A61K 38/1709* (2013.01); *A61K 48/0058* (2013.01); *C07K 14/4702* (2013.01); *C07K 14/4746* (2013.01); *C07K 14/82* (2013.01); *C12N 5/0657* (2013.01); *C12N 15/1135* (2013.01); *C12N 15/86* (2013.01); *C12N 2310/14* (2013.01); *C12N 2310/531* (2013.01); *C12N 2320/31* (2013.01); *C12N 2501/60* (2013.01); *C12N 2710/10043* (2013.01); *C12N 2740/15043* (2013.01)

(56) References Cited

U.S. PATENT DOCUMENTS

| | | |
|---|---|---|
| 2012/0076762 A1 | 3/2012 | Kawamura et al. |
| 2012/0128655 A1 | 5/2012 | Kim et al. |

FOREIGN PATENT DOCUMENTS

| | | |
|---|---|---|
| WO | 2010111422 A2 | 9/2010 |
| WO | 2011063039 A1 | 5/2011 |
| WO | 2011080261 A1 | 7/2011 |
| WO | 2011139688 A2 | 11/2011 |
| WO | 2014071199 A1 | 5/2014 |
| WO | 2014093051 A2 | 6/2014 |

OTHER PUBLICATIONS

Budinatzky, Inbar et al; "Concise Review: Reprograming Strategies for Cardiovascular Regenerative Medicine: From Induced Pluriopotent Stems Cells to Direct Reprograming"; Stem Cells Transtational Medicine; 2014;3:448-457.
Candi et al., "MicroRNAs and p63 in epithelial stemness", Cell Death and Differentiation (2015) 22, 12-21.
Chakravarti et al., "Induced multipotency in adult keratinocytes through down-regulation of DNp63 or DGCR8", PNAS, Published online Jan. 21, 2014, E572-E581.
Dotsch et al. (Cold Spring Harb Perspect Biol., 2010 vol. 2: 1-14).
Efe, Jem A. et al; "Conversion of Mouse Fibroblasts into Cardiomyocytes using a Direct Reprogramming Strategy"; Nature Cell Biology, Vo. 13, No. 3, Mar. 211.
Leda, Masaki, et al; "Direct Reprogramming of Fibroblasts into Functional Cardiomyocytes by Defined Factors": Cell 142, Aug. 6, 2020; 375-386.
Lee et al. (Molecular Therapy, 2013 vol. 21: 1767-1777).
Liu, Zhiqiang et al: "Current Status of Induced Pluripotent Stem Cells in Cardiac Tissue Regeneration and Engineering": Regenerative Medicine Research—BioMed Central; 2013.
Nam et al. (PNAS, 2013 Vol. 110:5588-5593, plus Supporting Information).
Rouleau et al., "TAp63 Is Important for Cardiac Differentiation of Embryonic Stem Cells and Heart Development", Stem Cells, vol. 29, Issue 11, Sep. 2, 2011.
Skalova, Stepanka et al; "Induced Pluripotent stem Cells and Their Use in Cardiac and Neural Regeneratie Medicine" International Journal of Molecular Sciences; 2015; 16, 4043-4067.
Song, Kunhua, et al; "Heart Repair by Reprogramming Non-Mycoytes with Cardiac Transcription Factors"; HHS Public Access; Nature: 485 (7400): 599-604; Nov. 2012.
Srivastava, Deepak, et al; "Cardiac Repair with Thymosin β4 and Cardiac Reprogramming Factors"; Annals of the New York Academy of Sciences; 1270(2012) 66-72.
Willems et al. (Cell Stem Cell, 2012 vol. 11 :242-252).

Methods: p63 shRNA

- p63 lentivirus shRNA was used to infect MEFs
- Puromycin selection performed for 5-7 days
- Knockdown efficiency measured at 7 days
- Induction of pro-cardiogenic markers seen at 3 weeks after addition of cardiac reprogramming media

FIG. 27 p63 INACTIVATION FOR THE TREATMENT OF HEART FAILURE

This application is a continuation of U.S. patent application Ser. No. 15/552,253 filed Aug. 18, 2017 which is a national phase application under 35 U.S.C. § 371 that claims priority to International Application No. PCT/US2016/018735 filed Feb. 19, 2016 which claims the benefit of priority to U.S. Provisional Patent Application Ser. No. 62/118,573, filed Feb. 20, 2015, all of which are incorporated by reference herein in their entirety.

STATEMENT REGARDING FEDERALLY SPONSORED RESEARCH OR DEVELOPMENT

This invention was made with government support under HL121294 awarded by the National Institutes of Health. The government has certain rights in the invention.

TECHNICAL FIELD

Embodiments of the disclosure include at least the fields of molecular biology, cell biology, cell therapy, and medicine, including cardiac medicine.

BACKGROUND OF THE INVENTION

Despite medical and surgical innovations, heart disease remains the number one cause of death in the world. Given the poor regenerative capacity of the heart following myocardial infarction and the irreversible loss of cardiomyocytes, the replacement of cardiomyocytes by forming induced pluripotent stem cells or stimulating direct cellular reprogramming are potential therapeutic strategies that hold great promise. Both technologies are rooted in the idea that endogenous fibroblasts within the infarcted myocardium can be reprogrammed into functional cardiomyocytes. Several institutions have reported that a cocktail of transcription factors, most notably Gata4, Mef2c, and Tbx5, can be used to reprogram fibroblasts into cardiomyocytes in vitro. Nevertheless, the major obstacle in the implementation of this therapy is the low efficiency of reprogramming.

The present disclosure provides solutions to a long-felt need in the art for efficient and effective repair of cardiac tissue.

BRIEF SUMMARY OF THE INVENTION

Embodiments of the disclosure include methods and compositions for the treatment of any medical condition related to the mammalian heart. In specific embodiments, the disclosure concerns treatment of one or more cardiac medical conditions with therapeutic compositions that affect endogenous cells or tissue in the heart. In particular embodiments, therapy is provided to an individual in need thereof, such as when the individual has a need for in situ or in vivo therapy of endogenous cardiac tissue because of a cardiac medical condition or risk thereof. In specific embodiments, the individual has cardiac cellular or cardiac tissue damage from a cardiac medical condition.

In particular embodiments, delivery of certain composition(s) to cells in situ or in vivo in the individual allows regeneration of cardiomyocytes by allowing reprogramming of endogenous non-cardiomyocyte cells to become cardiomyocytes. Upon delivery of a therapeutically effective amount of one or more composition(s) to the individual, the composition(s) provide improvement of the condition at least in part, such as by allowing regeneration of cardiac tissue or cells therein. In specific embodiments, the composition(s) comprise one or more molecules for inactivation of p63, p53, p21, p16, p19, p38, and/or p57 (such as by at least one kind of RNA interference), or other factors the downregulation of which would enhance the reprogrammability or "plasticity of target cells. In certain embodiments, an individual may also be provided with one or more cardiac cell reprogramming factors (which may or may not be transcription factors). In particular embodiments, the composition(s) comprise Hand2, myocardin, or both. In specific embodiments, the RNA interference molecule for p63 inactivation comprises small interfering RNA (siRNA), short hairpin RNA (shRNA) or bi-functional shRNA, as examples. In certain embodiments, an individual is also provided with one or more chromatin destabilizing agents.

In particular embodiments of the disclosure, p63, p53, and/or p21 inactivation increases the transdifferentiation efficiency of cardiac cells (such as fibroblasts) into cardiomyocytes. As described herein, the partial or complete inactivation of the p63, p53, and/or p21 genes is a novel therapeutic intervention that allows the reprogramming of fibroblasts (for example) into cardiomyocytes at a much higher efficiency. In vitro studies confirm that 45% of p63 knockout mouse embryonic fibroblasts express cardiac Troponin T (cTnT), which is a highly specific marker for the cardiomyocyte lineage. p63 inactivation through shRNA or siRNA (for example) is a unique intervention that is a clinically relevant therapy for the treatment of any cardiac medical condition, including heart failure.

In specific embodiments, any p63, p53, and/or p21-inactivation agent and/or one or more cardiac cell reprogramming factors and/or one or more chromatin destabilizing agents and/or one or more anti-fibrotic agents and/or one or more angiogenic factors act synergistically with each other.

In specific embodiments, an individual in need thereof receives one or more anti-fibrotic agents, such as one or more anti-Snail agents (for example, siRNA, antibody, small molecule such as ITD-1, etc.).

in one embodiment, there is a method of in vivo reprogramming of cardiac cells, comprising the step of providing a therapeutically effective amount of one or more compositions to the heart of an individual, wherein said one or more compositions comprises an agent that partially or completely downregulates or inactivates p63, p53, and/or p21. In particular embodiments, the agent partially or completely downregulates or inactivates expression of p63, p53, and/or p21. In specific embodiments, the agent comprises p63 shRNA or siRNA, p53 shRNA or siRNA, or p21 shRNA or siRNA, respectively. Any isoform of p63 may be partially or completely downregulated or inactivated, including TA, for example.

In embodiments of the disclosure, methods comprise the step of providing to the individual an effective amount of one or more cardiac cell reprogramming factors, which may be a polypeptide, peptide, nucleic acid or mixture thereof. In specific embodiments, the one or more cardiac cell reprogramming factors is Hand2, myocardin, Gata4, Mef2c, Tbx5, Mesoderm posterior protein 1 (Mesp1), miR-133, miR-1, Oct4, Klf4, c-myc, Sox2, Brachyury, Nkx2.5, ETS2, ESRRG, Mrtf-A, MyoD, ZFPM2, miR-590, miR-208, miR-499, or a combination thereof. In certain embodiments, the one or more cardiac cell reprogramming factors is one or both of Hand2 and myocardin nucleic acids or polypeptides. In some cases, the one or both of Hand2 and myocardin nucleic acids or polypeptides are in the same or different composition as the agent that partially or completely downregulates or inactivates p63, p53, and/or p21. In specific embodiments, the one or more compositions comprise the nucleic acids of p63 shRNA and Hand2, the nucleic acids of p63 shRNA and myocardin, and/or the nucleic acids of p63 shRNA, Hand2, and myocardin.

In certain embodiments, the agent that partially or completely downregulates or inactivates p63, p53, and/or p21 is provided before the one or more cardiac cell reprogramming factors. In particular embodiments of the method, an effective amount of one or more chromatin destabilizing agents are provided to the individual. In particular embodiments, the one or more chromatin destabilizing agents are provided to the individual prior to when the agent that partially or completely downregulates or inactivates p63, p53, and/or p21 is provided to the individual. In some embodiments, the one or more chromatin destabilizing agents are provided to the individual prior to when the agent that partially or completely downregulates or inactivates p63, p53, and/or p21 is provided to the individual, and wherein the agent that partially or completely downregulates or inactivates p63, p53, and/or p21 is provided to the individual prior to when the one or more cardiac cell reprogramming factors are provided to the individual.

In certain embodiments, the cardiac cells are fibroblasts, endothelial cells, myoblasts, progenitor cells, stem cells, myofibroblasts, or a combination thereof. The cardiac cell may be a dividing cell or a non-dividing cell.

In particular embodiments, the agent that partially or completely downregulates or inactivates p63, p53, and/or p21 comprises a nucleic acid and said nucleic acid is comprised on one or more vectors. One or more cardiac cell reprogramming factors may comprise a nucleic acid and the nucleic acid may be comprised on one or more vectors. In specific embodiments, one or more chromatin destabilizing agents comprise a nucleic acid and the nucleic acid is comprised on one or more vectors. In some embodiments, the nucleic acids are comprised on separate vectors or on the same vector. In certain cases, the vector is a viral vector or a non-viral vector, such as a nanoparticle, plasmid, liposome, or a combination thereof. In a specific embodiment, the viral vector is an adenoviral, lentiviral, retroviral, adeno-associated viral vector, or episomal (non-integrating) vectors. In particular embodiments, p63 shRNA, Hand2, and/or myocardin nucleic acids are comprised on a lentiviral vector or are comprised on an adenoviral vector or are a modified mRNA molecule. In any vector encompassed by the disclosure, there may be a cell-specific promoter, such as a fibroblast-specific promoter.

In specific embodiments, any method encompassed by the disclosure comprises the step of delivering to the individual an additional cardiac therapy, such as one that comprises drug therapy, surgery, ventricular assist device (VAD) implantation, video assisted thoracotomy (VAT)coronary bypass, percutaneous coronary intervention (PCI), or a combination thereof.

Any of the compositions encompassed by the disclosure may be provided to the individual in a suitable delivery route, including systemic or local delivery. In specific embodiments, the delivery is local to the heart, and in specific embodiments, the providing step is further defined as injecting the compound(s) into the heart.

In one embodiment, there is a composition comprising one or more nucleic acid vectors, the vectors comprising one or more agents that partially or completely downregulates or inactivates p63, p53, and/or p21 and comprising one or more cardiac cell reprogramming factors. In some cases, the vector comprising one or more agents that partially or completely downregulates or inactivates p63, p53, and/or p21 is the same vector that comprises one or more cardiac cell reprogramming factors. In certain embodiments, the vector comprising one or more agents that partially or completely downregulates or inactivates p63, p53, and/or p21 is a different vector than the vector that comprises one or more cardiac cell reprogramming factors. In specific embodiments, a vector further compris one or more chromatin destabilizing agents. The vector that comprises one or more agents that partially or completely downregulates or inactivates p63, p53, and/or p21 may be the same vector that comprises one or more chromatin destabilizing agents. The vector that comprises one or more agents that partially or completely downregulates or inactivates p63, p53, and/or p21 and that comprises one or more cardiac cell reprogramming factors may be the same vector that comprises one or more chromatin destabilizing agents. The vector that comprises one or more agents that partially or completely downregulates or inactivates p63, p53, and/or p21 and that comprises one or more cardiac cell reprogramming factors may be a different vector that comprises one or more chromatin destabilizing agents. The composition that comprises a vector may comprise p63 shRNA and one or both of Hand 2 and myocardin nucleic acids. In certain embodiments, the composition that comprises a vector comprises p63 shRNA and Hand2 nucleic acids. In some embodiments, a composition that comprises a vector comprises p63 shRNA and myocardin nucleic acids or may comprise p63 shRNA, Hand2, and myocardin nucleic acids. In specific embodiments, any composition of the disclosure may comprise one or more anti-fibrotic agents.

In one embodiment there is a kit comprising a composition encompassed by the disclosure, said composition being housed in a suitable container.

The foregoing has outlined rather broadly the features and technical advantages of the present disclosure in order that the detailed description of the disclosure that follows may be better understood. Additional features and advantages of the disclosure will be described hereinafter which form the subject of the claims of the disclosure. It should be appreciated by those skilled in the art that the conception and specific embodiment disclosed may be readily utilized as a basis for modifying or designing other structures for carrying out the same purposes of the present disclosure. It should also be realized by those skilled in the art that such equivalent constructions do not depart from the spirit and scope of the disclosure as set forth in the appended claims. The novel features which are believed to be characteristic of the disclosure, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present disclosure.

BRIEF DESCRIPTION OF THE DRAWINGS

FIG. 27 illustrates an example protocol of how p63 can be knocked down using shRNA in mouse embryonic fibroblasts (MEFs) in vitro.

DETAILED DESCRIPTION OF THE INVENTION

Figure 1:
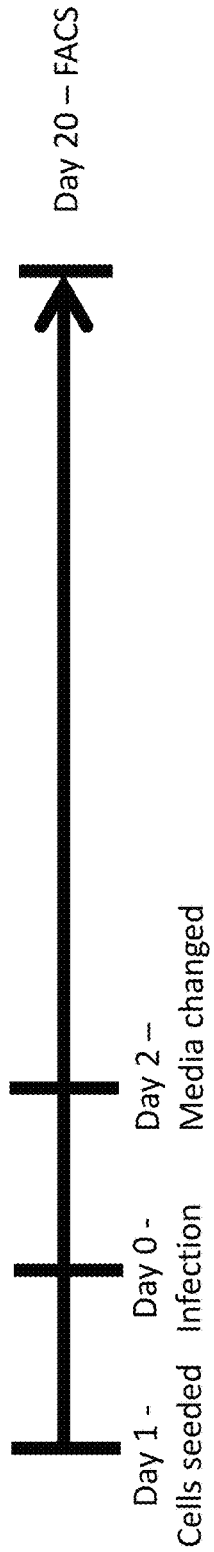
FIG. 1 shows an example of experimental design for analyzing fibroblast transdifferentiation into cardiomyocytes in vitro. GMT refers to the combination of Gata4, Mef2c, and Tbx5. GFP refer to green fluorescence protein. MEF(s) refers to mouse embryonic fibroblast(s). p63−/− indicates MEFs which have had the p63 gene deleted (Exons 6-8, DNA binding domain). Reprogramming efficiency was measured with Flow Cytometry for cardiac troponin T (cTnT) expression.

As used herein, the use of the word "a" or "an" when used in conjunction with the term "comprising" in the claims and/or the specification may mean "one," but it is also consistent with the meaning of "one or more," "at least one," and "one or more than one." Some embodiments of the disclosure may consist of or consist essentially of one or more elements, method steps, and/or methods of the disclosure. It is contemplated that any method or composition described herein can be implemented with respect to any other method or composition described herein.

The term "cardiac medical condition" as used herein refers to any medical condition that affects heart tissue, including that affects heart function.

The term "chromatin destabilizing agent" as used herein refers to one or more compounds that facilitate access of one or more factors to condensed genomic DNA.

The term "cardiac cell reprogramming factor" as used herein refers to one or more compositions that enhance or facilitate the transdifferentiation of a differentiated cell in the heart to a cardiomyocyte.

Embodiments of the disclosure include methods and compositions for the therapy or prevention of any cardiac medical condition in which it would be therapeutic to increase the number of cardiomyocytes in the heart. In specific embodiments, in vivo cells in the heart are reprogrammed to become cardiomyocytes. In particular embodiments, this is achieved at least in part by inactivating p63, p53, and/or p21, including at the nucleic acid level. In particular embodiments, nucleic acids and/or peptides and/or polypeptides are delivered directly to the heart to allow for reprogramming of non-cardiomyocyte cells in the heart to become cardiomyocytes.

I. Embodiments of Methods of Treatment

Embodiments of the present disclosure are directed to methods and/or compositions related to therapy and/or prevention of one or more cardiac-related medical conditions. Embodiments of the present disclosure concern regeneration of tissue, including muscle tissue, such as myocardial tissue, through the reprogramming of existing cells in the heart that are not cardiomyocytes. Certain embodiments relate to reversal of a cardiac medical condition (or improvement of at least one symptom thereof), including at least cardiac disease, cardiomyopathy, cardiotoxicity, congestive heart failure, ischemic heart disease, myocardial infarction, coronary artery disease, cor pulmonale, inflammatory heart disease; inflammatory cardiomegaly; myocarditis; congenital heart disease; rheumatic heart disease, cardiac systolic dysfunction, cardiac diastolic dysfunction, angina, dilated cardiomyopathy, idiopathic cardiomyopathy, or other conditions resulting in cardiac fibrosis, for example.

In particular aspects of the disclosure, cardiomyopathy is the cardiac medical condition to be treated. The cardiac medical condition (including, for example, cardiomyopathy) may be caused by one or more of a variety of characteristics, including, for example, long-term high blood pressure; heart valve problems; heart tissue damage (such as from one or more previous heart attack(s) or chronic or acute and/or recurrent episodes or sequelae of ischemic heart disease); chronic rapid heart rate; metabolic disorders, such as thyroid disease or diabetes; nutritional deficiencies of essential vitamins or minerals, such as thiamin (vitamin B-1), selenium, calcium and/or magnesium; pregnancy; alcohol abuse; drug abuse, including of narcotics or prescription drugs, such as cocaine or antidepressant medications, such as tricyclic antidepressants; use of some chemotherapy drugs to treat cancer (including Adriamycin); certain viral infections; hemochromatosis and/or an unknown cause or undetected cause, i.e. idiopathic cardiomyopathy.

In some cases, methods and compositions of the present disclosure are employed for treatment or prevention of one or more cardiac medical conditions or delay of onset of one or more cardiac medical conditions or reduction of extent of one or more symptoms of one or more cardiac medical conditions. In particular cases, such prevention, delay or onset, or reduction of extent of one or more symptoms, occurs in an individual that is at risk for a cardiac medical condition. Exemplary risk factors include one or more of the following: age, gender (male, although it occurs in females), high blood pressure, high serum cholesterol levels, tobacco smoking, excessive alcohol consumption, sugar consumption, family or personal history, obesity, lack of physical activity, psychosocial factors, diabetes mellitus, overweight, genetic predisposition, and/or exposure to air pollution.

Particular aspects of the disclosure concern delivery of at least one polynucleotide (including a gene), small molecule, peptide, polypeptide, shRNA polynucleotide, siRNA polynucleotide, and so forth to cardiac tissue for trans-differentiation of certain cells in the tissue. In specific embodiments, a nucleic acid is the active agent, whereas in some embodiments a polypeptide produced from the nucleic acid is the active agent. The tissue may be of any kind, but in specific cases it is cardiac muscle and/or scar tissue. In particular embodiments, methods and compositions of the disclosure allow for differentiation of adult resident cardiac progenitor cells and/or transdifferentiation of non-cardiomyocyte differentiated cells, such as fibroblast cells, into cardiac muscle cells.

Embodiments of the disclosure include delivery of one or more polynucleotides (which may also be referred to as nucleic acids) or polypeptides produced therefrom that stimulate transdifferentiation or direct reprogramming of cells (such as muscle cells, including cardiomyocytes) and/or tissue (including cardiac tissue). Particular aspects for such embodiments result in reversal of one or more cardiac medical conditions. Certain aspects for such embodiments result in improvement of at least one symptom of a cardiac medical condition. In exemplary embodiments, the cardiac medical condition is heart failure. The heart failure may be the result of one or more causes, including coronary artery disease and heart attack, high blood pressure, faulty heart valves, cardiomyopathy(such as caused by disease, infection, alcohol abuse and the toxic effect of drugs, such as cocaine or some drugs used for chemotherapy), idiopathic cardiomyopathy and/or genetic factors.

Particular but exemplary indications of embodiments of the disclosure include at least applications for 1) heart failure, including congestive heart failure; 2) prevention of ventricular remodeling; and/or 3) cardiomyopathy. Other indications may also include coronary artery disease, ischemic heart disease, valvular heart disease, etc. In specific embodiments, methods and compositions of the disclosure provide cardiomyocyte regeneration that is sufficient to reverse established cardiomyopathy, congestive heart failure, and prevention of ventricular remodeling.

In cases where the individual has cardiomyopathy, the cardiomyopathy may be ischemic or non-ischemic cardiomyopathy. The cardiomyopathy may be caused by long-term high blood pressure, heart valve problems, heart tissue damage from a previous heart attack, chronic rapid heart rate, metabolic disorders, nutritional deficiencies, pregnancy, alcohol abuse, drug abuse, chemotherapy drugs, viral infection, hemochromatosis, genetic condition, elevated cholesterol levels, or a combination thereof. Cardiomyopathy may also have no identified cause, i.e. idiopathic cardiomyopathy.

In certain embodiments, there is a method of regenerating cells at a desired location in an individual, comprising the steps of delivering to the location an effective amount of at least one molecule for p63, p53, and/or p21 inactivation. The inactivation of p63, p53, and/or p21 may be partial or complete. The at least one molecule for p63, p53, and/or p21 inactivation may be of any kind, such as p63 shRNA or siRNA, p53 shRNA or siRNA, and/or p21 shRNA or siRNA, respectively, with or without one or more cardiac cell reprogramming factor (such as Hand2 and/or myocardin, for example). In specific embodiments, the molecules are delivered in nucleic acid form, although in specific embodiments one or more of the compositions of the disclosure that are not directed to p63, p53, and/or p21 interference are polypeptides. In particular embodiments, the delivery location of the composition(s) is at a region of the heart. A delivering step may comprise injection directly into the heart, including directly into the area of damaged tissue; intravenous perfusion; intra-coronary artery myocardium perfusion; intra-artery organ perfusion by catheter; or coronary sinus perfusion catheter, for example.

Embodiments of the disclosure include methods and/or compositions for regeneration of cardiac muscle and reversal of myocardial ischemic injury, for example. In particular embodiments, there are methods for reprogramming of cardiac scar cells (fibroblasts) into adult cardiac muscle cells in mammalian hearts in an individual that has had a cardiac medical condition, such as acute or chronic ischemic injury, for example. In certain embodiments, such methods are achieved with compositions comprising at least p63 shRNA or siRNA, p53 shRNA or siRNA, and/or p21 shRNA or siRNA (as an example of RNA interference) and, in some cases, one or more cardiac cell reprogramming factors, such asHand2 and/or myocardin, for example.

Although in particular embodiments an individual is treated in an in vivo or in situ manner, in alternative embodiments the individual is treated with compositions encompassed by the disclosure in an ex vivo manner. In such embodiments, cells that are to be subjected to nucleic acid composition(s) of the disclosure are either obtained from the individual or are obtained from another individual. Such cells are subjected in vitro to the nucleic acid compositions such that they are uptaken by the cells, and the cells are then delivered to the individual to be treated.

In particular aspects, an individual is provided with an additional cardiac medical condition therapy.

II. p63, p53, and/or p21 Inactivation

In embodiments of the disclosure, the inactivation of p63, p53, and/or p21 is utilized for individuals with a cardiac medical condition to facilitate the reprogramming of endogenous cells in the heart to become cardiomyocytes, thereby regenerating cardiac tissue. The inactivation of p63, p53, and/or p21 may occur by any means, including at least by RNA interference in some manner, and in some cases with shRNA or siRNA. As such, the p63, p53, and/or p21 becomes partially or completely downregulated or inactivated by partial or complete knock down.

As used herein, the term "knock-down" or "knock-down technology" refers to a technique of gene silencing in which the expression of p63, p53, and/or p21 is reduced as compared to the gene expression prior to the introduction of the siRNA or shRNA, which can lead to the inhibition of production of the target gene product. The term "reduced" is used herein to indicate that the target gene expression is lowered by 0.1-100%. For example, the expression may be reduced by 0.5, 1, 5, 10, 15, 20, 25, 30, 35, 40, 45, 50, 55, 60, 65, 70, 75, 80, 85, 90, 95, or even 99%. The expression may be reduced by any amount (%) within those intervals, such as for example, 2-4, 11-14, 16-19, 21-24, 26-29, 31-34, 36-39, 41-44, 46-49, 51-54, 56-59, 61-64, 66-69, 71-74, 76-79, 81-84, 86-89, 91-94, 96, 97, 98 or 99. Knock-down of gene expression can be directed by the use of siRNAs or shRNAs.

As used herein, the terms "small interfering" or "short interfering RNA" or "siRNA" refer to an RNA duplex of nucleotides that is targeted to the p63, p53, and/or p21 gene, respectively, and is capable of inhibiting the expression of the p63 gene. The RNA duplex comprises two complementary single-stranded RNAs of 15, 16, 17, 18, 19, 20, 21, 22, 23, 24, or 25 nucleotides that form 15, 16, 17, 18, 19, 20, 21, 22, 23, 24, or 25 base pairs and possess 3' overhangs of two nucleotides. The RNA duplex is formed by the complementary pairing between two regions of a RNA molecule. siRNA is "targeted" to p63, p53, and/or p21 in that the nucleotide sequence of the duplex portion of the siRNA is complementary to a nucleotide sequence of p63, p53, and/or p21. In some embodiments, the length of the duplex of siRNAs is less than 30 nucleotides. The duplex can be 29, 28, 27, 26, 25, 24, 23, 22, 21, 20, 19, 18, 17, 16, 15, 14, 13, 12, 11 or 10 nucleotides in length. The length of the duplex can be 17-25 nucleotides in length. The duplex RNA can be expressed in a cell from a single construct.

As used herein, the term "shRNA" (small hairpin RNA) refers to an RNA duplex wherein a portion of the siRNA is part of a hairpin structure (shRNA). In addition to the duplex portion, the hairpin structure may contain a loop portion positioned between the two sequences that form the duplex. The loop can vary in length. In some embodiments the loop is 5, 6, 7, 8, 9, 10, 11, 12 or 13 nucleotides in length. The hairpin structure can also contain 3' or 5' overhang portions. In some aspects, the overhang is a 3' or a 5' overhang 0, 1, 2, 3, 4 or 5 nucleotides in length. In one aspect of this disclosure, a nucleotide sequence in the vector serves as a template for the expression of a small hairpin RNA, comprising a sense region, a loop region and an antisense region that targets p63, p53, and/or p21. Following expression, the sense and antisense regions form a duplex. It is this duplex, forming the shRNA, which hybridizes to, for example, the p63 mRNA and reduces expression of p63, p53, and/or p21. See Moore et al., Methods Mol Biol. 2010; 629: 141-158, for disclosure of shRNA design.

According to the disclosure, an siRNA or shRNA corresponding to a region of p63, p53, and/or p21 is expressed in the cell. The RNA duplex is substantially identical (typically at least about 80% identical, and more typically at least about 90% identical) in sequence to a region of p63, p53, and/or p21. siRNA duplexes are described and well known in the art. See, for example, U.S. Pat. No. 7,410,944.

In one embodiment, the shRNA is a "hairpin" or stem-loop RNA molecule, comprising a sense region, a loop region and an antisense region complementary to the sense region. In other embodiments the shRNA comprises two distinct RNA molecules that are non-covalently associated to form a duplex. See, for example, U.S. Pat. No. 7,195,916.

When appropriately targeted via its nucleotide sequence to p63, p53, and/or p21 mRNA in cells, an siRNA or shRNA can specifically suppress gene expression through a process known as RNA interference (RNAi). siRNAs or shRNAs can reduce the cellular level of specific p63, p53, and/or p21 mRNAs, respectively, and decrease the level of proteins coded by such mRNAs. siRNAs and shRNAs utilize sequence complementarity to target an mRNA for destruction, and are sequence-specific. Thus, they can be highly target-specific, and in mammals have been shown to target mRNAs encoded by different alleles of the same gene.

It should further be noted that full complementarity between the target sequence and the antisense siRNA or shRNA is not required. That is, the resultant antisense siRNA or shRNA is sufficiently complementary with the target sequence. The sense strand is substantially complementary with the antisense strand to anneal (hybridize) to the antisense strand under biological conditions.

In particular, the complementary polynucleotide sequence of shRNA can be designed to specifically hybridize to a particular region of p63, p53, and/or p21 mRNA to interfere with replication, transcription, or translation. The term "hybridize" or variations thereof, refers to a sufficient degree of complementarity or pairing between an antisense nucleotide sequence and p63, p53, and/or p21 DNA or mRNA such that stable and specific binding occurs there between. In particular, 100% complementarity or pairing is desirable but not required. Specific hybridization occurs when sufficient hybridization occurs between the antisense nucleotide sequence and p63 nucleic acids in the substantial absence of non-specific binding of the antisense nucleotide sequence to non-target sequences under predetermined conditions, e.g., for purposes of in vivo treatment, preferably under physiological conditions. Preferably, specific hybridization results in the interference with normal expression of the p63, p53, and/or p21 gene product encoded by the target p63, p53, and/or p21 DNA or mRNA.

For example, a p63, p53, and/or p21 antisense nucleotide sequence can be designed to specifically hybridize to the replication or transcription regulatory regions of p63, or the translation regulatory regions such as translation initiation region and exon/intron junctions, or the coding regions of a p63, p53, and/or p21 mRNA.

p63, p53, and/or p21 siRNA or shRNA: Synthesis

As is generally known in the art, commonly used oligonucleotides are oligomers or polymers of ribonucleic acid or deoxyribonucleic acid having a combination of naturally-occurring purine and pyrimidine bases, sugars and covalent linkages between nucleosides including a phosphate group in a phosphodiester linkage. However, it is noted that the term "oligonucleotides" also encompasses various non-naturally occurring mimetics and derivatives, i.e., modified forms, of naturally-occurring oligonucleotides as described below.

p63, p53, and/or p21 siRNA or shRNA molecules of the invention can be prepared by any method known in the art for the synthesis of DNA and RNA molecules. These include techniques for chemically synthesizing oligodeoxy-ribonucleotides and oligo-ribonucleotides well known in the art such as for example solid phase phosphoramidite chemical synthesis. Alternatively, RNA molecules can be generated by in vitro and in vivo transcription of DNA sequences encoding the antisense RNA molecule. Such DNA sequences may be incorporated into a wide variety of vectors that incorporate suitable RNA polymerase promoters such as the T7 or SP6 polymerase promoters. Alternatively, antisense cDNA constructs that synthesize antisense RNA constitutively or inducibly, depending on the promoter used, can be introduced stably into cell lines.

p63, p53, and/or p21 siRNA or shRNA molecules can be chemically synthesized using appropriately protected ribonucleoside phosphoramidites and a conventional DNA/RNA synthesizer. Custom siRNA synthesis services are available from commercial vendors such as Ambion (Austin, Tex., USA) and Dharmacon Research (Lafayette, Colo., USA). See, for example, U.S. Pat. No. 7,410,944.

Various well-known modifications to the DNA molecules can be introduced as a means of increasing intracellular stability and half-life. Possible modifications include, but are not limited to, the addition of flanking sequences of ribo- or deoxy-nucleotides to the 5' and/or 3' ends of the molecule or the use of phosphorothioate or 2' O-methyl rather than phosphodiesterase linkages within the oligodeoxyribonucleotide backbone. An antisense nucleic acid of the disclosure can be constructed using chemical synthesis or enzymatic ligation reactions using procedures known in the art. An antisense oligonucleotide can be chemically synthesized using naturally-occurring nucleotides or variously modified nucleotides designed to increase the biological stability of the molecules or to increase the physical stability of the duplex formed between the antisense and sense nucleic acids (e.g., phosphorothioate derivatives and acridine substituted nucleotides can be used).

The p63, p53, and/or p21 siRNA or shRNA molecules of the disclosure can be various modified equivalents of the structures of any p63, p53, and/or p21 siRNA or shRNA. A "modified equivalent" means a modified form of a particular siRNA or shRNA molecule having the same target-specificity (i.e., recognizing the same mRNA molecules that complement the unmodified particular siRNA molecule). Thus, a modified equivalent of an unmodified siRNA or shRNA molecule can have modified ribonucleotides, that is, ribonucleotides that contain a modification in the chemical structure of an unmodified nucleotide base, sugar and/or phosphate (or phosphodiester linkage). See, for example, U.S. Pat. No. 7,410,944.

Preferably, modified p63, p53, and/or p21 siRNA or shRNA molecules contain modified backbones or non-natural internucleoside linkages, e.g., modified phosphorous-containing backbones and non-phosphorous backbones such as morpholino backbones; siloxane, sulfide, sulfoxide, sulfone, sulfonate, sulfonamide, and sulfamate backbones; formacetyl and thioformacetyl backbones; alkene-containing backbones; methyleneimino and methylenehydrazino backbones; amide backbones, and the like. See, for example, U.S. Pat. No. 7,410,944.

Examples of modified phosphorous-containing backbones include, but are not limited to phosphorothioates, phosphorodithioates, chiral phosphorothioates, phosphotriesters, aminoalkylphosphotriesters, alkyl phosphonates, thionoalkylphosphonates, phosphinates, phosphoramidates, thionophosphoramidates, thionoalkylphosphotriesters, and boranophosphates and various salt forms thereof. See, for example, U.S. Pat. No. 7,410,944.

Examples of the non-phosphorous containing backbones described above are known in the art, e.g., U.S. Pat. No. 5,677,439, each of which is herein incorporated by reference. See, for example, U.S. Pat. No. 7,410,944.

Modified forms of p63, p53, and/or p21 siRNA or shRNA compounds can also contain modified nucleosides (nucleoside analogs), i.e., modified purine or pyrimidine bases, e.g., 5-substituted pyrimidines, 6-azapyrimidines, pyridin-4-one, pyridin-2-one, phenyl, pseudouracil, 2,4,6-trimethoxy benzene, 3-methyl uracil, dihydrouridine, naphthyl, aminophenyl, 5-alkylcytidines (e.g., 5-methylcytidine), 5-alkyluridines (e.g., ribothymidine), 5-halouridine (e.g., 5-bromouridine) or 6-azapyrimidines or 6-alkylpyrimidines (e.g. 6-methyluridine), 2-thiouridine, 4-thiouridine, 5-(carboxyhydroxy methyl)uridine, 5'-carboxymethylaminomethyl-2-thiouridine, 5-carboxymethylaminomethyluridine, 5-methoxyaminomethyl-2-thiouridine, 5-methylaminomethyluridine, 5-methylcarbonylmethyl uridine, 5-methyloxyuridine, 5-methyl-2-thiouridine, 4-acetylcytidine, 3-methylcytidine, propyne, quesosine, wybutosine, wybutoxosine, beta-D-galactosylqueosine, N-2, N-6 and O-substituted purines, inosine, 1-methyladenosine, 1-methylinosine, 2,2-dimethylguanosine, 2-methyladenosine, 2-methylguanosine, N6-methyladenosine, 7-methylguanosine, 2-methylthio-N-6-isopentenyl adenosine, beta-D-mannosylqueosine, uridine-5-oxyacetic acid, 2-thiocytidine, threonine derivatives, and the like. See, for example, U.S. Pat. No. 7,410,944. In addition, modified siRNA compounds can also have substituted or modified sugar moieties, e.g., 2'-O-methoxyethyl sugar moieties. See, for example, U.S. Pat. No. 7,410,944. In specific embodiments, the 3' overhangs of the siRNAs or shRNAs of the present disclosure are modified to provide resistance to cellular nucleases. In one embodiment the 3' overhangs comprise 2'-deoxyribonucleotides.

Additionally, to assist in the design of p63, p53, and/or p21 siRNAs or shRNAs for the efficient RNAi-mediated silencing of any target gene, several siRNA or shRNA supply companies maintain web-based design tools that utilize these general guidelines for selecting siRNAs or shRNAs when presented with the mRNA or coding DNA sequence of the target gene. Examples of such tools can be found at the web sites of Dharmacon, Inc. (Lafayette, Colo.), Ambion, Inc. (Austin, Tex.). As an example, selecting siR- NAs involves choosing a site/sequence unique to the target gene (i.e., sequences that share no significant homology with genes other than the one being targeted), so that other genes are not inadvertently targeted by the same siRNA designed for this particular target sequence.

Another criterion to be considered is whether or not the target sequence includes a known polymorphic site. If so, siRNAs or shRNAs designed to target one particular allele may not effectively target another allele, since single base mismatches between the target sequence and its complementary strand in a given siRNA or shRNA can greatly reduce the effectiveness of RNAi induced by that respective siRNA or shRNA. Given that target sequence and such design tools and design criteria, an ordinarily skilled artisan apprised of the present disclosure should be able to design and synthesized additional siRNA or shRNA compounds useful in reducing the mRNA level of p63.

p63, p53, and/or p21 siRNA or shRNA: Administration

The present invention provides a composition of a polymer or excipient and one or more vectors encoding one or more p63, p53, and/or p21 siRNA or shRNA molecules. The vector can be formulated into a pharmaceutical composition with suitable carriers and administered into a mammal using any suitable route of administration, including injection into the heart, for example.

Because of this precision, side effects typically associated with traditional drugs can be reduced or eliminated. In addition, siRNAs or shRNAs are relatively stable, and like antisense, they can also be modified to achieve improved pharmaceutical characteristics, such as increased stability, deliverability, and ease of manufacture. Moreover, because siRNA or shRNA molecules take advantage of a natural cellular pathway, i.e., RNA interference, they are highly efficient in destroying targeted mRNA molecules. As a result, it is relatively easy to achieve a therapeutically effective concentration of an siRNA or shRNA compound in a subject. See, for example, U.S. Pat. No. 7,410,944.

siRNA or shRNA compounds may be administered to mammals by various methods through different routes. They can also be delivered directly to a particular organ or tissue by any suitable localized administration methods such as direct injection into a target tissue. Alternatively, they may be delivered encapsulated in liposomes, by iontophoresis, or by incorporation into other vehicles such as hydrogels, cyclodextrins, biodegradable nanocapsules, and bioadhesive microspheres.

In vivo inhibition of specific gene expression by RNAi injected intravenously has been achieved in various organisms including mammals One route of administration of shRNA molecules of the disclosure includes direct injection of the vector at a desired tissue site, such as for example, into diseased or non-diseased cardiac tissue, into ischemic heart tissue.

In one aspect of the invention, one or more vectors comprising one or more of shRNA of the invention can be re-administered an unlimited number of times after a first administration at any time interval or intervals after the first administration.

p63, p53, and/or p21 siRNA or shRNA: Pharmaceutical Compositions

The p63, p53, and/or p21 siRNA or shRNA encoding nucleic acids of the present invention can be formulated in pharmaceutical compositions, which are prepared according to conventional pharmaceutical compounding techniques. See, e.g., Remington's Pharmaceutical Sciences, 18th Ed. (1990, Mack Publishing Co., Easton, Pa.). The pharmaceutical compositions of the invention comprise a therapeutically effective amount of the vector encoding shRNA. These compositions can comprise, in addition to the vector, a pharmaceutically acceptable excipient, carrier, buffer, stabilizer or other materials well known in the art. Such materials should be non-toxic and should not interfere with the efficacy of the active ingredient. The carrier can take a wide variety of forms depending on the form of preparation desired for administration, e.g., intravenous, oral, intramuscular, subcutaneous, intrathecal, epineural or parenteral.

When the vectors of the disclosure are prepared for administration, they may be combined with a pharmaceutically acceptable carrier, diluent or excipient to form a pharmaceutical formulation, or unit dosage form. The total active ingredients in such formulations include from 0.1 to 99.9% by weight of the formulation In another aspect of the invention, the vectors of the disclosure can be suitably formulated and introduced into the environment of the cell by any means that allows for a sufficient portion of the sample to enter the cell to induce gene silencing, if it is to occur. Many formulations for vectors are known in the art and can be used so long as the vectors gain entry to the target cells so that it can act.

For example, the vectors can be formulated in buffer solutions such as phosphate buffered saline solutions comprising liposomes, micellar structures, and capsids. The pharmaceutical formulations of the vectors of the invention can also take the form of an aqueous or anhydrous solution or dispersion, or alternatively the form of an emulsion or suspension. The pharmaceutical formulations of the vectors of the present invention may include, as optional ingredients, solubilizing or emulsifying agents, and salts of the type that are well-known in the art. Specific non-limiting examples of the carriers and/or diluents that are useful in the pharmaceutical formulations of the present invention include water and physiologically acceptable saline solutions. Other pharmaceutically acceptable carriers for preparing a composition for administration to an individual include, for example, solvents or vehicles such as glycols, glycerol, or injectable organic esters. A pharmaceutically acceptable carrier can contain physiologically acceptable compounds that act, for example, to stabilize or to increase the absorption of the shRNA encoding vector. Other physiologically acceptable carriers include, for example, carbohydrates, such as glucose, sucrose or dextrans, antioxidants, such as ascorbic acid or glutathione, chelating agents, low molecular weight proteins or other stabilizers or excipients, saline, dextrose solutions, fructose solutions, ethanol, or oils of animal, vegetative or synthetic origin. The carrier can also contain other ingredients, for example, preservatives.

It will be recognized that the choice of a pharmaceutically acceptable carrier, including a physiologically acceptable compound, depends, for example, on the route of administration of the composition. The composition containing the vectors can also contain a second reagent such as a diagnostic reagent, nutritional substance, toxin, or additional therapeutic agent. Many agents useful in the treatment of cardiac disease are known in the art and are envisioned for use in conjunction with the vectors of this invention.

Formulations of vectors with cationic lipids can be used to facilitate transfection of the vectors into cells. For example, cationic lipids, such as lipofectin, cationic glycerol derivatives, and polycationic molecules, such as polylysine, can be used. Suitable lipids include, for example, Oligofectamine and Lipofectamine (Life Technologies) which can be used according to the manufacturer's instructions.

Suitable amounts of vector must be introduced and these amounts can be empirically determined using standard methods. Typically, effective concentrations of individual vector species in the environment of a cell will be about 50 nanomolar or less 10 nanomolar or less, or compositions in which concentrations of about 1 nanomolar or less can be used. In other aspects, the methods utilize a concentration of about 200 picomolar or less and even a concentration of about 50 picomolar or less can be used in many circumstances. One of skill in the art can determine the effective concentration for any particular mammalian subject using standard methods.

The p63, p53, and/or p21 siRNA or shRNA is administered in a therapeutically effective amount. The actual amount administered, and the rate and time-course of administration, will depend on the nature and severity of the condition, disease or disorder being treated. Prescription of treatment, for example, decisions on dosage, timing, etc., is within the responsibility of general practitioners or specialists, and typically takes account of the disorder, condition or disease to be treated, the condition of the individual mammalian subject, the site of delivery, the method of administration and other factors known to practitioners. Examples of techniques and protocols can be found in Remington's Pharmaceutical Sciences 18th Ed. (1990, Mack Publishing Co., Easton, Pa.).

Alternatively, targeting therapies can be used to deliver the shRNA encoding vectors more specifically to certain types of cell, by the use of targeting systems such as antibodies or cell specific ligands. Targeting can be desirable for a variety of reasons, e.g., if the agent is unacceptably toxic, or if it would otherwise require too high a dosage, or if it would not otherwise be able to enter the target cells.

p63, p53, and/or p21 siRNA or shRNA: Gene Therapy p63, p53, and/or p21 siRNA or shRNA can also be delivered into mammalian cells, particularly human cells, by a gene therapy approach, using a DNA vector, for example. In specific embodiments a vector from which siRNA compounds in, e.g., small hairpin form (shRNA), can be transcribed directly is utilized. Studies have demonstrated that while double-stranded siRNAs are very effective at mediating RNAi, short, single-stranded, hairpin-shaped RNAs can also mediate RNAi, presumably because they fold into intramolecular duplexes that are processed into double-stranded siRNAs by cellular enzymes. This discovery has significant and far-reaching implications, since the production of such shRNAs can be readily achieved in vivo by transfecting cells or tissues with DNA vectors bearing short inverted repeats separated by a small number of (e.g., 3, 4, 5, 6, 7, 8, 9) nucleotides that direct the transcription of such small hairpin RNAs. Additionally, if mechanisms are included to direct the integration of the vector or a vector segment into the host-cell genome, or to ensure the stability of the transcription vector, the RNAi caused by the encoded shRNAs, can be made stable and heritable. Not only have such techniques been used to "knock down" the expression of specific genes in mammalian cells, but they have now been successfully employed to knock down the expression of exogenously expressed transgenes, as well as endogenous genes in the brain and liver of living mice.

Gene therapy is carried out according to generally accepted methods as are known in the art. See, for example, U.S. Pat. Nos. 5,837,492 and 5,800,998 and references cited therein. Vectors in the context of gene therapy are meant to include those polynucleotide sequences containing sequences sufficient to express a polynucleotide encoded therein. If the polynucleotide encodes an shRNA, expression will produce the antisense polynucleotide sequence. Thus, in this context, expression does not require that a protein product be synthesized. In addition to the shRNA encoded in the vector, the vector also contains a promoter functional in eukaryotic cells. The shRNA sequence is under control of this promoter. Suitable eukaryotic promoters include those described elsewhere herein and as are known in the art. The expression vector may also include sequences, such as selectable markers, reporter genes and other regulatory sequences conventionally used.

Accordingly, the amount of siRNA generated in situ is regulated by controlling such factors as the nature of the promoter used to direct transcription of the nucleic acid sequence, (i.e., whether the promoter is constitutive or regulatable, strong or weak) and the number of copies of the nucleic acid sequence encoding a siRNA sequence that are in the cell.

III. Embodiments of Cardiac Cell Reprogramming Factors and Chromatin Destabilizing Agents Certain embodiments of the present disclosure concern nucleic acids, and some embodiments concern polypeptides or peptides. In certain aspects, nucleic acids include a one or more agents that partially or completely downregulates or inactivates p63, p53, and/or p21, such as by downregulating or inactivating their expression. In specific embodiments, the agent comprises RNA interference nucleic acid (such as shRNA or siRNA). In particular embodiments, the agent(s) may or may not be utilized with one or more cardiac cell reprogramming factors and may or may not be used with one or more chromatin destabilizing agents.

Cardiac Cell Reprogramming Factors

In specific embodiments, one or more cardiac cell reprogramming factors are employed in methods of the disclosure, and the factors may or may not be provided at the same time as the agent that partially or completely downregulates or inactivates p63, p53, and/or p21. In specific embodiments, the factors are provided after the individual has received the p63, p53, and/or p21-inactivating agent(s), although in some cases they are provided before or at the same time as the agent(s).

The cardiac cell reprogramming factor may or may not be a transcription factor. Although one could use standard methods to test whether or not a certain compound would be effective as a cardiac cell reprogramming factor, in specific embodiments the factor is Hand2, myocardin, Gata4, Mef2c, Tbx5, Mesoderm posterior protein 1 (Mesp1), miR-133, miR-1, Oct4, Klf4, c-myc, Sox2, Brachyury, Nkx2.5, ETS2, ESRRG, Mrtf-A, MyoD, ZFPM2, or a combination thereof. One could test whether or not a compound acted as a cardiac cell reprogramming factor by administering it to fibroblasts (e.g., using lentivirus) and perform FACS for cTnT as illustrated elsewhere herein. The factors may be employed as nucleic acids, polypeptides, peptides of specific domains of the factor, or a combination thereof. In specific embodiments, Hand2 and/or myocardin are employed, including as nucleic acids. In particular aspects at least for Hand2 and/or myocardin, the nucleic acid encodes for or comprises a tra.,anscribed nucleic acid. In other aspects, a Hand2 and/or myocardin nucleic acid comprises a nucleic acid segment of Hand2 and/or myocardin, respectively, or a biologically functional equivalent thereof. In particular aspects, a Hand2 and/or myocardin nucleic acid encodes a protein, polypeptide, or peptide. An exemplary human Hand2 nucleic acid is at the GenBank® database of National Center for Biotechnology Information, Accession No. NM_021973, which is incorporated by reference herein in its entirety. An exemplary human myocardin nucleic acid is at GenBank® Accession Number AY764180, which is incorporated by reference herein in its entirety. An exemplary human p63 nucleic acid sequence is at GenBank Accession Number NM_003722, and the skilled artisan recognizes that interference of p63 nucleic acid would comprise sequence that is complementary to at least part of the p63, p53, and/or p21 mRNA. In specific embodiments, the p63, p53, and/or p21 shRNA is capable of DNA integration and comprises two complementary 19-22 bp RNA sequences linked by a short loop of 4-11 nt, wherein the region of complementarity may be to any region of the p63 nucleic acid sequence, including coding or non-coding sequence.

In specific embodiments, a functional fragment of the cardiac cell reprogramming factor nucleic acid or polypeptide is utilized instead of the entire factor nucleic acid or polypeptide. A functional fragment of either Hand2 or myocardin (as an example) is one that is sufficient to allow reprogramming of cells upon exposure to the fragment, either alone with p63, p53, and/or p21 shRNA or in conjunction with myocardin and p63, p53, and/or p21 shRNA. In specific embodiments, the functional fragment of Hand2 nucleic acid encodes at least 200, 180, 175, 160, 150, 140, 125, 110, 100, 90, 80, 75, 70, 60, 55, 50, 40, 30, 25, or 19 amino acids of the Hand2 polypeptide. In specific embodiments, the functional fragment of myocardin nucleic acid encodes at least 900, 800, 700, 600, 500, 400, 300, 200, 100, or 50 amino acids of the myocardin polypeptide.

Chromatin Destabilizing Agents

In particular embodiments, one or more chromatin destabilizing agents are utilized with one or more p63, p53, and/or p21 inactivating agents. The one or more chromatin destabilizing agents may be provided to an individual at the same time as the one or more p63, p53, and/or p21 inactivating agents, although in specific embodiments the one or more chromatin destabilizing agents are utilized before or after one or more p63, p53, and/or p21 inactivating agents.

Although one could use standard methods to test whether or not a certain compound would be effective as a chromatin destabilizing agent, in specific embodiments the chromatin destabilizing agent is Oct4, DZNep, Sa114, SOX2, KLF4, MYC, SB431542, PD0325901, Parnate. CHIR99021, A-83-01. NaB, PS48, Forskolin (FSK), 2-methyl-5-hydroxytryptamine (2-Me-5HT), D4476, VPA,CHIR99021 (CHIR), 616452, Tranylcypromine, Prostaglandin E2, Rolipram, 3-deazaneplanocin A (DZNep), 5-Azacytidine, sodium butyrate, RG108 or a combination thereof.

The term "nucleic acid" is well known in the art. A "nucleic acid" as used herein will generally refer to a molecule (i.e., a strand) of DNA, RNA or a derivative or analog thereof, comprising a nucleobase. A nucleobase includes, for example, a naturally occurring purine or pyrimidine base found in DNA (e.g., an adenine "A," a guanine "G," a thymine "T" or a cytosine "C") or RNA (e.g., an A, a G, an uracil "U" or a C). The term "nucleic acid" encompass the terms "oligonucleotide" and "polynucleotide," each as a subgenus of the term "nucleic acid." The term "oligonucleotide" refers to a molecule of between about 3 and about 100 nucleobases in length. The term "polynucleotide" refers to at least one molecule of greater than about 100 nucleobases in length, in at least some cases.

These definitions generally refer to a single-stranded molecule, but in specific embodiments will also encompass an additional strand that is partially, substantially or fully complementary to the single-stranded molecule. Thus, a nucleic acid may encompass a double-stranded molecule or a triple-stranded molecule that comprises one or more complementary strand(s) or "complement(s)" of a particular sequence comprising a molecule. As used herein, a single stranded nucleic acid may be denoted by the prefix "ss," a double stranded nucleic acid by the prefix "ds," and a triple stranded nucleic acid by the prefix "ts."

A. Nucleobases

As used herein a "nucleobase" refers to a heterocyclic base, such as for example a naturally occurring nucleobase (i.e., an A, T, G, C or U) found in at least one naturally occurring nucleic acid (i.e., DNA and RNA), and naturally or non-naturally occurring derivative(s) and analogs of such a nucleobase. A nucleobase generally can form one or more hydrogen bonds ("anneal" or "hybridize") with at least one naturally occurring nucleobase in manner that may substitute for naturally occurring nucleobase pairing (e.g., the hydrogen bonding between A and T, G and C, and A and U).

"Purine" and/or "pyrimidine" nucleobase(s) encompass naturally occurring purine and/or pyrimidine nucleobases and also derivative(s) and analog(s) thereof, including but not limited to, those a purine or pyrimidine substituted by one or more of an alkyl, caboxyalkyl, amino, hydroxyl, halogen (i.e., fluoro, chloro, bromo, or iodo), thiol or alkylthiol moiety. Preferred alkyl (e.g., alkyl, caboxyalkyl, etc.) moeities comprise of from about 1, about 2, about 3, about 4, about 5, to about 6 carbon atoms. Other non-limiting examples of a purine or pyrimidine include a deazapurine, a 2,6-diaminopurine, a 5-fluorouracil, a xanthine, a hypoxanthine, a 8-bromoguanine, a 8-chloroguanine, a bromothymine, a 8-aminoguanine, a 8-hydroxyguanine, a 8-methylguanine, a 8-thioguanine, an azaguanine, a 2-aminopurine, a 5-ethylcytosine, a 5-methylcyosine, a 5-bromouracil, a 5-ethyluracil, a 5-iodouracil, a 5-chlorouracil, a 5-propyluracil, a thiouracil, a 2-methyladenine, a methylthioadenine, a N,N-diemethyladenine, an azaadenines, a 8-bromoadenine, a 8-hydroxyadenine, a 6-hydroxyaminopurine, a 6-thiopurine, a 4-(6-aminohexyl/cytosine), and the like.

A nucleobase may be comprised in a nucleoside or nucleotide, using any chemical or natural synthesis method described herein or known to one of ordinary skill in the art.

B. Nucleosides

As used herein, a "nucleoside" refers to an individual chemical unit comprising a nucleobase covalently attached to a nucleobase linker moiety. A non-limiting example of a "nucleobase linker moiety" is a sugar comprising 5-carbon atoms (i.e., a "5-carbon sugar"), including but not limited to a deoxyribose, a ribose, an arabinose, or a derivative or an analog of a 5-carbon sugar. Non-limiting examples of a derivative or an analog of a 5-carbon sugar include a 2'-fluoro-2'-deoxyribose or a carbocyclic sugar where a carbon is substituted for an oxygen atom in the sugar ring.

Different types of covalent attachment(s) of a nucleobase to a nucleobase linker moiety are known in the art. By way of non-limiting example, a nucleoside comprising a purine (i.e., A or G) or a 7-deazapurine nucleobase typically covalently attaches the 9 position of a purine or a 7-deazapurine to the 1'-position of a 5-carbon sugar. In another non-limiting example, a nucleoside comprising a pyrimidine nucleobase (i.e., C, T or U) typically covalently attaches a 1 position of a pyrimidine to a 1'-position of a 5-carbon sugar (Kornberg and Baker, 1992).

C. Nucleotides

As used herein, a "nucleotide" refers to a nucleoside further comprising a "backbone moiety". A backbone moiety generally covalently attaches a nucleotide to another molecule comprising a nucleotide, or to another nucleotide to form a nucleic acid. The "backbone moiety" in naturally occurring nucleotides typically comprises a phosphorus moiety, which is covalently attached to a 5-carbon sugar. The attachment of the backbone moiety typically occurs at either the 3'- or 5'-position of the 5-carbon sugar. However, other types of attachments are known in the art, particularly when a nucleotide comprises derivatives or analogs of a naturally occurring 5-carbon sugar or phosphorus moiety.

D. Nucleic Acid Analogs

A nucleic acid may comprise, or be composed entirely of, a derivative or analog of a nucleobase, a nucleobase linker moiety and/or backbone moiety that may be present in a naturally occurring nucleic acid. As used herein a "derivative" refers to a chemically modified or altered form of a naturally occurring molecule, while the terms "mimic" or "analog" refer to a molecule that may or may not structurally resemble a naturally occurring molecule or moiety, but possesses similar functions. As used herein, a "moiety" generally refers to a smaller chemical or molecular component of a larger chemical or molecular structure. Nucleobase, nucleoside and nucleotide analogs or derivatives are well known in the art, and have been described (see for example, Scheit, 1980, incorporated herein by reference).

Additional non-limiting examples of nucleosides, nucleotides or nucleic acids comprising 5-carbon sugar and/or backbone moiety derivatives or analogs, include those in U.S. Pat. No. 5,681,947 which describes oligonucleotides comprising purine derivatives that form triple helixes with and/or prevent expression of dsDNA; U.S. Pat. Nos. 5,652,099 and 5,763,167 which describe nucleic acids incorporating fluorescent analogs of nucleosides found in DNA or RNA, particularly for use as flourescent nucleic acids probes; U.S. Pat. No. 5,614,617 which describes oligonucleotide analogs with substitutions on pyrimidine rings that possess enhanced nuclease stability; U.S. Pat. Nos. 5,670,663, 5,872,232 and 5,859,221 which describe oligonucleotide analogs with modified 5-carbon sugars (i.e., modified 2'-deoxyfuranosyl moieties) used in nucleic acid detection; U.S. Pat. No. 5,446,137 which describes oligonucleotides comprising at least one 5-carbon sugar moiety substituted at the 4' position with a substituent other than hydrogen that can be used in hybridization assays; U.S. Pat. No. 5,886,165 which describes oligonucleotides with both deoxyribonucleotides with 3'-5' internucleotide linkages and ribonucleotides with 2'-5' internucleotide linkages; U.S. Pat. No. 5,714,606 which describes a modified internucleotide linkage wherein a 3'-position oxygen of the internucleotide linkage is replaced by a carbon to enhance the nuclease resistance of nucleic acids; U.S. Pat. No. 5,672,697 which describes oligonucleotides containing one or more 5' methylene phosphonate internucleotide linkages that enhance nuclease resistance; U.S. Pat. Nos. 5,466,786 and 5,792,847 which describe the linkage of a substituent moiety which may comprise a drug or label to the 2' carbon of an oligonucleotide to provide enhanced nuclease stability and ability to deliver drugs or detection moieties; U.S. Pat. No. 5,223,618 which describes oligonucleotide analogs with a 2 or 3 carbon backbone linkage attaching the 4' position and 3' position of adjacent 5-carbon sugar moiety to enhanced cellular uptake, resistance to nucleases and hybridization to target RNA; U.S. Pat. No. 5,470,967 which describes oligonucleotides comprising at least one sulfamate or sulfamide internucleotide linkage that are useful as nucleic acid hybridization probe; U.S. Pat. Nos. 5,378,825, 5,777,092, 5,623,070, 5,610,289 and 5,602,240 which describe oligonucleotides with three or four atom linker moiety replacing phosphodiester backbone moiety used for improved nuclease resistance, cellular uptake and regulating RNA expression; U.S. Pat. No. 5,858,988 which describes hydrophobic carrier agent attached to the 2'-O position of oligonucleotides to enhanced their membrane permeability and stability; U.S. Pat. No. 5,214,136 which describes olignucleotides conjugated to anthraquinone at the 5' terminus that possess enhanced hybridization to DNA or RNA; enhanced stability to nucleases; U.S. Pat. No. 5,700,922 which describes PNA-DNA-PNA chimeras wherein the DNA comprises 2'-deoxy-erythro-pentofuranosyl nucleotides for enhanced nuclease resistance, binding affinity, and ability to activate RNase H; and U.S. Pat. No. 5,708,154 which describes RNA linked to a DNA to form a DNA-RNA hybrid.

E. Polyether and Peptide Nucleic Acids

In certain embodiments, it is contemplated that a nucleic acid comprising a derivative or analog of a nucleoside or nucleotide may be used in the methods and compositions of the disclosure. A non-limiting example is a "polyether nucleic acid", described in U.S. Pat. No. 5,908,845, incorporated herein by reference. In a polyether nucleic acid, one or more nucleobases are linked to chiral carbon atoms in a polyether backbone.

Another non-limiting example is a "peptide nucleic acid", also known as a "PNA", "peptide-based nucleic acid analog" or "PENAM", described in U.S. Pat. Nos. 5,786,461, 5891,625, 5,773,571, 5,766,855, 5,736,336, 5,719,262, 5,714,331, 5,539,082, and WO 92/20702, each of which is incorporated herein by reference. Peptide nucleic acids generally have enhanced sequence specificity, binding properties, and resistance to enzymatic degradation in comparison to molecules such as DNA and RNA (Egholm et al., 1993; PCT/EP/01219). A peptide nucleic acid generally comprises one or more nucleotides or nucleosides that comprise a nucleobase moiety, a nucleobase linker moiety that is not a 5-carbon sugar, and/or a backbone moiety that is not a phosphate backbone moiety. Examples of nucleobase linker moieties described for PNAs include aza nitrogen atoms, amido and/or ureido tethers (see for example, U.S. Pat. No. 5,539,082). Examples of backbone moieties described for PNAs include an aminoethylglycine, polyamide, polyethyl, polythioamide, polysulfinamide or polysulfonamide backbone moiety.

In certain embodiments, a nucleic acid analogue such as a peptide nucleic acid may be used to inhibit nucleic acid amplification, such as in PCR, to reduce false positives and discriminate between single base mutants, as described in U.S. Pat. No. 5,891,625. Other modifications and uses of nucleic acid analogs are known in the art, and are encompassed herein. In a non-limiting example, U.S. Pat. No. 5,786,461 describes PNAs with amino acid side chains attached to the PNA backbone to enhance solubility of the molecule. In another example, the cellular uptake property of PNAs is increased by attachment of a lipophilic group. U.S. application Ser. No. 117,363 describes several alkylamino moeities used to enhance cellular uptake of a PNA. Another example is described in U.S. Pat. Nos. 5,766,855, 5,719,262, 5,714,331 and 5,736,336, which describe PNAs comprising naturally and non-naturally occurring nucleobases and alkylamine side chains that provide improvements in sequence specificity, solubility and/or binding affinity relative to a naturally occurring nucleic acid.

F. Preparation of Nucleic Acids

A nucleic acid may be made by any technique known to one of ordinary skill in the art, such as for example, chemical synthesis, enzymatic production or biological production. Non-limiting examples of a synthetic nucleic acid (e.g., a synthetic oligonucleotide), include a nucleic acid made by in vitro chemical synthesis using phosphotriester, phosphite or phosphoramidite chemistry and solid phase techniques such as described in EP 266,032, incorporated herein by reference, or via deoxynucleoside H-phosphonate intermediates as described by Froehler et al., 1986 and U.S. Pat. No.

5,705,629, each incorporated herein by reference. In the methods of the present disclosure, one or more oligonucleotide may be used. Various different mechanisms of oligonucleotide synthesis have been disclosed in for example, U.S. Pat. Nos. 4,659,774, 4,816,571, 5,141,813, 5,264,566, 4,959,463, 5,428,148, 5,554,744, 5,574,146, 5,602,244, each of which is incorporated herein by reference.

A non-limiting example of an enzymatically produced nucleic acid include one produced by enzymes in amplification reactions such as PCR™ (see for example, U.S. Pat. Nos. 4,683,202 and 4,682,195, each incorporated herein by reference), or the synthesis of an oligonucleotide described in U.S. Pat. No. 5,645,897, incorporated herein by reference. A non-limiting example of a biologically produced nucleic acid includes a recombinant nucleic acid produced (i.e., replicated) in a living cell, such as a recombinant DNA vector replicated in bacteria (see for example, Sambrook et al. 1989, incorporated herein by reference).

G. Purification of Nucleic Acids

A nucleic acid may be purified on polyacrylamide gels, cesium chloride centrifugation gradients, or by any other means known to one of ordinary skill in the art (see for example, Sambrook et al., 1989, incorporated herein by reference).

In certain aspect, the present disclosure concerns a nucleic acid that is an isolated nucleic acid. As used herein, the term "isolated nucleic acid" refers to a nucleic acid molecule (e.g., an RNA or DNA molecule) that has been isolated free of, or is otherwise free of, the bulk of the total genomic and transcribed nucleic acids of one or more cells. In certain embodiments, "isolated nucleic acid" refers to a nucleic acid that has been isolated free of, or is otherwise free of, bulk of cellular components or in vitro reaction components such as for example, macromolecules such as lipids or proteins, small biological molecules, and the like.

H. Nucleic Acid Segments

In certain embodiments, the nucleic acid is a nucleic acid segment. As used herein, the term "nucleic acid segment," are smaller fragments of a nucleic acid, such as for non-limiting example, those that encode only part of the peptide or polypeptide sequence. Thus, a "nucleic acid segment" may comprise any part of a gene sequence, of from about 2 nucleotides to the full length of the peptide or polypeptide encoding region.

Various nucleic acid segments may be designed based on a particular nucleic acid sequence, and may be of any length. By assigning numeric values to a sequence, for example, the first residue is 1, the second residue is 2, etc., an algorithm defining all nucleic acid segments can be created:

n to n+y where n is an integer from 1 to the last number of the sequence and y is the length of the nucleic acid segment minus one, where n+y does not exceed the last number of the sequence. Thus, for a 10-mer, the nucleic acid segments correspond to bases 1 to 10, 2 to 11, 3 to 12 . . . and so on. For a 15-mer, the nucleic acid segments correspond to bases 1 to 15, 2 to 16, 3 to 17 . . . and so on. For a 20-mer, the nucleic segments correspond to bases 1 to 20, 2 to 21, 3 to 22 . . . and so on. In certain embodiments, the nucleic acid segment may be a probe or primer. As used herein, a "probe" generally refers to a nucleic acid used in a detection method or composition. As used herein, a "primer" generally refers to a nucleic acid used in an extension or amplification method or composition.

I. Nucleic Acid Complements

The present disclosure also encompasses a nucleic acid that is complementary to a p63 nucleic acid. In particular embodiments the disclosure encompasses a nucleic acid or a nucleic acid segment complementary to the p63 encoding sequence. A nucleic acid "complement(s)" or is "complementary" to another nucleic acid when it is capable of base-pairing with another nucleic acid according to the standard Watson-Crick, Hoogsteen or reverse Hoogsteen binding complementarity rules. As used herein "another nucleic acid" may refer to a separate molecule or a spatial separated sequence of the same molecule.

As used herein, the term "complementary" or "complement(s)" also refers to a nucleic acid comprising a sequence of consecutive nucleobases or semiconsecutive nucleobases (e.g., one or more nucleobase moieties are not present in the molecule) capable of hybridizing to another nucleic acid strand or duplex even if less than all the nucleobases do not base pair with a counterpart nucleobase. In certain embodiments, a "complementary" nucleic acid comprises a sequence in which about 70%, about 71%, about 72%, about 73%, about 74%, about 75%, about 76%, about 77%, about 77%, about 78%, about 79%, about 80%, about 81%, about 82%, about 83%, about 84%, about 85%, about 86%, about 87%, about 88%, about 89%, about 90%, about 91%, about 92%, about 93%, about 94%, about 95%, about 96%, about 97%, about 98%, about 99%, to about 100%, and any range derivable therein, of the nucleobase sequence is capable of base-pairing with a single or double stranded nucleic acid molecule during hybridization. In certain embodiments, the term "complementary" refers to a nucleic acid that may hybridize to another nucleic acid strand or duplex in stringent conditions, as would be understood by one of ordinary skill in the art.

In certain embodiments, a "partly complementary" nucleic acid comprises a sequence that may hybridize in low stringency conditions to a single or double stranded nucleic acid, or contains a sequence in which less than about 70% of the nucleobase sequence is capable of base-pairing with a single or double stranded nucleic acid molecule during hybridization.

J. Hybridization

As used herein, "hybridization", "hybridizes" or "capable of hybridizing" is understood to mean the forming of a double or triple stranded molecule or a molecule with partial double or triple stranded nature. The term "anneal" as used herein is synonymous with "hybridize." The term "hybridization", "hybridize(s)" or "capable of hybridizing" encompasses the terms "stringent condition(s)" or "high stringency" and the terms "low stringency" or "low stringency condition(s)."

As used herein "stringent condition(s)" or "high stringency" are those conditions that allow hybridization between or within one or more nucleic acid strand(s) containing complementary sequence(s), but precludes hybridization of random sequences. Stringent conditions tolerate little, if any, mismatch between a nucleic acid and a target strand. Such conditions are well known to those of ordinary skill in the art, and are preferred for applications requiring high selectivity. Non-limiting applications include isolating a nucleic acid, such as a gene or a nucleic acid segment thereof, or detecting at least one specific mRNA transcript or a nucleic acid segment thereof, and the like.

Stringent conditions may comprise low salt and/or high temperature conditions, such as provided by about 0.02 M to about 0.15 M NaCl at temperatures of about 50° C. to about 70° C. It is understood that the temperature and ionic strength of a desired stringency are determined in part by the length of the particular nucleic acid(s), the length and nucleobase content of the target sequence(s), the charge composition of the nucleic acid(s), and to the presence or concentration of formamide, tetramethylammonium chloride or other solvent(s) in a hybridization mixture.

It is also understood that these ranges, compositions and conditions for hybridization are mentioned by way of non-limiting examples only, and that the desired stringency for a particular hybridization reaction is often determined empirically by comparison to one or more positive or negative controls. Depending on the application envisioned it is preferred to employ varying conditions of hybridization to achieve varying degrees of selectivity of a nucleic acid towards a target sequence. In a non-limiting example, identification or isolation of a related target nucleic acid that does not hybridize to a nucleic acid under stringent conditions may be achieved by hybridization at low temperature and/or high ionic strength. Such conditions are termed "low stringency" or "low stringency conditions", and non-limiting examples of low stringency include hybridization performed at about 0.15 M to about 0.9 M NaCl at a temperature range of about 20° C. to about 50° C. Of course, it is within the skill of one in the art to further modify the low or high stringency conditions to suite a particular application.

As used herein "wild-type" refers to the naturally occurring sequence of a nucleic acid at a genetic locus in the genome of an organism, or a sequence transcribed or translated from such a nucleic acid. Thus, the term "wild-type" also may refer to an amino acid sequence encoded by a nucleic acid. As a genetic locus may have more than one sequence or alleles in a population of individuals, the term "wild-type" encompasses all such naturally occurring allele(s). As used herein the term "polymorphic" means that variation exists (i.e., two or more alleles exist) at a genetic locus in the individuals of a population. As used herein "mutant" refers to a change in the sequence of a nucleic acid or its encoded protein, polypeptide or peptide that is the result of the hand of man.

The present disclosure also concerns the isolation or creation of a recombinant construct or a recombinant host cell through the application of recombinant nucleic acid technology known to those of skill in the art or as described herein. A recombinant construct or host cell may comprise a nucleic acid, and may express a protein, peptide or peptide, or at least one biologically functional equivalent thereof.

Herein, in certain embodiments, a "gene" refers to a nucleic acid that is transcribed. In certain aspects, the gene includes regulatory sequences involved in transcription, or message production or composition. In particular embodiments, the gene comprises transcribed sequences that encode for a protein, polypeptide or peptide. As will be understood by those in the art, this function term "gene" includes both genomic sequences, RNA or cDNA sequences or smaller engineered nucleic acid segments, including nucleic acid segments of a non-transcribed part of a gene, including but not limited to the non-transcribed promoter or enhancer regions of a gene. Smaller engineered gene nucleic acid segments may express, or may be adapted to express using nucleic acid manipulation technology, proteins, polypeptides, domains, peptides, fusion proteins, mutants and/or such like.

"Isolated substantially away from other coding sequences" means that the gene of interest forms the significant part of the coding region of the nucleic acid, or that the nucleic acid does not contain large portions of naturally-occurring coding nucleic acids, such as large chromosomal fragments, other functional genes, RNA or cDNA coding regions. Of course, this refers to the nucleic acid as originally isolated, and does not exclude genes or coding regions later added to the nucleic acid by the hand of man.

The nucleic acid(s) of the present disclosure, regardless of the length of the sequence itself, may be combined with other nucleic acid sequences, including but not limited to, promoters, enhancers, polyadenylation signals, restriction enzyme sites, multiple cloning sites, coding segments, and the like, to create one or more nucleic acid construct(s). As used herein, a "nucleic acid construct" is a nucleic acid engineered or altered by the hand of man, and generally comprises one or more nucleic acid sequences organized by the hand of man.

In a non-limiting example, one or more nucleic acid constructs may be prepared that include a contiguous stretch of nucleotides identical to or complementary (at least in part) to p63. A nucleic acid construct may be about 3, about 5, about 8, about 10 to about 14, or about 15, about 20, about 30, about 40, about 50, about 100, about 115, about 200, about 500, about 600, or about 650 nucleotides in length, as well as constructs of greater size, up to and including vector sizes (including all intermediate lengths and intermediate ranges. It will be readily understood that "intermediate lengths" and "intermediate ranges", as used herein, means any length or range including or between the quoted values (i.e., all integers including and between such values). Non-limiting examples of intermediate lengths include about 11, about 12, about 13, about 16, about 17, about 18, about 19, etc.; about 21, about 22, about 23, etc.; about 31, about 32, etc.; about 51, about 52, about 53, etc.; about 101, about 102, about 103, etc.; about 151, about 152, about 153, etc.; about 600, about 601, about 605, about 610, etc. etc., etc. Non-limiting examples of intermediate ranges include about 3 to about 32, about 150 to about 750, etc.

In certain embodiments, the nucleic acid construct is a recombinant vector. In particular embodiments, the disclosure concerns one or more recombinant vector(s) comprising nucleic acid sequences that encode an Hand2 or myocardin protein, polypeptide or peptide. In particular aspects, the recombinant vectors are DNA vectors.

The term "biologically functional equivalent" is well understood in the art and is further defined in detail herein. Accordingly, a sequence that has 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, or 99% of amino acids that are identical or functionally equivalent to the amino acids encoded by the Hand2 and myocardin nucleic acids, respectively, provided the biological activity of the protein, polypeptide or peptide is maintained.

In certain other embodiments, the disclosure concerns at least one recombinant vector that includes within its sequence a nucleic acid sequence the expresses p63 shRNA. In specific embodiments, the disclosure concerns at least one recombinant vector that includes within its sequence a nucleic acid sequence that expresses Hand2 nucleic acid. In another embodiment, there is at least one recombinant vector that includes within its sequence a nucleic acid sequence that expresses myocardin nucleic acid.

The term "functionally equivalent codon" is used herein to refer to codons that encode the same amino acid, such as the six codons for arginine and serine, and also refers to codons that encode biologically equivalent amino acids. Codon usage for various organisms and organelles can be found in the literature. Thus, it is contemplated that codon usage may be optimized for other animals, as well as other organisms such as a prokaryote (e.g., an eubacteria, an archaea), an eukaryote (e.g., a protist, a plant, a fungi, an animal), a virus and the like, as well as organelles that contain nucleic acids, such as mitochondria, chloroplasts and the like, based on the preferred codon usage as would be known to those of ordinary skill in the art.

It will also be understood that amino acid sequences or nucleic acid sequences may include additional residues, such as additional N- or C-terminal amino acids or 5' or 3' sequences, or various combinations thereof, and yet still be essentially as set forth in one of the sequences disclosed herein, so long as the sequence meets the criteria set forth above, including the maintenance of biological protein, polypeptide or peptide activity where expression of a proteinaceous composition is concerned. The addition of terminal sequences particularly applies to nucleic acid sequences that may, for example, include various non-coding sequences flanking either of the 5' and/or 3' portions of the coding region or may include various internal sequences, i.e., introns, which are known to occur within genes.

Excepting intronic and flanking regions, and allowing for the degeneracy of the genetic code, nucleic acid sequences that have between about 70% and about 79%; or more preferably, between about 80% and about 89%; or even more particularly, between about 90% and about 99%; of nucleotides that are identical to the nucleotides of the noted GenBank® sequences disclosed herein are encompassed in the disclosure.

Recombinant vectors and isolated nucleic acid segments may therefore variously include Hand2 or myocardin coding regions themselves, coding regions bearing selected alterations or modifications in the basic coding region, and they may encode larger polypeptides or peptides that nevertheless include such coding regions or may encode biologically functional equivalent proteins, polypeptide or peptides that have variant amino acids sequences.

The nucleic acids of the present disclosure may encompass biologically functional equivalent coding sequences for Hand2 or myocardin proteins, polypeptides, or peptides. Such sequences may arise as a consequence of codon redundancy or functional equivalency that are known to occur naturally within nucleic acid sequences or the proteins, polypeptides or peptides thus encoded. Alternatively, functionally equivalent proteins, polypeptides or peptides may be created via the application of recombinant DNA technology, in which changes in the protein, polypeptide or peptide structure may be engineered, based on considerations of the properties of the amino acids being exchanged. Changes designed by man may be introduced, for example, through the application of site-directed mutagenesis techniques as discussed herein below, e.g., to introduce improvements or alterations to the antigenicity of the protein, polypeptide or peptide, or to test mutants in order to examine protein, polypeptide or peptide activity at the molecular level.

IV. Nucleic Acid-Based Expression Systems

Figure 25:
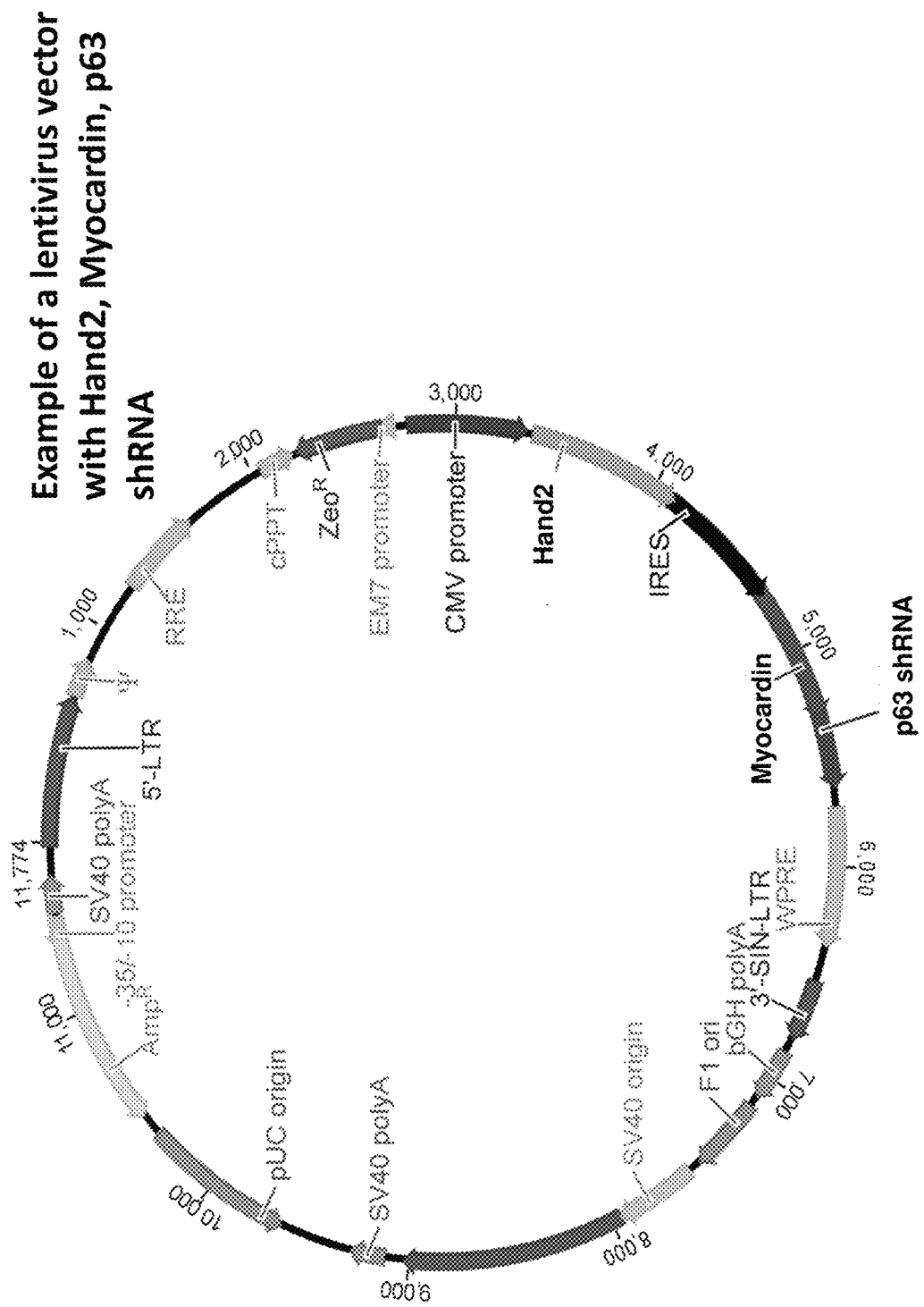
FIG. 25 illustrates an example of a lentivirus vector with Hand2, Myocardin, p63 and shRNA. An example of such a vector is a generic lentiviral shRNA model from Thermo-Scientific. RRE: Rev response element enhances titer by increasing packaging efficiency of full length viral genomes; CMV promoter: Human CMV promoter drives strong transgene expression; Hand2: Transcription factor; IRES: Internal ribosome entry site.

In particular embodiments of the disclosure, the p63, p53, and/or p21-inactivating agents (such as siRNA or shRNA nucleic acid), in some cases one or more cardiac cell reprogramming factors (such as Hand2 and/or myocardin), and in some cases one or more destabilizing agents and/or anti-fibrotic agents and/or angiogenic factors are provided in nucleic acid form to an individual in need thereof. Although in some cases the nucleic acids are not comprised on a vector, in particular embodiments the nucleic acids are present on one or more vectors. In particular embodiments, the different nucleic acids are present on the same vector, whereas in other cases they are present on two or three separate vectors. The vectors may be viral or non-viral in nature. FIG. 25 provides an illustration of an embodiment of a vector for use in methods of the present disclosure (see also Mathison et al., J Thorac Cardiovasc Surg. 2014 Oct; 148(4): 1656-1664).

The vectors utilized in the embodiments of the disclosure may have one or more means for targeted delivery to cardiac tissue and/or targeted expression in certain cells. In some cases the vector(s) are provided to the individual with localized delivery to the heart, whereas in other cases the vectors are provided systemically to the individual with a means for targeted delivery to cardiac tissue and/or targeted expression in certain cells, such as cardiac fibroblasts, for example. In certain embodiments, the p63, p53, and/or p21 shRNA or siRNA and one or both of cardiac cell reprogramming factors (such as Hand2 and myocardin) polynucleotides are on the same molecule, although in some embodiments the p63, p53, and/or p21 shRNA or siRNA and one or both of cardiac cell reprogramming factors polynucleotides are on different molecules. When the shRNA and one or both of cardiac cell reprogramming factors are expressed from the same polynucleotide, they may have the same or different regulatory regions for their expression. In specific embodiments, the p63, p53, and/or p21-inactivating agent polynucleotides and one or more chromatin destabilizing agent polynucleotides are on the same or different molecules.

In particular embodiments, an expression vector for use in the disclosure may comprise one or more suitable restriction enzyme digestion sequences, start codons, stop codons, nuclear localization signals, protease cutting codons, selectable markers, origins of replication, regulatory regions, multiple cloning sites, and a combination thereof. Such moieties may be positioned in the expression vector in any suitable order.

A. Vectors

The term "vector" is used to refer to a carrier nucleic acid molecule into which a nucleic acid sequence can be inserted for introduction into a cell where it can be replicated. A nucleic acid sequence can be "exogenous," which means that it is foreign to the cell into which the vector is being introduced or that the sequence is homologous to a sequence in the cell but in a position within the host cell nucleic acid in which the sequence is ordinarily not found. Vectors include plasmids, cosmids, viruses (bacteriophage, animal viruses, and plant viruses), and artificial chromosomes (e.g., YACs). One of skill in the art would be well equipped to construct a vector through standard recombinant techniques (see, for example, Maniatis et al., 1988 and Ausubel et al., 1994, both incorporated herein by reference).

The term "expression vector" refers to any type of genetic construct comprising a nucleic acid coding for a RNA capable of being transcribed. In some cases, RNA molecules are then translated into a protein, polypeptide, or peptide. In other cases, these sequences are not translated, for example, in the production of antisense molecules or ribozymes. Expression vectors can contain a variety of "control sequences," which refer to nucleic acid sequences necessary for the transcription and possibly translation of an operably linked coding sequence in a particular host cell. In addition to control sequences that govern transcription and translation, vectors and expression vectors may contain nucleic acid sequences that serve other functions as well and are described infra.

1. Promoters and Enhancers

A "promoter" is a control sequence that is a region of a nucleic acid sequence at which initiation and rate of transcription are controlled. It may contain genetic elements at which regulatory proteins and molecules may bind, such as RNA polymerase and other transcription factors, to initiate the specific transcription a nucleic acid sequence. The phrases "operatively positioned," "operatively linked," "under control," and "under transcriptional control" mean that a promoter is in a correct functional location and/or orientation in relation to a nucleic acid sequence to control transcriptional initiation and/or expression of that sequence.

In embodiments of the disclosure, a CMV promoter or a tissue-specific promoter may be employed. The tissue-specific promoter may be a cardiac tissue specific promoter. Examples of cardiac tissue specific promoters include ventricle-specific myosin light chain-2 (mlc-2v); alpha-myosin heavy chain (α-MHC). In specific embodiments, a fibroblast-specific promoter is employed, such as Fsp1 promoter.

A promoter generally comprises a sequence that functions to position the start site for RNA synthesis. The best known example of this is the TATA box, but in some promoters lacking a TATA box, such as, for example, the promoter for the mammalian terminal deoxynucleotidyl transferase gene and the promoter for the SV40 late genes, a discrete element overlying the start site itself helps to fix the place of initiation. Additional promoter elements regulate the frequency of transcriptional initiation. Typically, these are located in the region 30-110 bp upstream of the start site, although a number of promoters have been shown to contain functional elements downstream of the start site as well. To bring a coding sequence "under the control of" a promoter, one positions the 5' end of the transcription initiation site of the transcriptional reading frame "downstream" of (i.e., 3' of) the chosen promoter. The "upstream" promoter stimulates transcription of the DNA and promotes expression of the encoded RNA.

The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either cooperatively or independently to activate transcription. A promoter may or may not be used in conjunction with an "enhancer," which refers to a cis-acting regulatory sequence involved in the transcriptional activation of a nucleic acid sequence.

A promoter may be one naturally associated with a nucleic acid sequence, as may be obtained by isolating the 5' non-coding sequences located upstream of the coding segment and/or exon. Such a promoter can be referred to as "endogenous." Similarly, an enhancer may be one naturally associated with a nucleic acid sequence, located either downstream or upstream of that sequence. Alternatively, certain advantages will be gained by positioning the coding nucleic acid segment under the control of a recombinant or heterologous promoter, which refers to a promoter that is not normally associated with a nucleic acid sequence in its natural environment. A recombinant or heterologous enhancer refers also to an enhancer not normally associated with a nucleic acid sequence in its natural environment. Such promoters or enhancers may include promoters or enhancers of other genes, and promoters or enhancers isolated from any other virus, or prokaryotic or eukaryotic cell, and promoters or enhancers not "naturally occurring," i.e., containing different elements of different transcriptional regulatory regions, and/or mutations that alter expression. For example, promoters that are most commonly used in recombinant DNA construction include the β-lactamase (penicillinase), lactose and tryptophan (trp) promoter systems. In addition to producing nucleic acid sequences of promoters and enhancers synthetically, sequences may be produced using recombinant cloning and/or nucleic acid amplification technology, including PCR™, in connection with the compositions disclosed herein (see U.S. Pat. Nos. 4,683,202 and 5,928,906, each incorporated herein by reference). Furthermore, it is contemplated the control sequences that direct transcription and/or expression of sequences within non-nuclear organelles such as mitochondria, chloroplasts, and the like, can be employed as well.

Naturally, it will be important to employ a promoter and/or enhancer that effectively directs the expression of the DNA segment in the organelle, cell type, tissue, organ, or organism chosen for expression. Those of skill in the art of molecular biology generally know the use of promoters, enhancers, and cell type combinations for protein expression, (see, for example Sambrook et al. 1989, incorporated herein by reference). The promoters employed may be constitutive, tissue-specific, inducible, and/or useful under the appropriate conditions to direct high level expression of the introduced DNA segment, such as is advantageous in the large-scale production of recombinant proteins and/or peptides. The promoter may be heterologous or endogenous.

Additionally any promoter/enhancer combination (as per, for example, the Eukaryotic Promoter Data Base EPDB, http://www.epd.isb-sib.ch/) could also be used to drive expression. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

2. Initiation Signals and Internal Ribosome Binding Sites

A specific initiation signal also may be required for efficient translation of coding sequences. These signals include the ATG initiation codon or adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

In certain embodiments of the disclosure, the use of internal ribosome entry sites (IRES) elements are used to create multigene, or polycistronic, messages. IRES elements are able to bypass the ribosome scanning model of 5' methylated Cap dependent translation and begin translation at internal sites (Pelletier and Sonenberg, 1988). IRES elements from two members of the picornavirus family (polio and encephalomyocarditis) have been described (Pelletier and Sonenberg, 1988), as well an IRES from a mammalian message (Macejak and Sarnow, 1991). IRES elements can be linked to heterologous open reading frames. Multiple open reading frames can be transcribed together, each separated by an IRES, creating polycistronic messages. By virtue of the IRES element, each open reading frame is accessible to ribosomes for efficient translation. Multiple genes can be efficiently expressed using a single promoter/enhancer to transcribe a single message (see U.S. Pat. Nos. 5,925,565 and 5,935,819, each herein incorporated by reference).

3. Multiple Cloning Sites

Vectors can include a multiple cloning site (MCS), which is a nucleic acid region that contains multiple restriction enzyme sites, any of which can be used in conjunction with standard recombinant technology to digest the vector (see, for example, Carbonelli et al., 1999, Levenson et al., 1998, and Cocea, 1997, incorporated herein by reference.) "Restriction enzyme digestion" refers to catalytic cleavage of a nucleic acid molecule with an enzyme that functions only at specific locations in a nucleic acid molecule. Many of these restriction enzymes are commercially available. Use of such enzymes is widely understood by those of skill in the art. Frequently, a vector is linearized or fragmented using a restriction enzyme that cuts within the MCS to enable exogenous sequences to be ligated to the vector. "Ligation" refers to the process of forming phosphodiester bonds between two nucleic acid fragments, which may or may not be contiguous with each other. Techniques involving restriction enzymes and ligation reactions are well known to those of skill in the art of recombinant technology.

4. Splicing Sites

Most transcribed eukaryotic RNA molecules will undergo RNA splicing to remove introns from the primary transcripts. Vectors containing genomic eukaryotic sequences may require donor and/or acceptor splicing sites to ensure proper processing of the transcript for protein expression (see, for example, Chandler et al., 1997, herein incorporated by reference.)

5. Termination Signals

The vectors or constructs of the present disclosure will generally comprise at least one termination signal. A "termination signal" or "terminator" is comprised of the DNA sequences involved in specific termination of an RNA transcript by an RNA polymerase. Thus, in certain embodiments a termination signal that ends the production of an RNA transcript is contemplated. A terminator may be necessary in vivo to achieve desirable message levels.

In eukaryotic systems, the terminator region may also comprise specific DNA sequences that permit site-specific cleavage of the new transcript so as to expose a polyadenylation site. This signals a specialized endogenous polymerase to add a stretch of about 200 A residues (polyA) to the 3' end of the transcript. RNA molecules modified with this polyA tail appear to more stable and are translated more efficiently. Thus, in other embodiments involving eukaryotes, it is preferred that that terminator comprises a signal for the cleavage of the RNA, and it is more preferred that the terminator signal promotes polyadenylation of the message. The terminator and/or polyadenylation site elements can serve to enhance message levels and to minimize read through from the cassette into other sequences.

Terminators contemplated for use in the disclosure include any known terminator of transcription described herein or known to one of ordinary skill in the art, including but not limited to, for example, the termination sequences of genes, such as for example the bovine growth hormone terminator or viral termination sequences, such as for example the SV40 terminator. In certain embodiments, the termination signal may be a lack of transcribable or translatable sequence, such as due to a sequence truncation.

6. Polyadenylation Signals

In expression, particularly eukaryotic expression, one will typically include a polyadenylation signal to effect proper polyadenylation of the transcript. The nature of the polyadenylation signal is not believed to be crucial to the successful practice of the disclosure, and any such sequence may be employed. Preferred embodiments include the SV40 polyadenylation signal or the bovine growth hormone polyadenylation signal, convenient and known to function well in various target cells. Polyadenylation may increase the stability of the transcript or may facilitate cytoplasmic transport.

7. Origins of Replication

In order to propagate a vector in a host cell, it may contain one or more origins of replication sites (often termed "ori"), which is a specific nucleic acid sequence at which replication is initiated. Alternatively an autonomously replicating sequence (ARS) can be employed if the host cell is yeast.

8. Selectable and Screenable Markers

In certain embodiments of the disclosure, cells containing a nucleic acid construct of the present disclosure may be identified in vitro or in vivo by including a marker in the expression vector. Such markers would confer an identifiable change to the cell permitting easy identification of cells containing the expression vector. Generally, a selectable marker is one that confers a property that allows for selection. A positive selectable marker is one in which the presence of the marker allows for its selection, while a negative selectable marker is one in which its presence prevents its selection. An example of a positive selectable marker is a drug resistance marker.

Usually the inclusion of a drug selection marker aids in the cloning and identification of transformants, for example, genes that confer resistance to neomycin, puromycin, hygromycin, DHFR, GPT, zeocin and histidinol are useful selectable markers. In addition to markers conferring a phenotype that allows for the discrimination of transformants based on the implementation of conditions, other types of markers including screenable markers such as GFP, whose basis is colorimetric analysis, are also contemplated. Alternatively, screenable enzymes such as herpes simplex virus thymidine kinase (tk) or chloramphenicol acetyltransferase (CAT) may be utilized. One of skill in the art would also know how to employ immunologic markers, possibly in conjunction with FACS analysis. The marker used is not believed to be important, so long as it is capable of being expressed simultaneously with the nucleic acid encoding a gene product. Further examples of selectable and screenable markers are well known to one of skill in the art.

B. Plasmid Vectors

In certain embodiments, a plasmid vector is contemplated for use to transform a host cell. In general, plasmid vectors containing replicon and control sequences which are derived from species compatible with the host cell are used in connection with these hosts. The vector ordinarily carries a replication site, as well as marking sequences which are capable of providing phenotypic selection in transformed cells. In a non-limiting example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, for example, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as, for example, *E. coli* LE392.

Genomic integrated plasmids, such as piggybac or sleeping beauty transposon gene delivery plasmids, may be employed for long term transgenic expression of a nucleic acid in heart or other organ.

Further useful plasmid vectors include pIN vectors (Inouye et al., 1985); and pGEX vectors, for use in generating glutathione S-transferase (GST) soluble fusion proteins for later purification and separation or cleavage. Other suitable fusion proteins are those with β-galactosidase, ubiquitin, and the like.

Bacterial host cells, for example, *E. coli*, comprising the expression vector, are grown in any of a number of suitable media, for example, LB. The expression of the recombinant protein in certain vectors may be induced, as would be understood by those of skill in the art, by contacting a host cell with an agent specific for certain promoters, e.g., by adding IPTG to the media or by switching incubation to a higher temperature. After culturing the bacteria for a further period, generally of between 2 and 24 h, the cells are collected by centrifugation and washed to remove residual media.

C. Viral Vectors

The ability of certain viruses to infect cells or enter cells via receptor-mediated endocytosis, and to integrate into host cell genome and express viral genes stably and efficiently have made them attractive candidates for the transfer of foreign nucleic acids into cells (e.g., mammalian cells). Non-limiting examples of virus vectors that may be used to deliver a nucleic acid of the present disclosure are described below.

1. Adenoviral Vectors

A particular method for delivery of the nucleic acid involves the use of an adenovirus expression vector. Although adenovirus vectors are known to have a low capacity for integration into genomic DNA, this feature is counterbalanced by the high efficiency of gene transfer afforded by these vectors. "Adenovirus expression vector" is meant to include those constructs containing adenovirus sequences sufficient to (a) support packaging of the construct and (b) to ultimately express a tissue or cell-specific construct that has been cloned therein. Knowledge of the genetic organization or adenovirus, a 36 kb, linear, double-stranded DNA virus, allows substitution of large pieces of adenoviral DNA with foreign sequences up to 7 kb (Grunhaus and Horwitz, 1992).

2. AAV Vectors

The nucleic acid may be introduced into the cell using adenovirus assisted transfection. Increased transfection efficiencies have been reported in cell systems using adenovirus coupled systems (Kelleher and Vos, 1994; Cotten et al., 1992; Curiel, 1994). Adeno-associated virus (AAV) is an attractive vector system for use in embodiments of the present disclosure as it has a high frequency of integration and it can infect nondividing cells, thus making it useful for delivery of genes into mammalian cells, for example, in tissue culture (Muzyczka, 1992) or in vivo. AAV has a broad host range for infectivity (Tratschin et al., 1984; Laughlin et al., 1986; Lebkowski et al., 1988; McLaughlin et al., 1988). Details concerning the generation and use of rAAV vectors are described in U.S. Pat. Nos. 5,139,941 and 4,797,368, each incorporated herein by reference.

3. Retroviral Vectors

Retroviruses have promise as delivery vectors due to their ability to integrate their genes into the host genome, transferring a large amount of foreign genetic material, infecting a broad spectrum of species and cell types and of being packaged in special cell-lines (Miller, 1992).

In order to construct a retroviral vector, a nucleic acid is inserted into the viral genome in the place of certain viral sequences to produce a virus that is replication-defective. In order to produce virions, a packaging cell line containing the gag, pol, and env genes but without the LTR and packaging components is constructed (Mann et al., 1983). When a recombinant plasmid containing a cDNA, together with the retroviral LTR and packaging sequences is introduced into a special cell line (e.g., by calcium phosphate precipitation for example), the packaging sequence allows the RNA transcript of the recombinant plasmid to be packaged into viral particles, which are then secreted into the culture media (Nicolas and Rubenstein, 1988; Temin, 1986; Mann et al., 1983). The media containing the recombinant retroviruses is then collected, optionally concentrated, and used for gene transfer. Retroviral vectors are able to infect a broad variety of cell types. However, integration and stable expression require the division of host cells (Paskind et al., 1975).

Lentiviruses are complex retroviruses, which, in addition to the common retroviral genes gag, pol, and env, contain other genes with regulatory or structural function. Lentiviral vectors are well known in the art (see, for example, Naldini et al., 1996; Zufferey et al., 1997; Blomer et al., 1997; U.S. Pat. Nos. 6,013,516 and 5,994,136). Some examples of lentivirus include the Human Immunodeficiency Viruses: HIV-1, HIV-2 and the Simian Immunodeficiency Virus: SIV. Lentiviral vectors have been generated by multiply attenuating the HIV virulence genes, for example, the genes env, vif, vpr, vpu and nef are deleted making the vector biologically safe.

Recombinant lentiviral vectors are capable of infecting non-dividing cells and can be used for both in vivo and ex vivo gene transfer and expression of nucleic acid sequences. For example, recombinant lentivirus capable of infecting a non-dividing cell wherein a suitable host cell is transfected with two or more vectors carrying the packaging functions, namely gag, pol and env, as well as rev and tat is described in U.S. Pat. No. 5,994,136, incorporated herein by reference. One may target the recombinant virus by linkage of the envelope protein with an antibody or a particular ligand for targeting to a receptor of a particular cell-type. By inserting a sequence (including a regulatory region) of interest into the viral vector, along with another gene which encodes the ligand for a receptor on a specific target cell, for example, the vector is now target-specific.

4. Other Viral Vectors

Other viral vectors may be employed as vaccine constructs in the present disclosure. Vectors derived from viruses such as vaccinia virus (Ridgeway, 1988; Baichwal and Sugden, 1986; Coupar et al., 1988), sindbis virus, cytomegalovirus and herpes simplex virus may be employed. They offer several attractive features for various mammalian cells (Friedmann, 1989; Ridgeway, 1988; Baichwal and Sugden, 1986; Coupar et al., 1988; Horwich et al., 1990).

D. Delivery Using Modified Viruses

A nucleic acid to be delivered may be housed within an infective virus that has been engineered to express a specific binding ligand. The virus particle will thus bind specifically to the cognate receptors of the target cell and deliver the contents to the cell. A novel approach designed to allow specific targeting of retrovirus vectors was developed based on the chemical modification of a retrovirus by the chemical addition of lactose residues to the viral envelope. This modification can permit the specific infection of hepatocytes via sialoglycoprotein receptors.

Another approach to targeting of recombinant retroviruses was designed in which biotinylated antibodies against a retroviral envelope protein and against a specific cell receptor were used. The antibodies were coupled via the biotin components by using streptavidin (Roux et al., 1989). Using antibodies against major histocompatibility complex class I and class II antigens, they demonstrated the infection of a variety of human cells that bore those surface antigens with an ecotropic virus in vitro (Roux et al., 1989).

E. Vector Delivery and Cell Transformation

Suitable methods for nucleic acid delivery for transformation of an organelle, a cell, a tissue or an organism for use with the current disclosure are believed to include virtually any method by which a nucleic acid (e.g., DNA) can be introduced into an organelle, a cell, a tissue or an organism, as described herein or as would be known to one of ordinary skill in the art. Such methods include, but are not limited to, direct delivery of DNA such as by ex vivo transfection (Wilson et al., 1989, Nabel et al, 1989), by injection (U.S. Pat. Nos. 5,994,624, 5,981,274, 5,945,100, 5,780,448, 5,736,524, 5,702,932, 5,656,610, 5,589,466 and 5,580,859, each incorporated herein by reference), including microinjection (Harlan and Weintraub, 1985; U.S. Pat. No. 5,789,215, incorporated herein by reference); by electroporation (U.S. Pat. No. 5,384,253, incorporated herein by reference; Tur-Kaspa et al., 1986; Potter et al., 1984); by calcium phosphate precipitation (Graham and Van Der Eb, 1973; Chen and Okayama, 1987; Rippe et al., 1990); by using DEAE-dextran followed by polyethylene glycol (Gopal, 1985); by direct sonic loading (Fechheimer et al., 1987); by liposome mediated transfection (Nicolau and Sene, 1982; Fraley et al., 1979; Nicolau et al., 1987; Wong et al., 1980; Kaneda et al., 1989; Kato et al., 1991) and receptor-mediated transfection (Wu and Wu, 1987; Wu and Wu, 1988); by microprojectile bombardment (PCT Application Nos. WO 94/09699 and 95/06128; U.S. Pat. Nos. 5,610,042; 5,322,783 5,563,055, 5,550,318, 5,538,877 and 5,538,880, and each incorporated herein by reference); by agitation with silicon carbide fibers (Kaeppler et al., 1990; U.S. Pat. Nos. 5,302,523 and 5,464,765, each incorporated herein by reference); by Agrobacterium-mediated transformation (U.S. Pat. Nos. 5,591,616 and 5,563,055, each incorporated herein by reference); by PEG-mediated transformation of protoplasts (Omirulleh et al., 1993; U.S. Pat. Nos. 4,684,611 and 4,952,500, each incorporated herein by reference); by desiccation/inhibition-mediated DNA uptake (Potrykus et al., 1985), and any combination of such methods. Through the application of techniques such as these, organelle(s), cell(s), tissue(s) or organism(s) may be stably or transiently transformed.

1. Ex vivo Transformation

Methods for transfecting vascular cells and tissues removed from an organism in an ex vivo setting are known to those of skill in the art. For example, canine endothelial cells have been genetically altered by retroviral gene transfer in vitro and transplanted into a canine (Wilson et al., 1989). In another example, yucatan minipig endothelial cells were tranfected by retrovirus in vitro and transplanted into an artery using a double-balloon catheter (Nabel et al., 1989). Thus, it is contemplated that cells or tissues may be removed and tranfected ex vivo using the nucleic acids of the present disclosure. In particular aspects, the transplanted cells or tissues may be placed into an organism. In preferred facets, a nucleic acid is expressed in the transplanted cells or tissues.

2. Injection

In certain embodiments, a nucleic acid may be delivered to an organelle, a cell, a tissue or an organism via one or more injections (i.e., a needle injection), such as, for example, subcutaneously, intradermally, intramuscularly, intervenously, intraperitoneally, etc. Methods of injection are well known to those of ordinary skill in the art (e.g., injection of a composition comprising a saline solution). Further embodiments of the present disclosure include the introduction of a nucleic acid by direct microinjection.

3. Electroporation

In certain embodiments of the present disclosure, a nucleic acid is introduced into an organelle, a cell, a tissue or an organism via electroporation. Electroporation involves the exposure of a suspension of cells and DNA to a high-voltage electric discharge. In some variants of this method, certain cell wall-degrading enzymes, such as pectin-degrading enzymes, are employed to render the target recipient cells more susceptible to transformation by electroporation than untreated cells (U.S. Pat. No. 5,384,253, incorporated herein by reference). Alternatively, recipient cells can be made more susceptible to transformation by mechanical wounding.

Transfection of eukaryotic cells using electroporation has been quite successful. Mouse pre-B lymphocytes have been transfected with human kappa-immunoglobulin genes (Potter et al., 1984), and rat hepatocytes have been transfected with the chloramphenicol acetyltransferase gene (Tur-Kaspa et al., 1986) in this manner.

To effect transformation by electroporation in cells such as, for example, plant cells, one may employ either friable tissues, such as a suspension culture of cells or embryogenic callus or alternatively one may transform immature embryos or other organized tissue directly. In this technique, one would partially degrade the cell walls of the chosen cells by exposing them to pectin-degrading enzymes (pectolyases) or mechanically wounding in a controlled manner Examples of some species which have been transformed by electroporation of intact cells include maize (U.S. Pat. No. 5,384,253; Rhodes et al., 1995; D'Halluin et al., 1992), wheat (Zhou et al., 1993), tomato (Hou and Lin, 1996), soybean (Christou et al., 1987) and tobacco (Lee et al., 1989).

One also may employ protoplasts for electroporation transformation of plant cells (Bates, 1994; Lazzeri, 1995). For example, the generation of transgenic soybean plants by electroporation of cotyledon-derived protoplasts is described by Dhir and Widholm in International Patent Application No. WO 9217598, incorporated herein by reference. Other examples of species for which protoplast transformation has been described include barley (Lazerri, 1995), sorghum (Battraw et al., 1991), maize (Bhattacharjee et al., 1997), wheat (He et al., 1994) and tomato (Tsukada, 1989).

4. Calcium Phosphate

In other embodiments of the present disclosure, a nucleic acid is introduced to the cells using calcium phosphate precipitation. Human KB cells have been transfected with adenovirus 5 DNA (Graham and Van Der Eb, 1973) using this technique. Also in this manner, mouse L(A9), mouse C127, CHO, CV-1, BHK, NIH3T3 and HeLa cells were transfected with a neomycin marker gene (Chen and Okayama, 1987), and rat hepatocytes were transfected with a variety of marker genes (Rippe et al., 1990).

5. DEAE-Dextran

In another embodiment, a nucleic acid is delivered into a cell using DEAE-dextran followed by polyethylene glycol. In this manner, reporter plasmids were introduced into mouse myeloma and erythroleukemia cells (Gopal, 1985).

6. Sonication Loading

Additional embodiments of the present disclosure include the introduction of a nucleic acid by direct sonic loading. LTK-fibroblasts have been transfected with the thymidine kinase gene by sonication loading (Fechheimer et al., 1987).

7. Liposome-Mediated Transfection

In a further embodiment of the disclosure, a nucleic acid may be entrapped in a lipid complex such as, for example, a liposome. Liposomes are vesicular structures characterized by a phospholipid bilayer membrane and an inner aqueous medium. Multilamellar liposomes have multiple lipid layers separated by aqueous medium. They form spontaneously when phospholipids are suspended in an excess of aqueous solution. The lipid components undergo self-rearrangement before the formation of closed structures and entrap water and dissolved solutes between the lipid bilayers (Ghosh and Bachhawat, 1991). Also contemplated is an nucleic acid complexed with Lipofectamine (Gibco BRL) or Superfect (Qiagen).

Liposome-mediated nucleic acid delivery and expression of foreign DNA in vitro has been very successful (Nicolau and Sene, 1982; Fraley et al., 1979; Nicolau et al., 1987). The feasibility of liposome-mediated delivery and expression of foreign DNA in cultured chick embryo, HeLa and hepatoma cells has also been demonstrated (Wong et al., 1980).

In certain embodiments of the disclosure, a liposome may be complexed with a hemagglutinating virus (HVJ). This has been shown to facilitate fusion with the cell membrane and promote cell entry of liposome-encapsulated DNA (Kaneda et al., 1989). In other embodiments, a liposome may be complexed or employed in conjunction with nuclear non-histone chromosomal proteins (HMG-1) (Kato et al., 1991). In yet further embodiments, a liposome may be complexed or employed in conjunction with both HVJ and HMG-1. In other embodiments, a delivery vehicle may comprise a ligand and a liposome.

8. Receptor Mediated Transfection

Still further, a nucleic acid may be delivered to a target cell via receptor-mediated delivery vehicles. These take advantage of the selective uptake of macromolecules by receptor-mediated endocytosis that will be occurring in a target cell. In view of the cell type-specific distribution of various receptors, this delivery method adds another degree of specificity to the present disclosure.

Certain receptor-mediated gene targeting vehicles comprise a cell receptor-specific ligand and a nucleic acid-binding agent. Others comprise a cell receptor-specific ligand to which the nucleic acid to be delivered has been operatively attached. Several ligands have been used for receptor-mediated gene transfer (Wu and Wu, 1987; Wagner et al., 1990; Perales et al., 1994; Myers, EPO 0273085), which establishes the operability of the technique. Specific delivery in the context of another mammalian cell type has been described (Wu and Wu, 1993; incorporated herein by reference). In certain aspects of the present disclosure, a ligand will be chosen to correspond to a receptor specifically expressed on the target cell population.

In other embodiments, a nucleic acid delivery vehicle component of a cell-specific nucleic acid targeting vehicle may comprise a specific binding ligand in combination with a liposome. The nucleic acid(s) to be delivered are housed within the liposome and the specific binding ligand is functionally incorporated into the liposome membrane. The liposome will thus specifically bind to the receptor(s) of a target cell and deliver the contents to a cell.

In still further embodiments, the nucleic acid delivery vehicle component of a targeted delivery vehicle may be a liposome itself, which will preferably comprise one or more lipids or glycoproteins that direct cell-specific binding. For example, lactosyl-ceramide, a galactose-terminal asialganglioside, have been incorporated into liposomes and observed an increase in the uptake of the insulin gene by hepatocytes (Nicolau et al., 1987). It is contemplated that the tissue-specific transforming constructs of the present disclosure can be specifically delivered into a target cell in a similar manner 9. Microprojectile Bombardment Microprojectile bombardment techniques can be used to introduce a nucleic acid into at least one, organelle, cell, tissue or organism (U.S. Pat. Nos. 5,550,318; 5,538,880; 5,610,042; and PCT Application WO 94/09699; each of which is incorporated herein by reference). This method depends on the ability to accelerate DNA-coated microprojectiles to a high velocity allowing them to pierce cell membranes and enter cells without killing them (Klein et al., 1987). There are a wide variety of microprojectile bombardment techniques known in the art, many of which are applicable to the disclosure.

Microprojectile bombardment may be used to transform various cell(s), tissue(s) or organism(s), such as for example any plant species. Examples of species which have been transformed by microprojectile bombardment include monocot species such as maize (PCT Application WO 95/06128), barley (Ritala et al., 1994; Hensgens et al., 1993), wheat (U.S. Pat. No. 5,563,055, incorporated herein by reference), rice (Hensgens et al., 1993), oat (Torbet et al., 1995; Torbet et al., 1998), rye (Hensgens et al., 1993), sugarcane (Bower et al., 1992), and sorghum (Casas et al., 1993; Hagio et al., 1991); as well as a number of dicots including tobacco (Tomes et al., 1990; Buising and Benbow, 1994), soybean (U.S. Pat. No. 5,322,783, incorporated herein by reference), sunflower (Knittel et al. 1994), peanut (Singsit et al., 1997), cotton (McCabe and Martinell, 1993), tomato (VanEck et al. 1995), and legumes in general (U.S. Pat. No. 5,563,055, incorporated herein by reference).

In this microprojectile bombardment, one or more particles may be coated with at least one nucleic acid and delivered into cells by a propelling force. Several devices for accelerating small particles have been developed. One such device relies on a high voltage discharge to generate an electrical current, which in turn provides the motive force (Yang et al., 1990). The microprojectiles used have consisted of biologically inert substances such as tungsten or gold particles or beads. Exemplary particles include those comprised of tungsten, platinum, and preferably, gold. It is contemplated that in some instances DNA precipitation onto metal particles would not be necessary for DNA delivery to a recipient cell using microprojectile bombardment. However, it is contemplated that particles may contain DNA rather than be coated with DNA. DNA-coated particles may increase the level of DNA delivery via particle bombardment but are not, in and of themselves, necessary.

For the bombardment, cells in suspension are concentrated on filters or solid culture medium. Alternatively, immature embryos or other target cells may be arranged on solid culture medium. The cells to be bombarded are positioned at an appropriate distance below the macroprojectile stopping plate.

An illustrative embodiment of a method for delivering DNA into a cell (e.g., a plant cell) by acceleration is the Biolistics Particle Delivery System, which can be used to propel particles coated with DNA or cells through a screen, such as a stainless steel or Nytex screen, onto a filter surface covered with cells, such as for example, a monocot plant cells cultured in suspension. The screen disperses the particles so that they are not delivered to the recipient cells in large aggregates. It is believed that a screen intervening between the projectile apparatus and the cells to be bombarded reduces the size of projectiles aggregate and may contribute to a higher frequency of transformation by reducing the damage inflicted on the recipient cells by projectiles that are too large.

V. Proteins, Polypeptides, and Peptides

In some cases, embodiments may utilize one or more purified cardiac cell programming factors, such as Hand2, myocardin, Gata4, Mef2c, or Tbx5 proteins, polypeptides, or peptides, or one or more chromating destabilizing agent proteins, polypeptides, or peptides, or other proteins, polypeptides, or peptides, and this may be done in addition to or alternative to utilizing the respective nucleic acid form. The term "purified proteins, polypeptides, or peptides" as used herein, is intended to refer to an proteinaceous composition, isolatable from mammalian cells or recombinant host cells, wherein the at least one protein, polypeptide, or peptide is purified to any degree relative to its naturally-obtainable state, i.e., relative to its purity within a cellular extract. A purified protein, polypeptide, or peptide therefore also refers to a wild-type or mutant protein, polypeptide, or peptide free from the environment in which it naturally occurs.

The nucleotide and protein, polypeptide and peptide sequences for various genes have been previously disclosed, and may be found at computerized databases known to those of ordinary skill in the art. One such database is the National Center for Biotechnology Information's GenBank® and GenPept® databases. The coding regions for these known genes may be amplified and/or expressed using the techniques disclosed herein or by any technique that would be known to those of ordinary skill in the art. Additionally, peptide sequences may be synthesized by methods known to those of ordinary skill in the art, such as peptide synthesis using automated peptide synthesis machines, such as those available from Applied Biosystems (Foster City, CA).

Generally, "purified" will refer to a specific protein, polypeptide, or peptide composition that has been subjected to fractionation to remove various other proteins, polypeptides, or peptides, and which composition substantially retains its activity, as may be assessed, for example, by the protein assays, as described herein below, or as would be known to one of ordinary skill in the art for the desired protein, polypeptide or peptide.

Where the term "substantially purified" is used, this will refer to a composition in which the specific protein, polypeptide, or peptide forms the major component of the composition, such as constituting about 50% of the proteins in the composition or more. In preferred embodiments, a substantially purified protein will constitute more than 60%, 70%, 80%, 90%, 95%, 99% or even more of the proteins in the composition.

A peptide, polypeptide or protein that is "purified to homogeneity," as applied to the present disclosure, means that the peptide, polypeptide or protein has a level of purity where the peptide, polypeptide or protein is substantially free from other proteins and biological components. For example, a purified peptide, polypeptide or protein will often be sufficiently free of other protein components so that degradative sequencing may be performed successfully.

Various methods for quantifying the degree of purification of proteins, polypeptides, or peptides will be known to those of skill in the art in light of the present disclosure. These include, for example, determining the specific protein activity of a fraction, or assessing the number of polypeptides within a fraction by gel electrophoresis.

To purify a desired protein, polypeptide, or peptide a natural or recombinant composition comprising at least some specific proteins, polypeptides, or peptides will be subjected to fractionation to remove various other components from the composition. In addition to those techniques described in detail herein below, various other techniques suitable for use in protein purification will be well known to those of skill in the art. These include, for example, precipitation with ammonium sulfate, PEG, antibodies and the like or by heat denaturation, followed by centrifugation; chromatography steps such as ion exchange, gel filtration, reverse phase, hydroxylapatite, lectin affinity and other affinity chromatography steps; isoelectric focusing; gel electrophoresis; and combinations of such and other techniques.

Another example is the purification of a specific fusion protein using a specific binding partner. Such purification methods are routine in the art. As the present disclosure provides DNA sequences for the specific proteins, any fusion protein purification method can now be practiced. This is exemplified by the generation of an specific protein-glutathione S-transferase fusion protein, expression in *E. coli*, and isolation to homogeneity using affinity chromatography on glutathione-agarose or the generation of a polyhistidine tag on the N- or C-terminus of the protein, and subsequent purification using Ni-affinity chromatography. However, given many DNA and proteins are known, or may be identified and amplified using the methods described herein, any purification method can now be employed.

Although preferred for use in certain embodiments, there is no general requirement that the protein, polypeptide, or peptide always be provided in their most purified state. Indeed, it is contemplated that less substantially purified protein, polypeptide or peptide, which are nonetheless enriched in the desired protein compositions, relative to the natural state, will have utility in certain embodiments.

Methods exhibiting a lower degree of relative purification may have advantages in total recovery of protein product, or in maintaining the activity of an expressed protein. Inactive products also have utility in certain embodiments, such as, e.g., in determining antigenicity via antibody generation.

VI. Host Cells

Although in some embodiments the nucleic acids of the disclosure are provided directly to cardiac tissue and are uptaken by cells in the tissue, in some embodiments the nucleic acids are first generated and manipulated in cells ex vivo, such as by employing routine recombinant technology methods.

As used herein, the terms "cell," "cell line," and "cell culture" may be used interchangeably. All of these terms also include their progeny, which is any and all subsequent generations. It is understood that all progeny may not be identical due to deliberate or inadvertent mutations. In the context of expressing a heterologous nucleic acid sequence, "host cell" refers to a prokaryotic or eukaryotic cell, and it includes any transformable organism that is capable of replicating a vector and/or expressing a heterologous gene encoded by a vector. A host cell can, and has been, used as a recipient for vectors. A host cell may be "transfected" or "transformed," which refers to a process by which exogenous nucleic acid is transferred or introduced into the host cell. A transformed cell includes the primary subject cell and its progeny. As used herein, the terms "engineered" and "recombinant" cells or host cells are intended to refer to a cell into which an exogenous nucleic acid sequence, such as, for example, a vector, has been introduced. Therefore, recombinant cells are distinguishable from naturally occurring cells which do not contain a recombinantly introduced nucleic acid.

In certain embodiments, it is contemplated that RNAs or proteinaceous sequences may be co-expressed with other selected RNAs or proteinaceous sequences in the same host cell. Co-expression may be achieved by co-transfecting the host cell with two or more distinct recombinant vectors. Alternatively, a single recombinant vector may be constructed to include multiple distinct coding regions for RNAs or DNAs (as an active agent) or polypeptides (as an active agent), which could then be expressed in host cells transfected with the single vector.

A tissue may comprise a host cell or cells to be transformed with a polynucleotide encoding part or all of p63, p53, and/or p21 shRNA or siRNA, one or more cardiac cell reprogramming factors, and/or one or more chromatin destabilizing agents. In specific embodiments, a cell may harbor a polynucleotide encoding part or all of p63 shRNA, Hand2, and/or myocardin. The tissue may be part or separated from an organism. In certain embodiments, a tissue may comprise, but is not limited to, myocytes, adipocytes, alveolar, ameloblasts, axon, basal cells, blood (e.g., lymphocytes), blood vessel, bone, bone marrow, brain, breast, cardiac, cartilage, cervix, colon, cornea, embryonic, endometrium, endothelial, epithelial, esophagus, facia, fibroblast, follicular, ganglion cells, glial cells, goblet cells, kidney, liver, lung, lymph node, muscle, neuron, ovaries, pancreas, peripheral blood, prostate, skin, skin, small intestine, spleen, stem cells, stomach, testes, and so forth.

In certain embodiments, the host cell or tissue may be comprised in at least one organism. In certain embodiments, the organism may be, but is not limited to, a prokayote (e.g., a eubacteria, an archaea) or an eukaryote, as would be understood by one of ordinary skill in the art (see, for example, webpage http://phylogeny.arizona.edu/tree/phylogeny.html).

Numerous cell lines and cultures are available for use as a host cell, and they can be obtained through the American Type Culture Collection (ATCC), which is an organization that serves as an archive for living cultures and genetic materials (www.atcc.org). An appropriate host can be determined by one of skill in the art based on the vector backbone and the desired result. A plasmid or cosmid, for example, can be introduced into a prokaryote host cell for replication of many vectors. Cell types available for vector replication and/or expressioninclude, but are not limited to, bacteria, such as *E. coli* (e.g., *E. coli* strain RR1, *E. coli* LE392, *E. coli* B, *E. coli* X 1776 (ATCC No. 31537) as well as *E. coli* W3110 (F-, lambda-, prototrophic, ATCC No. 273325), DH5α, JM109, and KCB, bacilli such as *Bacillus subtilis*; and other enterobacteriaceae such as *Salmonella typhimurium, Serratia marcescens*, various *Pseudomonas* species, as well as a number of commercially available bacterial hosts such as SURE® Competent Cells and Solopack™ Gold Cells (Stratagene®, La Jolla). In certain embodiments, bacterial cells such as *E. coli* LE392 are particularly contemplated as host cells for phage viruses.

Examples of eukaryotic host cells for replication and/or expression of a vector include, but are not limited to, HeLa, NIH3T3, Jurkat, 293, Cos, CHO, Saos, and PC12. Many host cells from various cell types and organisms are available and would be known to one of skill in the art. Similarly, a viral vector may be used in conjunction with either a eukaryotic or prokaryotic host cell, particularly one that is permissive for replication or expression of the vector.

Some vectors may employ control sequences that allow it to be replicated and/or expressed in both prokaryotic and eukaryotic cells. One of skill in the art would further understand the conditions under which to incubate all of the above described host cells to maintain them and to permit replication of a vector. Also understood and known are techniques and conditions that would allow large-scale production of vectors, as well as production of the nucleic acids encoded by vectors and their cognate polypeptides, proteins, or peptides.

VII. Combination Therapy

In certain cases, the therapy of the present disclosure is utilized in conjunction with one or more other therapies for a cardiac medical condition. p63, p53, and/or p21-inactivating agents may be used in conjunction with one or more cardiac cell reprogramming factors and/or in conjunction with one or more chromatin destabilizing agents and/or with one or more anti-fibrotic agents or angiogenic factors. In specific embodiments, p63 shRNA or siRNA is used in combination with Hand2 and or myocardin gene therapy, although it may also be used in combination with other genes or gene products, including, Gata4, Mef2c, Tbx5, miR-133, miR-1, Oct4, Klf4, c-myc, Sox2, Mesp1, Brachyury, Nkx2.5, ETS2, ESRRG, Mrtf-A, MyoD, and/or ZFPM2 (in nucleic acid or polypeptide or peptide form, in specific embodiments). The one or more other therapies may be directly or indirectly related to the cardiac medical condition (examples of indirectly related therapies include those for pain or infection). In specific embodiments, the additional therapy related to the cardiac medical condition is drug therapy, surgery, ventricular assisted device(VAD) implantation, video assisted thoracotomy (VAT), coronary bypass, or a combination thereof.

In specific embodiments, one or more agents that prevent fibrosis and/or enhance or promote angiogenesis may be used as adjuncts to embodiments of the disclosure. They may be provided to an individual in a localized region of the heart, including a region that has tissue damage, loss of cardiomyocyte, scar tissue, and so forth, or they may be provided systemically. The one or more agents may be any composition suitable to facilitate angiogenesis in the desired region. In specific embodiments, the agent may be a protein, peptide, small molecule, nucleic acid, and so forth. Embodiments such as those described in US2003/0103943 or US2001/0041679 may be employed in conjunction with the methods of the disclosure. Specific embodiments include fibroblast growth factor (FGF); vascular endothelial growth factor (VEGF); angiopoietins, Ang1 and Ang2; matrix metalloproteinase (MMP); Delta-like ligand 4 (Dll4); or peptides thereof; or combinations thereof. ITD-1 is a small molecule that inhibits TGF-beta and thus, fibrosis and cardiac remodeling (Willems E, Cabral-Teixeira J, Schade D, et al. Cell Stem Cell. 2012. pp. 242-252.), and it may be utilized.

The agent that enhances angiogenesis may be referred to as an angiogenic factor. The agent may be provided to the individual prior to the individual receiving the agent that partially or completely downregulates or inactivates p63, p53, and/or 21 and/or prior to the cardiac cell reprogramming factor and/or prior to the chromatin destabilizing agent.

The therapy of the present disclosure may precede or follow the other agent treatment by intervals ranging from minutes to hours to days to weeks or months. In embodiments where the other agent and the instant therapy are applied separately to the individual, one would generally ensure that a significant period of time did not expire between the time of each delivery, such that the therapy of the disclosure and the additional therapy would still be able to exert an advantageously combined effect on the individual. In such instances, it is contemplated that one may contact the individual with both modalities simultaneously or within minutes of each other or within about 1-12, 6-12, or 12-24 h of each other. In some situations, it may be desirable to extend the time period for treatment significantly, however, where several days (2, 3, 4, 5, 6 or 7) to several weeks (1, 2, 3, 4, 5, 6, 7 or 8) lapse between the respective administrations.

In specific embodiments, the therapy of the present disclosure and the additional therapy are provided at the same time or at different times. The separate entities may be within the same compositions or they may be comprised in separate compositions. In cases wherein the therapy of the present disclosure and the second therapy are provided at different times, they may be separated by any suitable range in times, such as minutes, hours, days, or weeks. In embodiments wherein they are provided separately, the order of delivery of two (or more) therapies may be of any suitable order, including delivery of p63shRNA with Hand2 and/or myocardin prior to or subsequent to another therapy.

Examples of other treatments to be employed with the therapy of the disclosure includes one or more of the following: ACE Inhibitors, Aldosterone Inhibitor, Angiotensin II Receptor Blocker (ARBs); Beta-Blockers, Calcium Channel Blockers, Cholesterol-Lowering Drugs, Digoxin, Diuretics, Inotropic Therapy, Potassium or Magnesium, Vasodilators, anticoagulant medication, aspirin, surgery, VAD implantation, VAT, coronary bypass, percutaneous coronary intervention (PCI) or a combination thereof.

VIII. Kits of the Disclosure

Any of the compositions described herein may be comprised in a kit. In a non-limiting example, a p63, p53, and/or p21-inactivating agent (such as a siRNA or shRNA), one or more cardiac cell reprogramming factors, and/or one or more chromatin destabilizing agents or other polynucleotide or primers for amplification of same may be comprised in a kit. In specific embodiments, the kit comprises p63 shRNA with or without Hand2 and/or myocardin polypeptides or peptides. The kit may additionally comprise additional agents for therapy of a cardiac medical condition.

The components of the kits may be packaged either in aqueous media or in lyophilized form. The container means of the kits will generally include at least one vial, test tube, flask, bottle, syringe or other container means, into which a component may be placed, and preferably, suitably aliquoted. Where there are more than one component in the kit, the kit also will generally contain a second, third or other additional container into which the additional components may be separately placed. However, various combinations of components may be comprised in a vial. The kits of the present disclosure also will typically include a means for containing the one or more compositions in close confinement for commercial sale. Such containers may include injection or blow-molded plastic containers into which the desired vials are retained.

The composition may be formulated into a syringeable composition. In which case, the container means may itself be a syringe, pipette, and/or other such like apparatus, from which the formulation may be applied to an infected area of the body, injected into an animal, and/or even applied to and/or mixed with the other components of the kit. However, the components of the kit may be provided as dried powder(s). When reagents and/or components are provided as a dry powder, the powder can be reconstituted by the addition of a suitable solvent. It is envisioned that the solvent may also be provided in another container means.

The kits of the present disclosure will also typically include a means for containing the vials in close confinement for commercial sale, such as, e.g., injection and/or blow-molded plastic containers into which the desired vials are retained.

In particular embodiments, the kit comprises reagents and/or tools for determining that an individual has a cardiac medical condition. In some embodiments, the kit comprises one or more additional therapies for a cardiac-related medical condition, such as one or more of ACE Inhibitor, aldosterone inhibitor, angiotensin II receptor blocker (ARBs); beta-blocker, calcium channel blocker, cholesterol-lowering drug, digoxin, diuretics, inotropic therapy, potassium, magnesium, vasodilator, anticoagulant medication, aspirin, TGF-beta inhibitor, and a combination thereof. In specific embodiments, an individual receives angiogenic therapy before, during, or after the therapy of the present disclosure. Examples of angiogenic therapies include fibroblast growth factor (FGF); vascular endothelial growth factor (VEGF); angiopoietins, Ang1 and Ang2; matrix metalloproteinase (MMP); Delta-like ligand 4 (Dll4); or peptides thereof; or combinations thereof.

EXAMPLES

The following examples are included to demonstrate preferred embodiments of the disclosure. It should be appreciated by those of skill in the art that the techniques disclosed in the examples which follow present techniques discovered by the inventors to function well in the practice of the disclosure, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the disclosure.

Example 1

P63 Inactivation Increases the Transdifferentiation Efficiency of Fibroblasts into Cardiomyocytes Cellular regenerative therapy has emerged as a treatment for a number of degenerative diseases, most notably ischemic heart disease, which is the number one cause of death in the world. Several strategies have been proposed, including transdifferentiation and the formation of induced pluripotent stem cells. Transdifferentiation has been attempted with transcription factors such as Gata4, Mef2c and Tbx5 (GMT), while iPS cells may be formed using the Yamanaka factors (Oct4, Sox2, Klf4, c-myc) or knocking down genes involved in regulating the cell cycle, such as p53.

While it has been reported that murine cells that are p63 deficient display a high degree of plasticity, no distinct strategy has been developed for their application in ischemic heart disease. Specifically, it has not been described how the p63 deficient cells may be "driven" down the cardiomyocyte lineage. The attached slides show FACS (fluorescence activated cell sorting) data confirming that 76% of p63 deficient murine embryonic fibroblasts exposed to factors Hand2 and Myocardin express cTnT (Cardiac Troponin T), a highly specific marker for the cardiomyocyte lineage. Without Hand2 and Myocardin, approximately 30-40% of p63−/− cells express cTnT while the remainder of cells may have the potential to become other types of cells, which is not ideal as a therapy. The strategy is unique because it selects for the formation of induced cardiomyocytes over other lineages. Neither this strategy (inactivation of the p63 gene with the addition of Hand2 and Myocardin) nor this high of an efficiency has been reported in the literature. Approaches of the disclosure are useful clinical therapies for heart failure.

The p63 gene, a family member of the p53 gene, plays an important role in cell cycle regulation, "stemness," senescence, and differentiation. Wild type and p63−/−mouse embryonic fibroblasts (MEF's) with and without exposure to lentiviral GMT (Gata4, Mef2c, Tbx5) were analyzed by flow cytometry for cTnT (marker of cardiomyocyte lineage) at 22 days.

Figure 2:
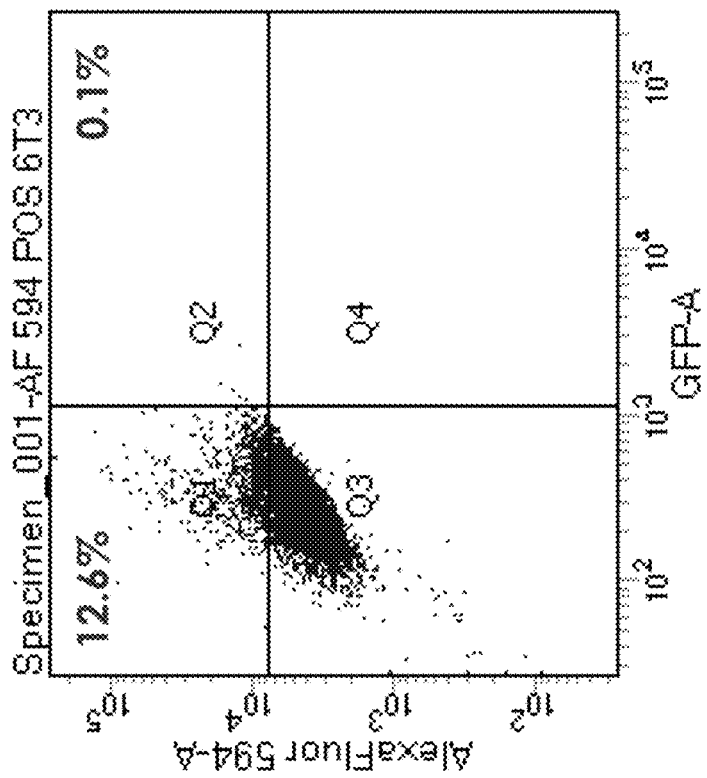
FIG. 2 shows fluorescence activated cell sorting (FACS) analysis of a positive control comprising neonatal rat cardiomyoblasts.
Figure 3:
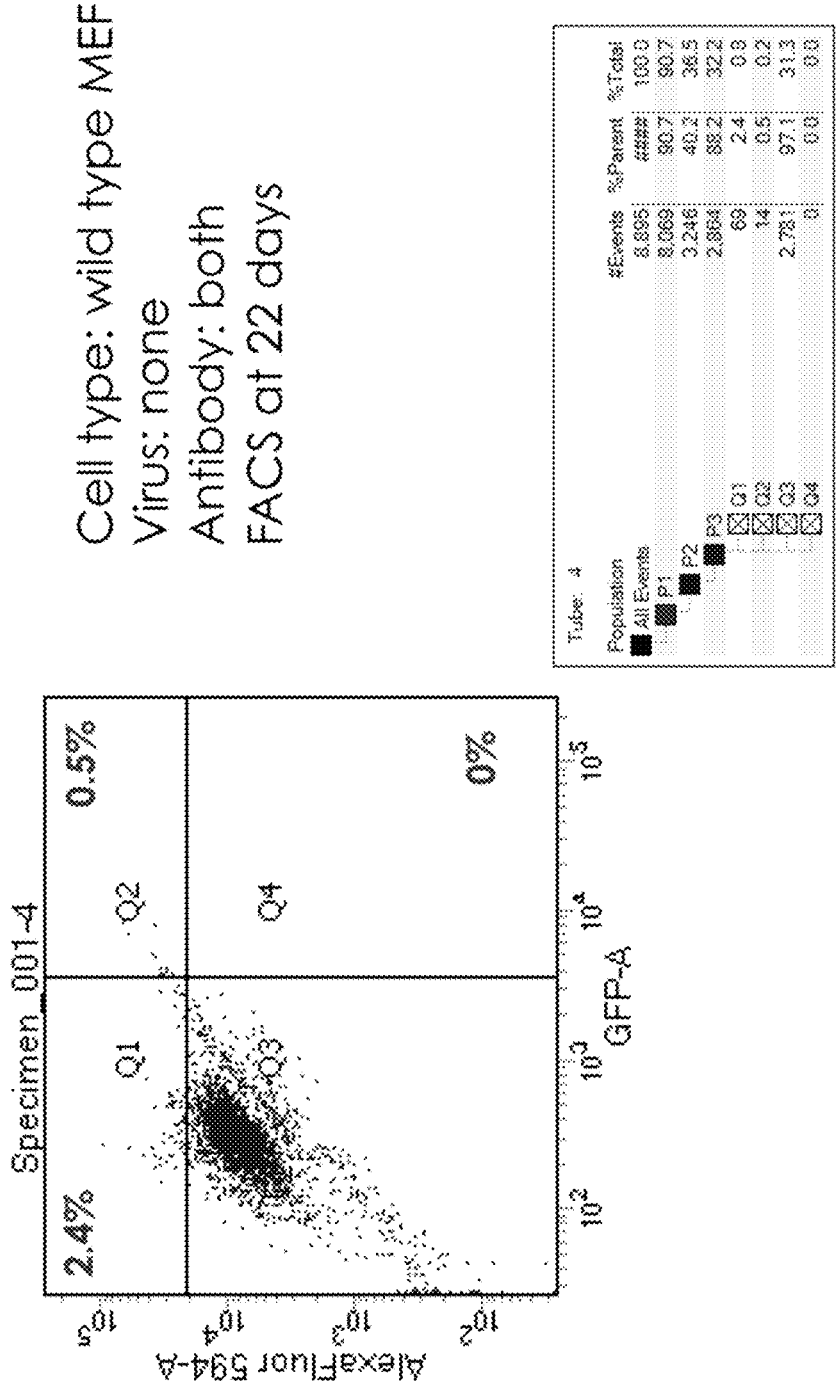
FIG. 3 demonstrates a negative control using wild-type cells given no virus.
Figure 4:
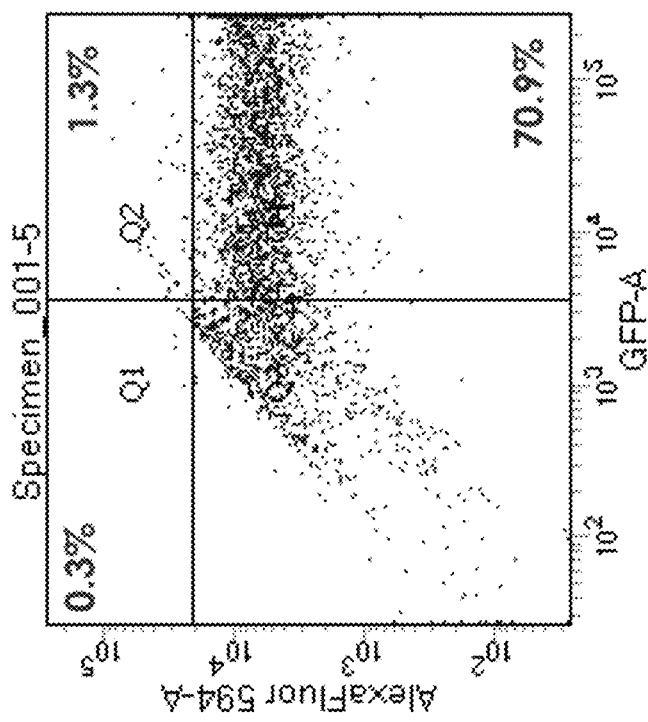
FIG. 4 shows wild-type cells that are exposed to GFP.
Figure 4:
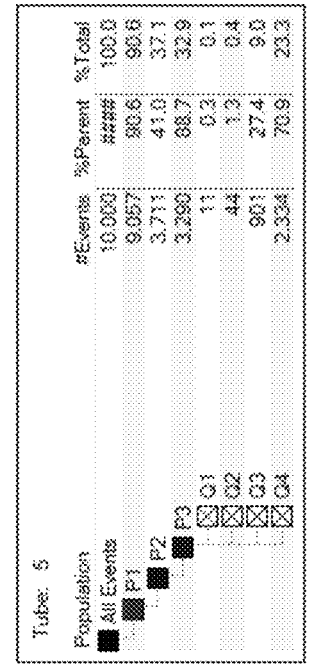
Figure 5:
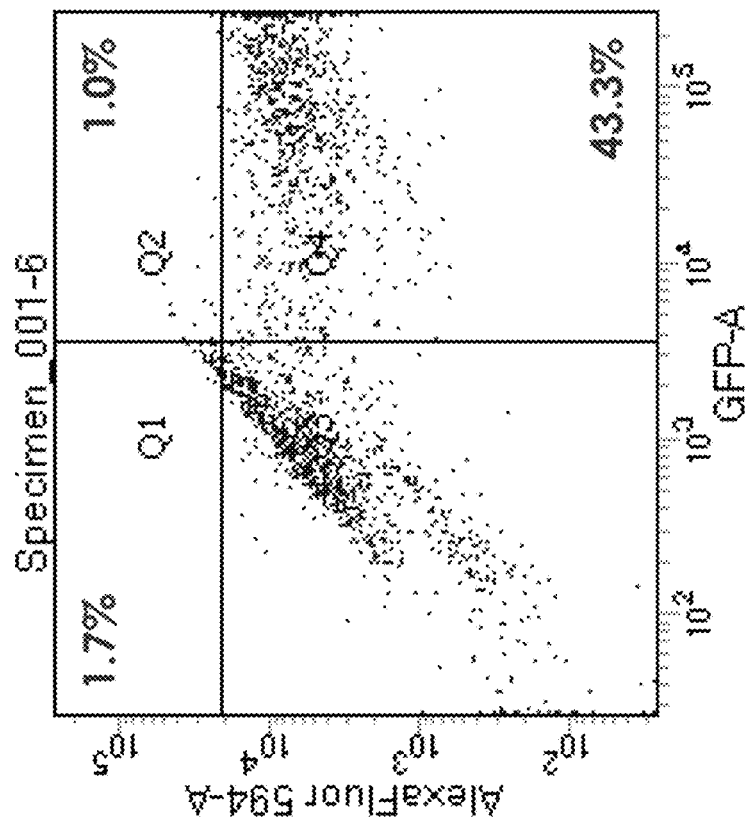
FIG. 5 demonstrates wild-type cells that were given GMT.
Figure 5:
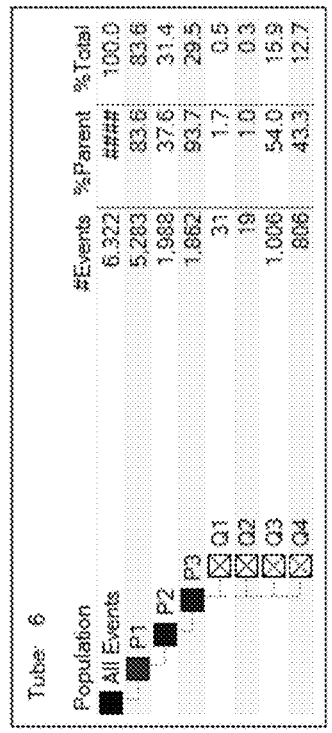
Figure 6:
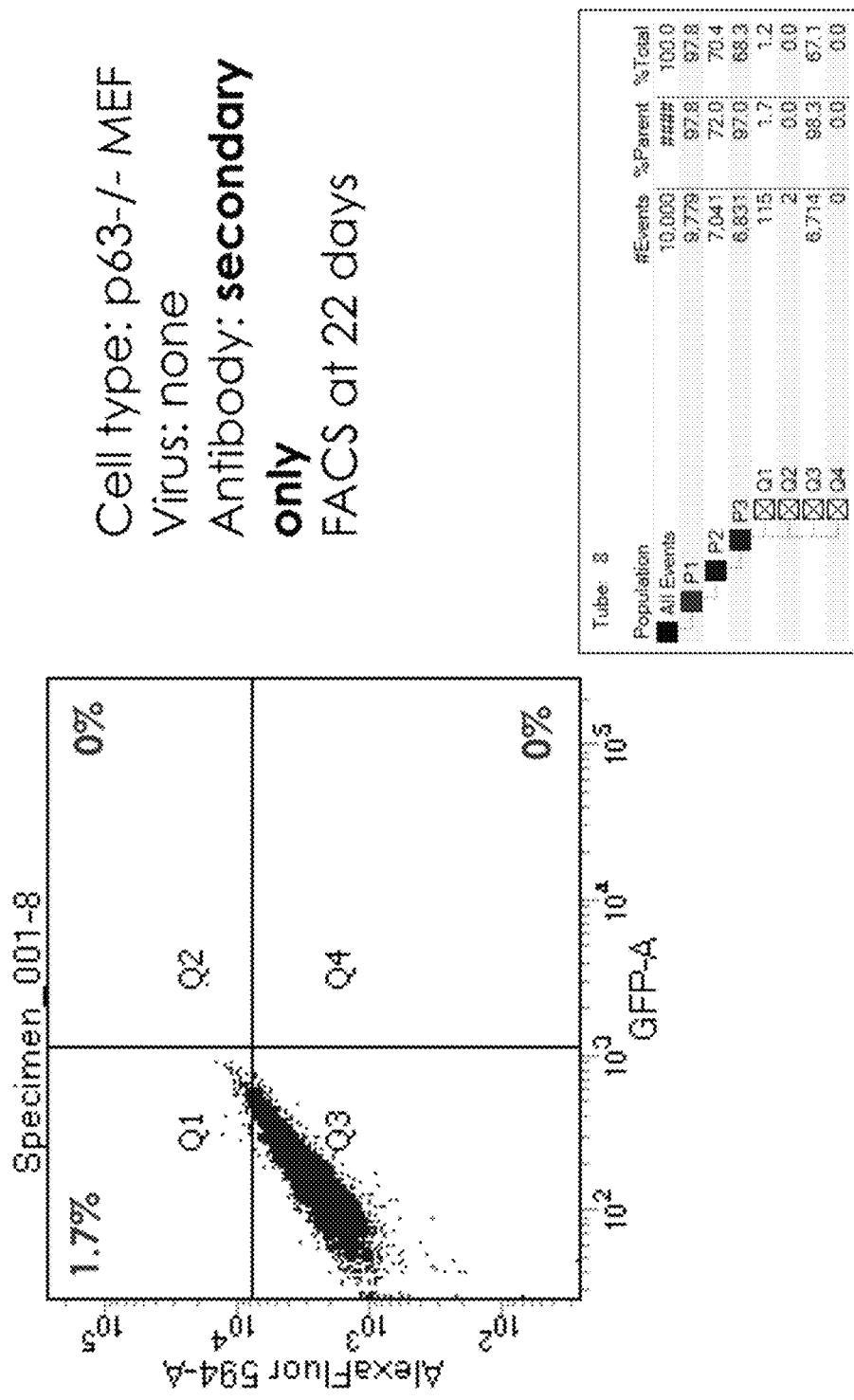
FIG. 6 shows a negative control for p63−/− mouse embryonic cells that were only stained with the secondary antibody. This was one of the controls used to set the gate for FACS analysis.
Figure 7:
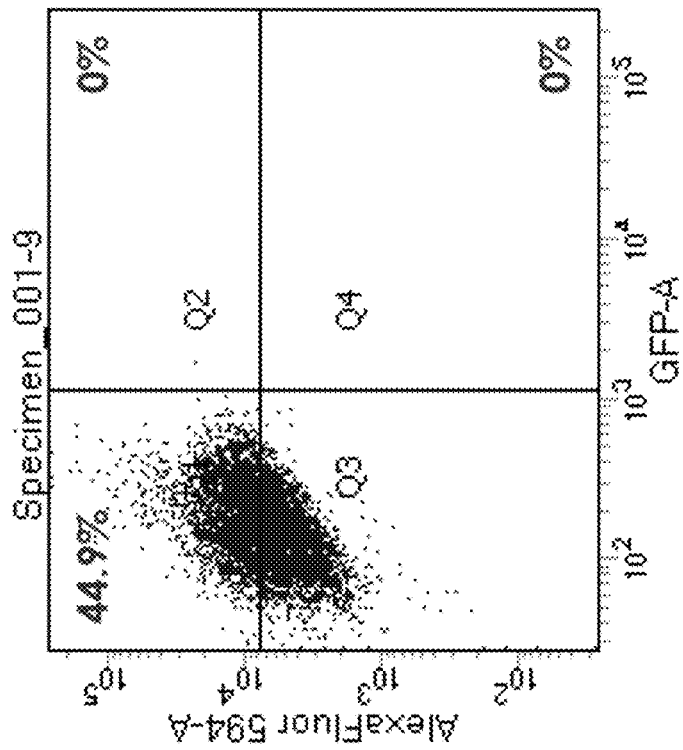
FIG. 7 demonstrates p63−/− cells that were stained with both the primary and secondary antibodies.
Figure 7:
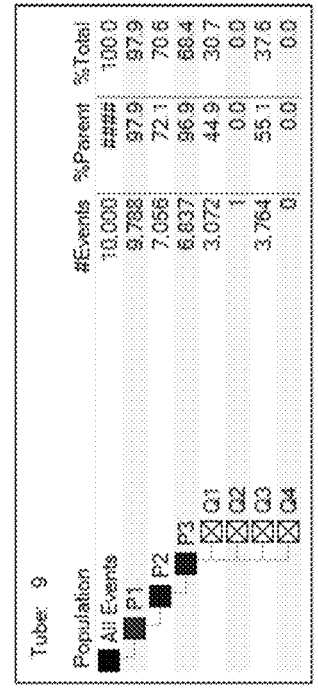
Figure 8:
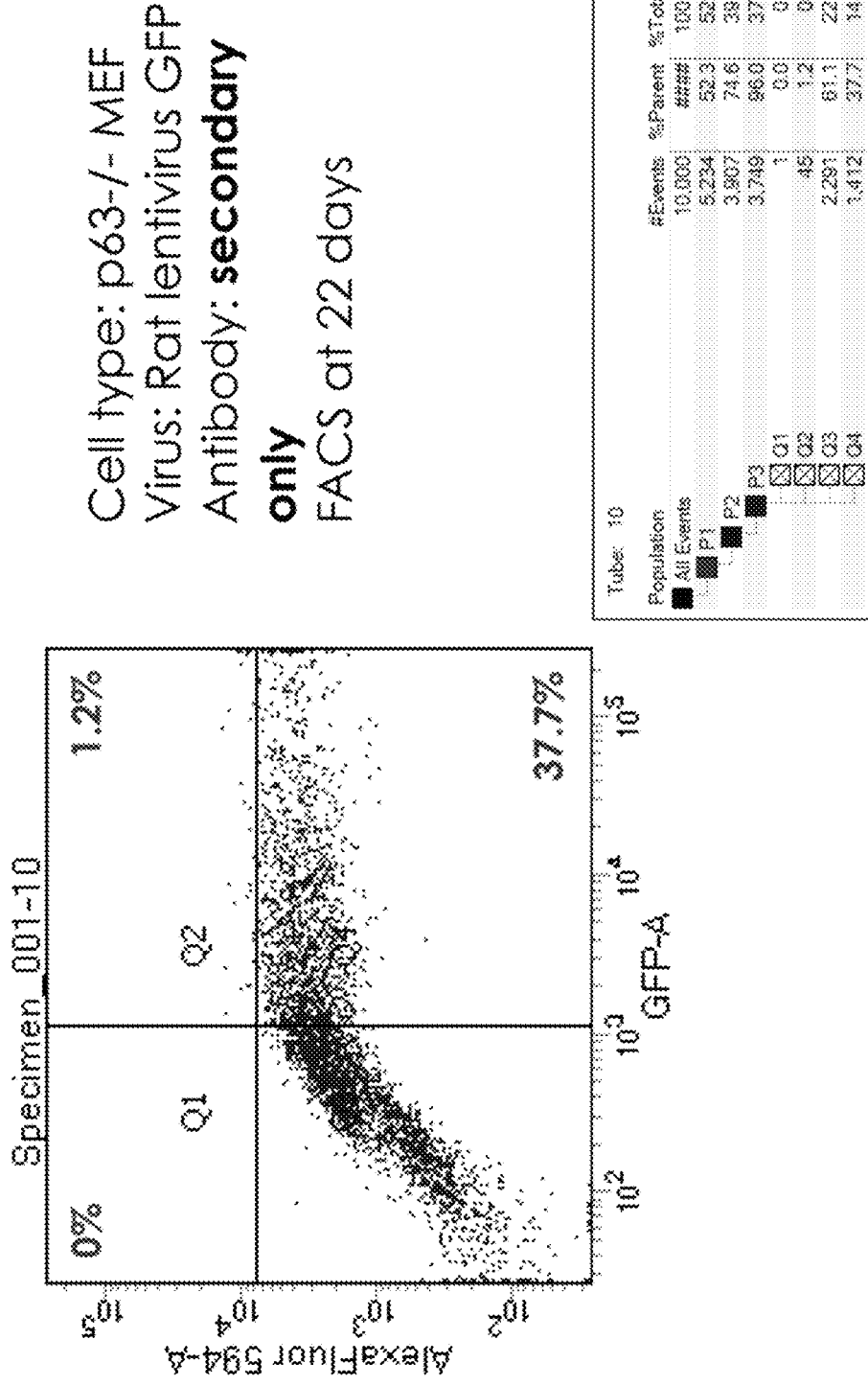
FIG. 8 demonstrates p63−/− cells that were given GFP and stained with only the secondary antibody. This was one of the controls used to set the gate for FACS analysis.
Figure 9:
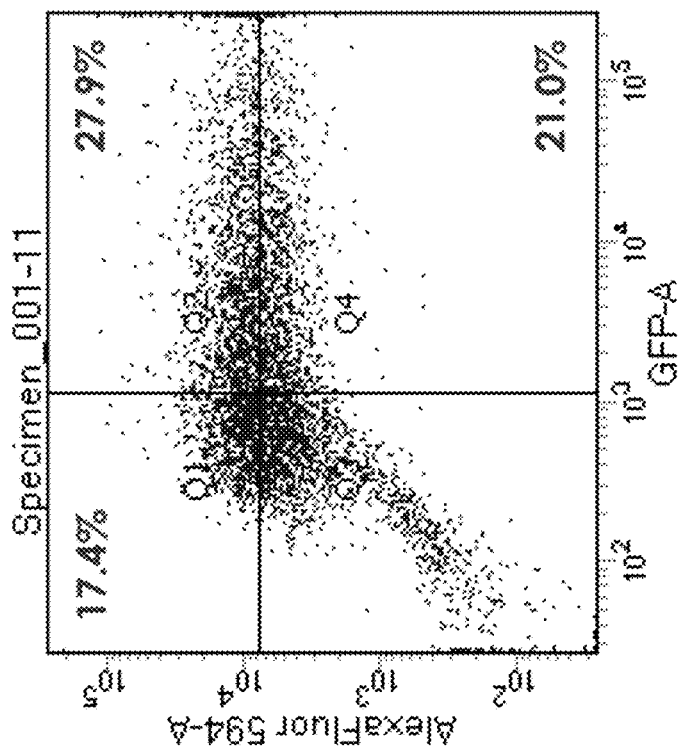
FIG. 9 shows p63−/− cells that were given GFP and stained with both the primary and secondary antibodies.
Figure 10:
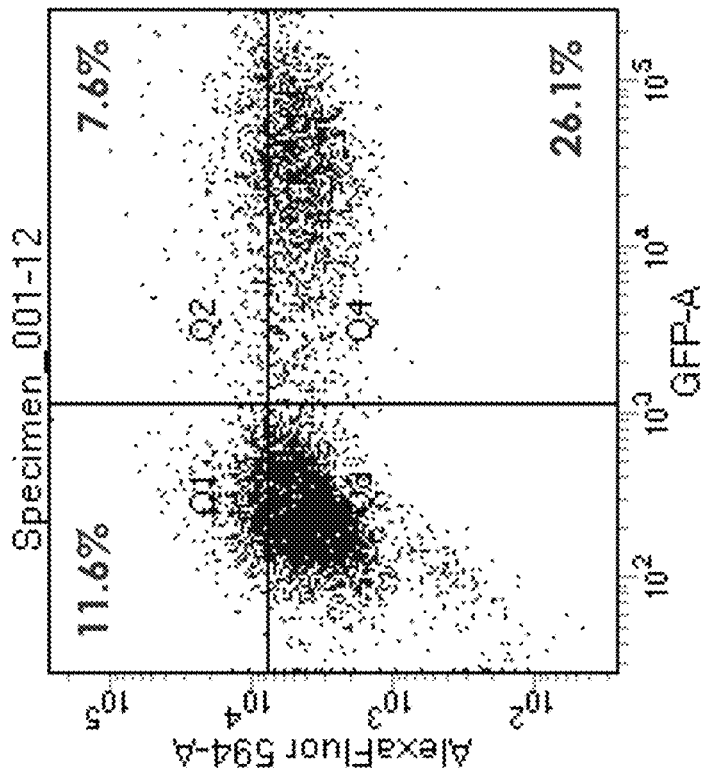
FIG. 10 shows FACS results for p63−/− cells given GMT.
Figure 10:
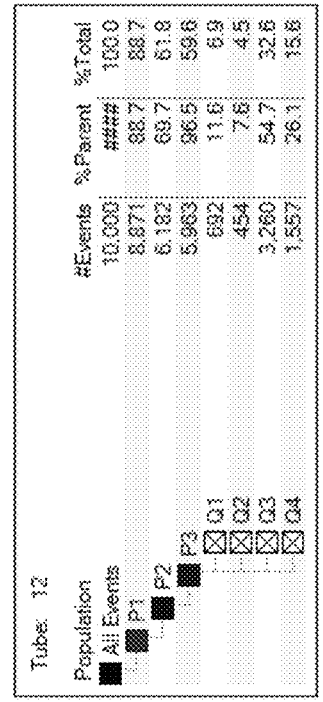
Figure 11:
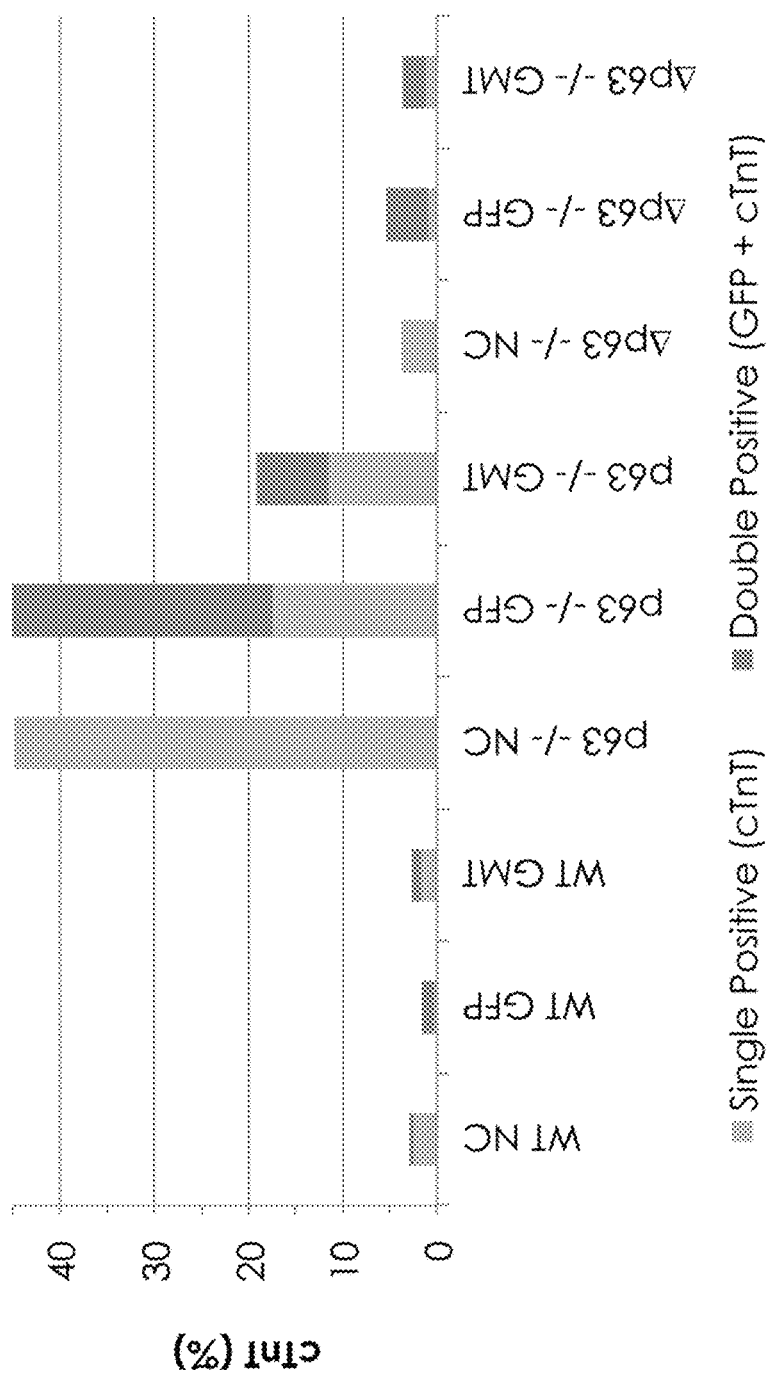
FIG. 11 illustrates all results as a function of cTnT expression, which is a marker of cardiomyocyte lineage.

FIG. 1 shows experimental design for analyzing fibroblast transdifferentiation into cardiomyocytes in vitro. GMT refers to the combination of Gata4, Mef2c, and Tbx5. GFP refer to green fluorescence protein. FIG. 2 shows FACS analysis of a positive control comprising neonatal rat cardiomyoblasts. FIG. 3 demonstrates a negative control using wild-type cells given no virus, and in FIG. 4 the wild-type cells are exposed to GFP whereas in FIG. 5 the wild-type cells were given GMT. FIG. 6 shows a negative control (secondary antibody only) for p63−/−mouse embryonic cells showing 1.7% cTNT as noise. In FIG. 7, the p63−/−cells were given no virus, whereas in FIG. 8 the p63−/−cells were given GFP and stained with only the negative control secondary antibody and in FIG. 9 the p63−/−cells were given GFP. FIG. 10 shows FACS results for p63−/−cells given GMT and both antibodies. FIG. 11 illustrates all results as a function of cTnT expression.

Thus, untreated p63−/−MEF's expressed cTnT 45% of the time while wild-type MEF's expressed cTnT 3% of the time. Untreated p63−/−MEF's display a 15 fold increase in the expression of cTnT compared to wild-type MEF's. Therefore, cells deficient in p63 are able to reprogram into cardiomyocyte-like cells at a highly efficient rate, suggesting that it is feasible to efficiently reprogram endogenous cardiac fibroblasts from infarcted or disease myocardium into cardiomyocytes.

Example 2

Figure 12:
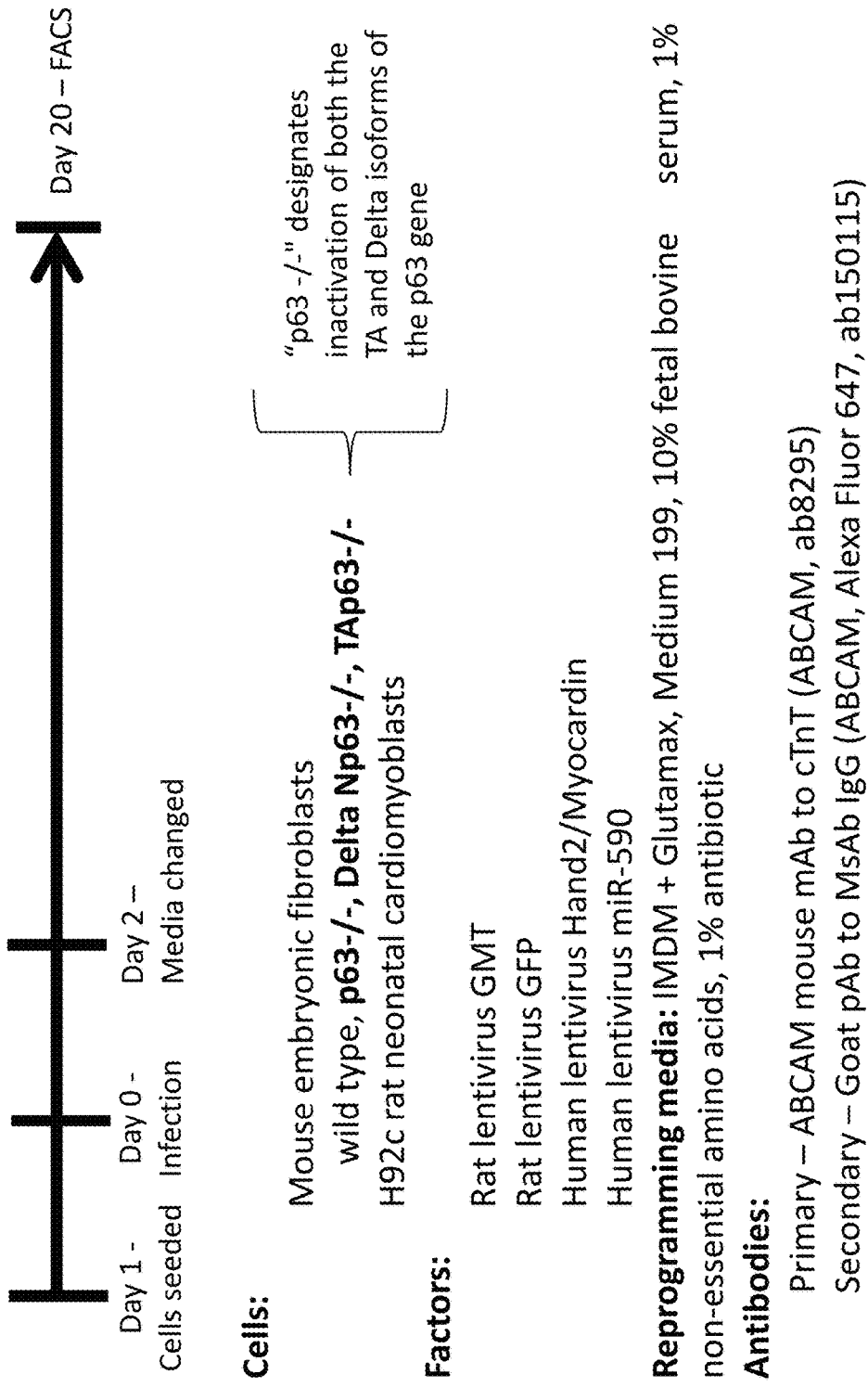
FIG. 12 illustrates an example of an experimental design for analyzing transdifferentiation of fibroblasts into cardiomyocytes in vitro. Specifically, the inventors analyzed the role of the two isoforms of the p63 gene. "p63−/−" indicates MEFs that have had the both isoforms of the p63 gene deleted. Reprogramming efficiency was measured with Flow Cytometry for cardiac troponin T (cTnT) expression.
Figure 13:
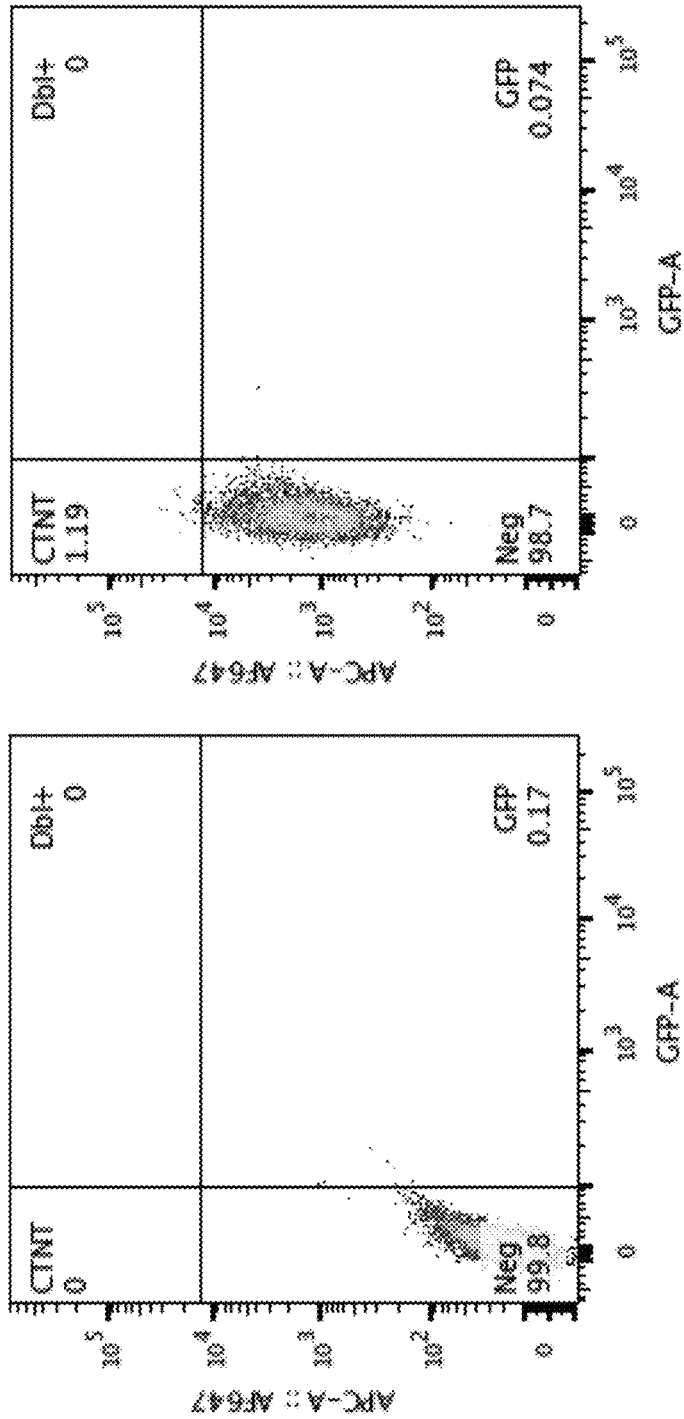
FIG. 13 shows FACS data for unstained and stained wild-type mouse embryonic fibroblasts (negative controls).
Figure 14:
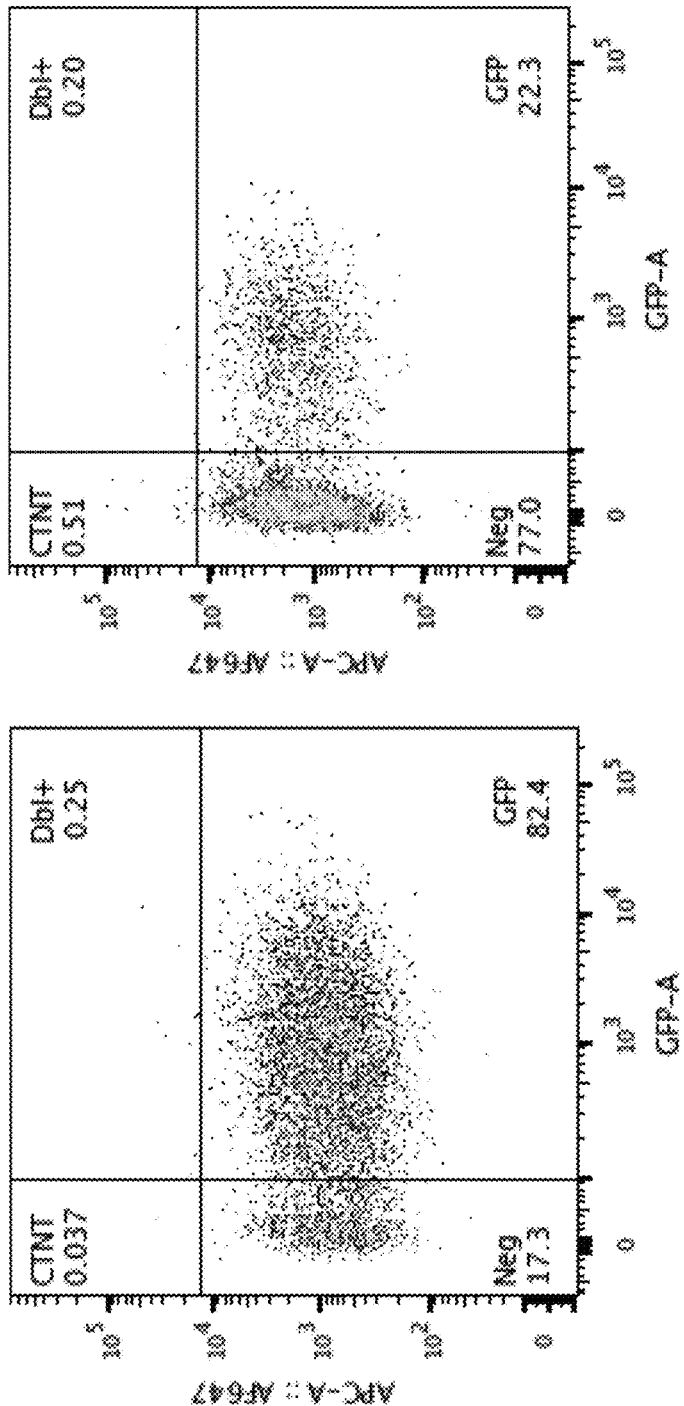
FIG. 14 shows wild type MEFs treated with lentiviral GFP and lentiviral GMT.
Figure 15:
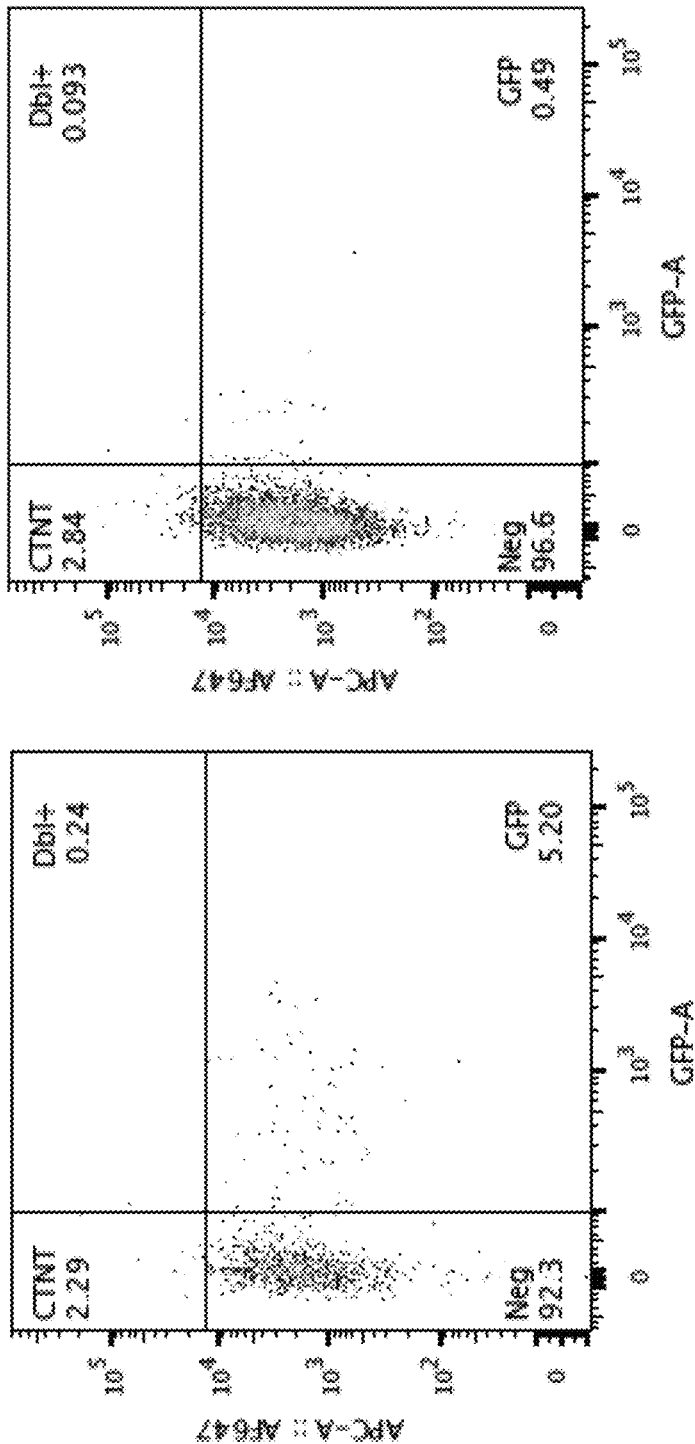
FIG. 15 shows wild-type MEFs that were given certain cardiac cell reprogramming factors, lentiviral Hand2 & Myocardin with or without lentiviral miR-590.
Figure 16:
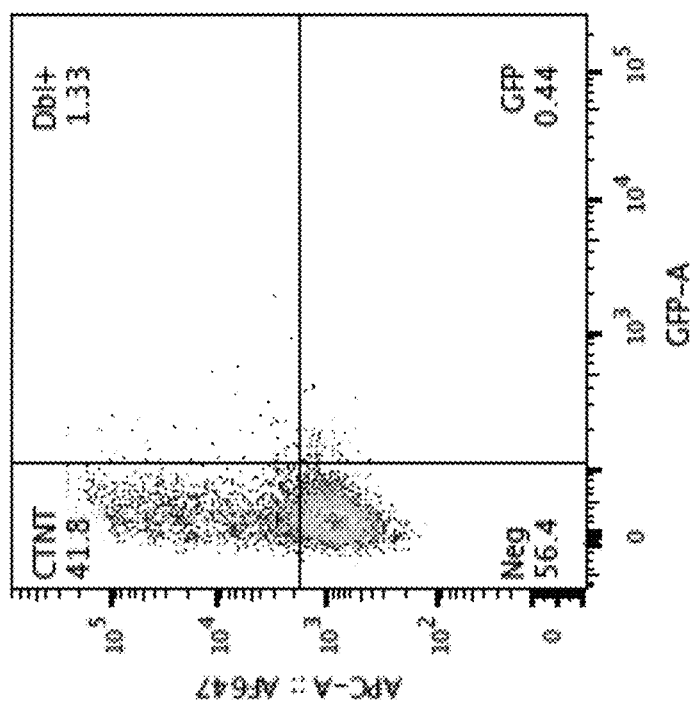
FIG. 16 demonstrates FACS analysis for the positive control h9c2 neonatal rat cardiomyoblasts.
Figure 17:
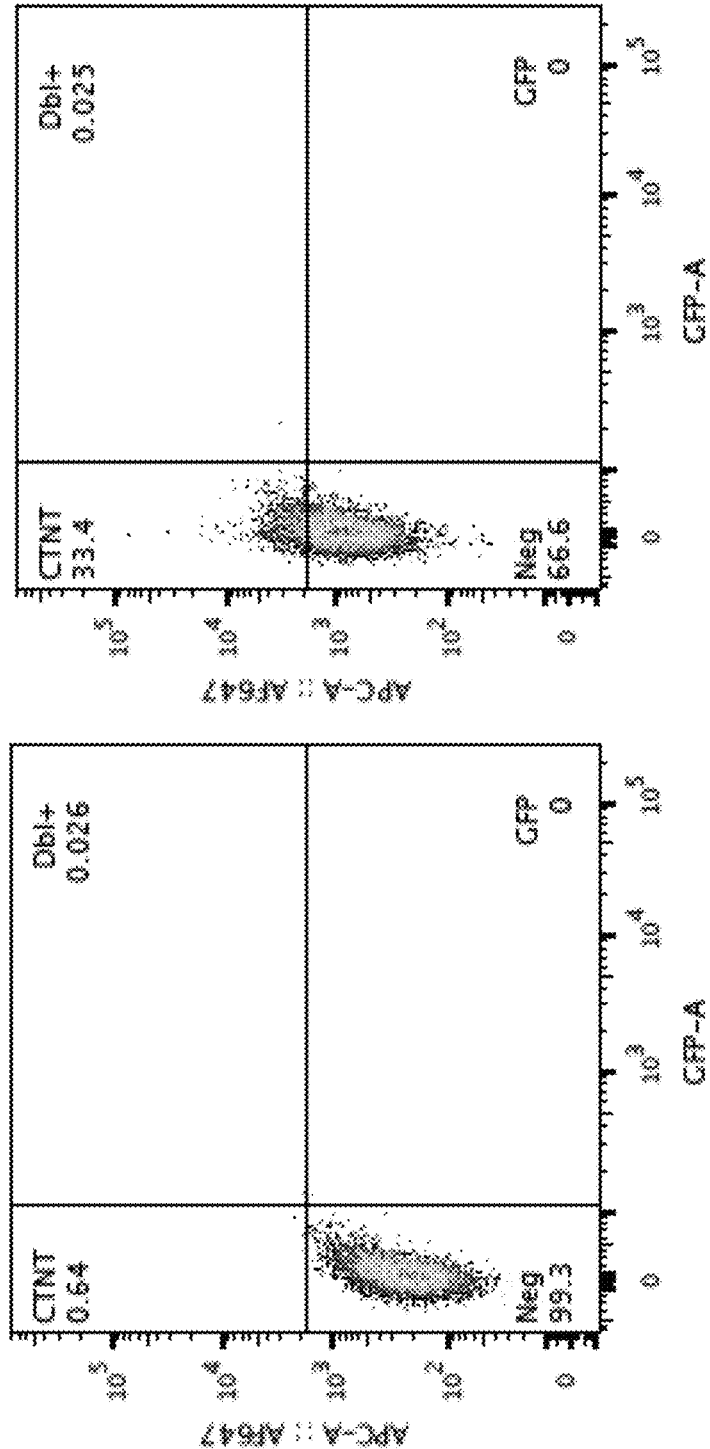
FIG. 17 shows results for the "p63−/− MEFs" that concerns the inactivation of both the TA and Delta isoforms of the p63 gene. These cells were not treated with reprogramming factors. The left side shows the p63−/− cells stained with only the secondary antibody, which was used to set the gate for FACS analysis. The right shows the p63−/− cells stained with both antibodies.
Figure 18:
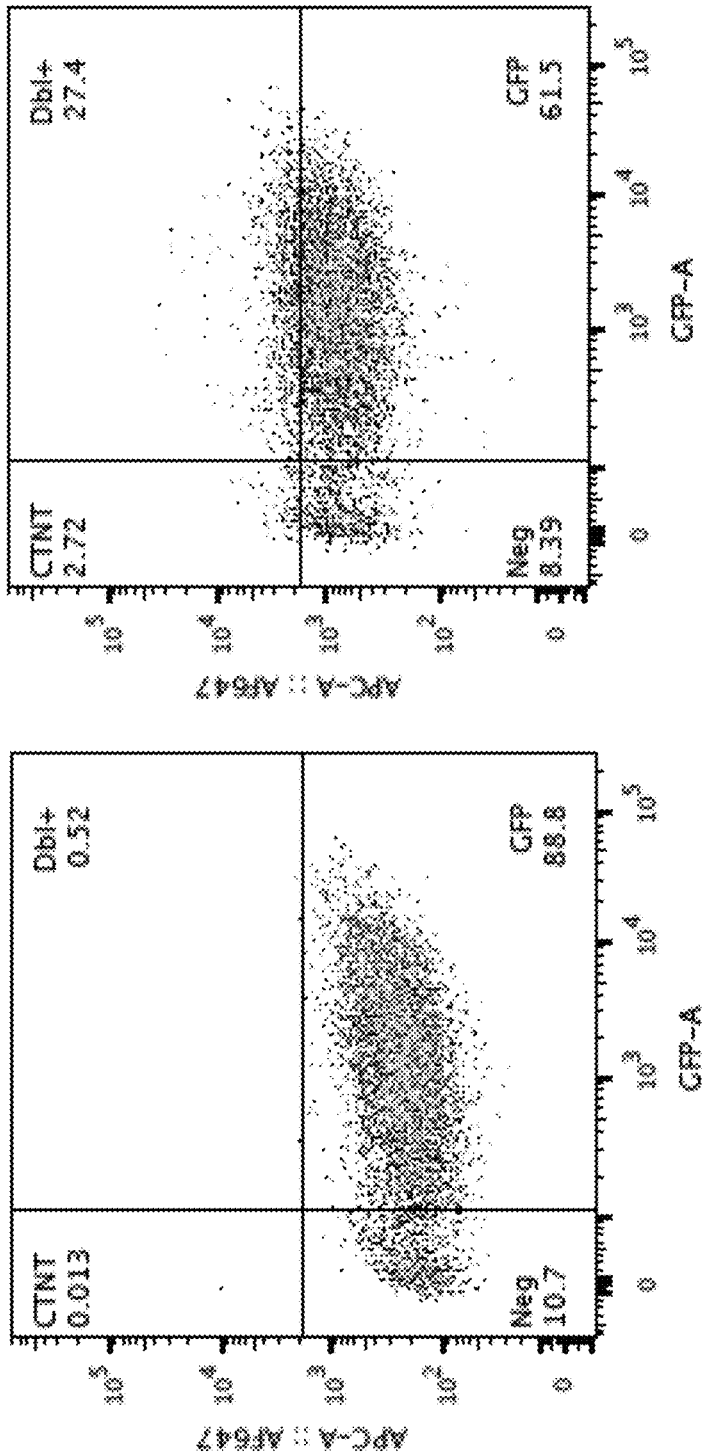
FIG. 18 demonstrates p63−/− MEFs exposed to GFP. The left shows staining with only the secondary antibody, which was used to set the gate for FACS analysis; while the right shows staining with both antibodies.
Figure 19:
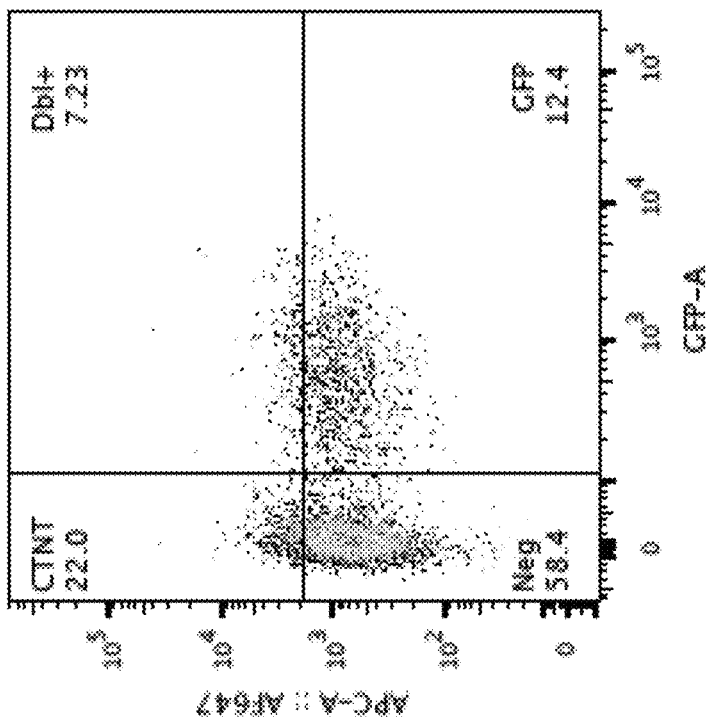
FIG. 19 shows results of the double KO p63−/− MEFs that were given lentiviral GMT factors.

P63 Inactivation and Addition of Hand2, Myocardin Increases Formation of CTNT+ Cells from Murine Embryonic Fibroblasts FIG. 12 illustrates an experimental design for analyzing transdifferentiation of fibroblasts into cardiomyocytes in vitro. FIG. 13 shows FACS data for unstained and stained wild-type MEFs (negative controls). FIG. 14 shows wild type MEFs treated with lentiviral GFP and lentiviral GMT. In FIG. 15, wild-type MEFs were given the noted factors (lentiviral Hand2 & Myocardin) and exposed to both antibodies. In FIG. 16, shows a positive control, h9c2 neonatal rat cardiomyoblasts. FIG. 17 shows the p63−/− (which concerns the inactivation of both the TA and Delta isoforms of the p63 gene) MEFs where no factors were provided. The left side shows the control stained with only the secondary antibody while the right shows cells stained with both antibodies. FIG. 18 demonstrates the double KO p63−/−MEFs where GFP (left side shows staining only with secondary as a control while the right side shows staining with both antibodies). In FIG. 19, the double KO p63−/− MEFs were given lentiviral GMT factors and both primary and secondary antibodies.

Figure 20:
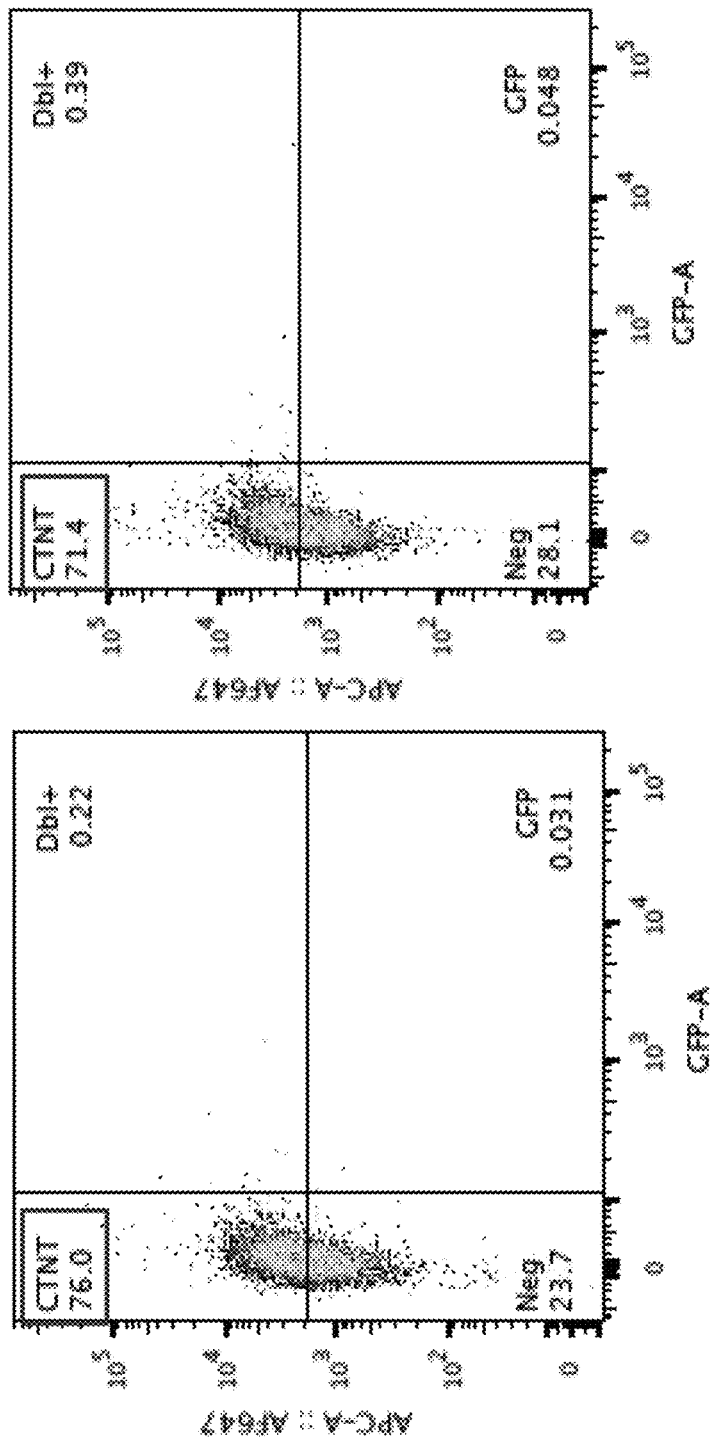
FIG. 20 demonstrates double KO p63−/− MEFs exposed to lentiviral Hand2 and myocardin, in the presence or absence of miR-590.
Figure 21:
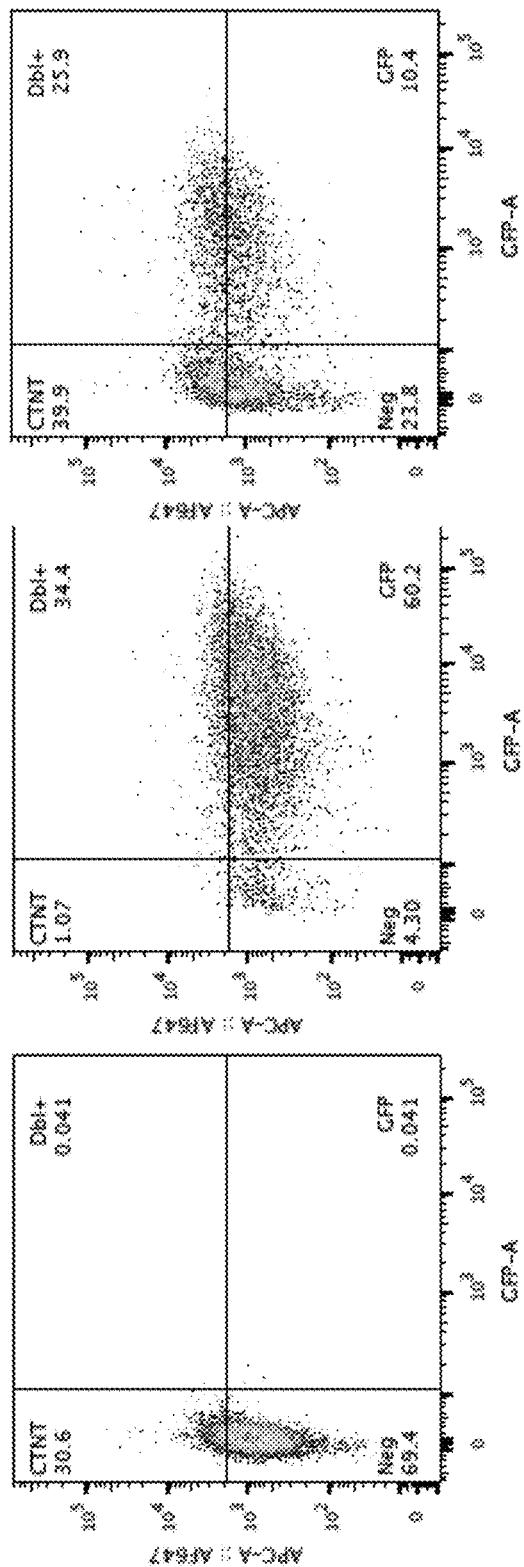
FIG. 21 illustrates delta Np63−/− MEFs (knockout of only one isoform) either with no factor, GFP, or GMT.
Figure 22:
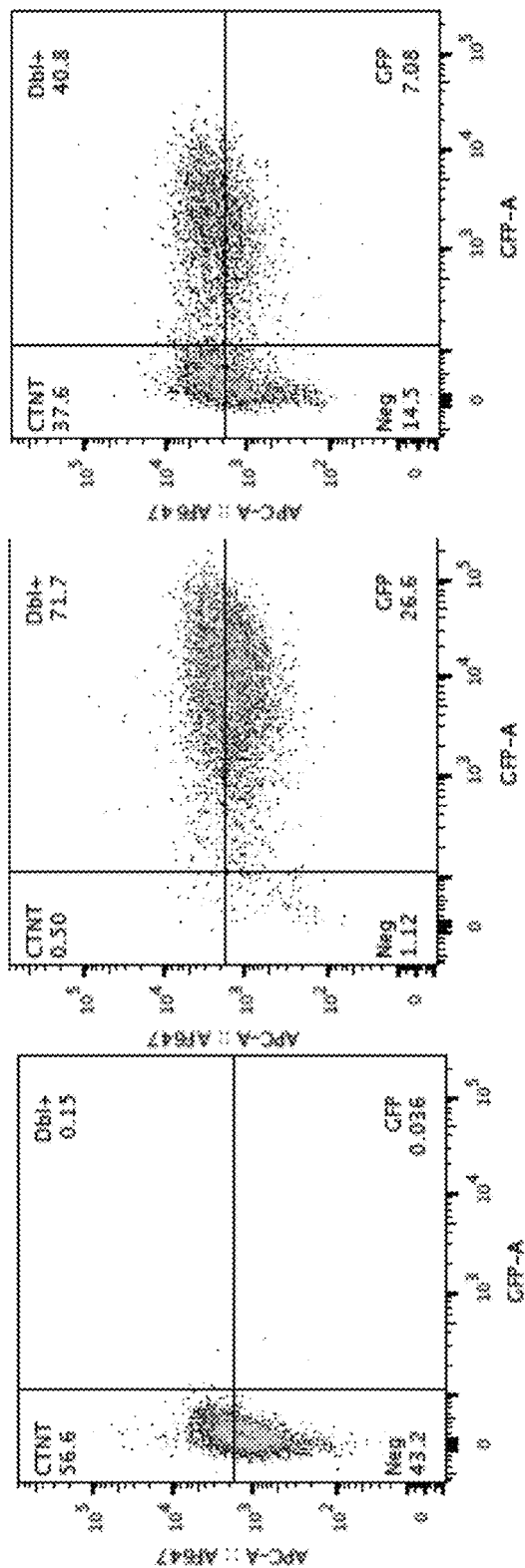
FIG. 22 shows TAp63−/− MEFs (knockout of only the other isoform) that were exposed to either no factor, GFP, or GMT.
Figure 23:
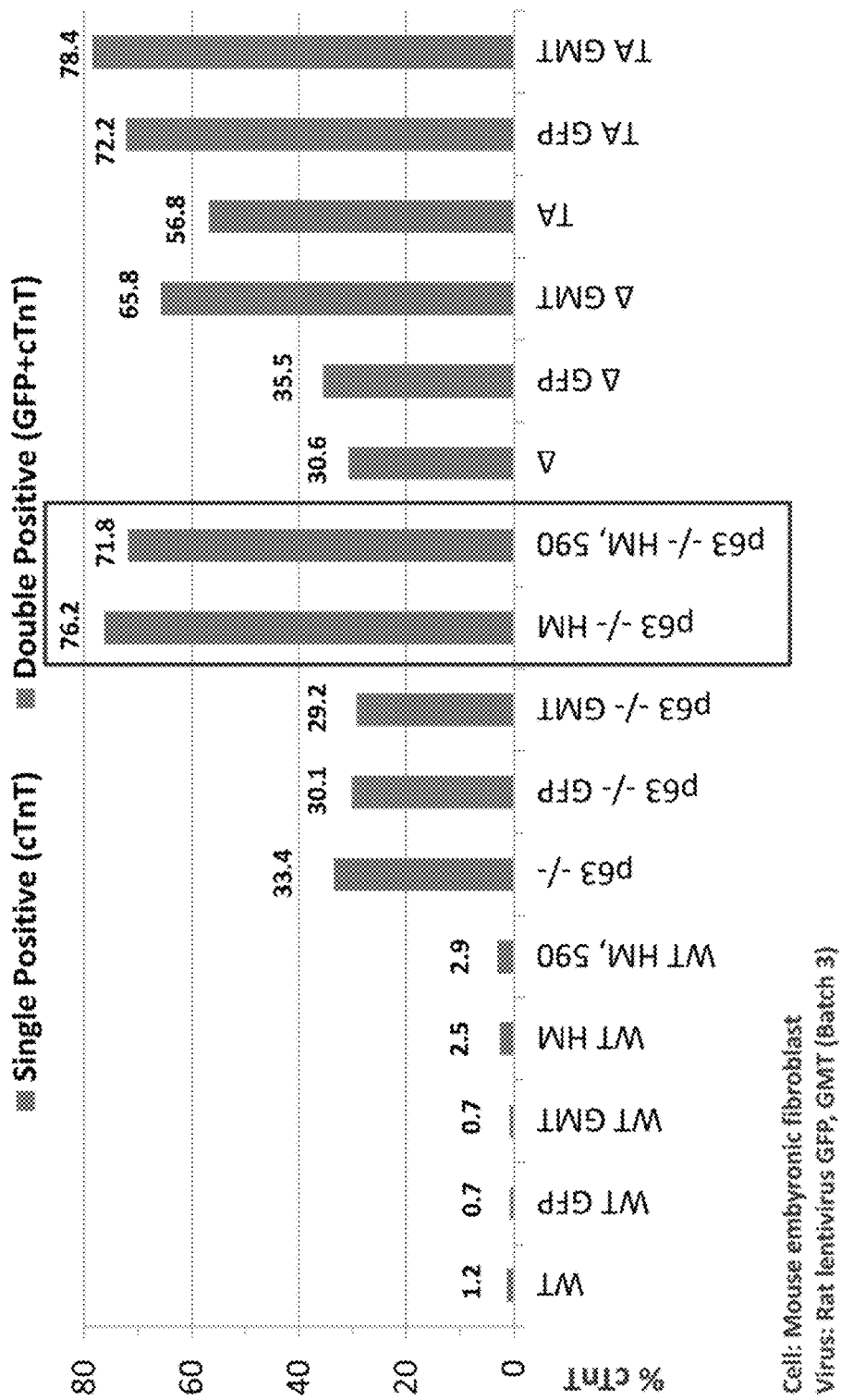
FIG. 23 summarizes the study, illustrating the percentage of cells expressing cTnT as a marker for cardiomyocyte lineage.
Figure 24:
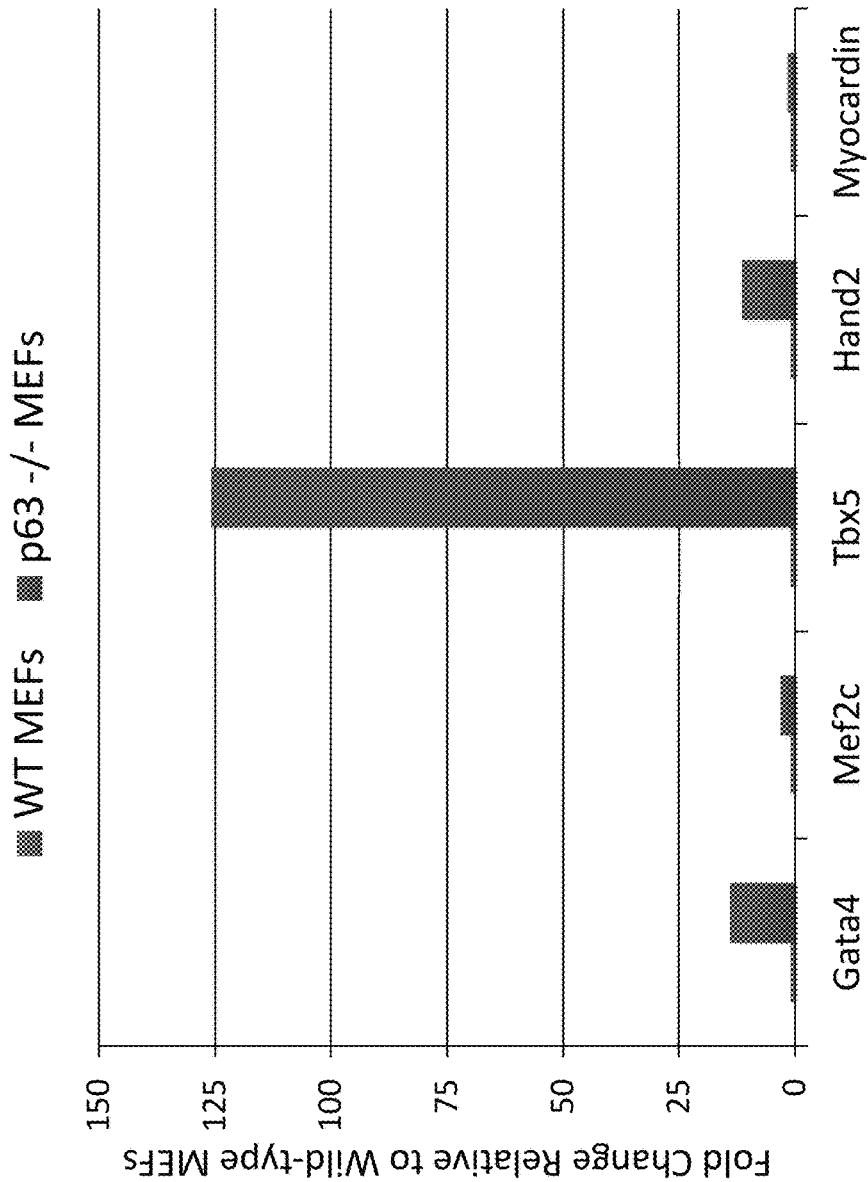
FIG. 24 demonstrates the expression of certain pro-cardiogenic factors as measured by qPCR of p63 knockout MEFs (H/M=human Hand2/Myocardin lentivirus (SystemsBio)

Next, the factors Hand2 (related to cardiac morphogenesis, formation of ventricles, aortic arch) and myocardin (smooth muscle differentiation; cardiac muscle specific activator of Serum Response Factor (which regulates cell cycle, growth, and differentiation)) were utilized with the cells. In FIG. 20, p63−/−MEFs were exposed to lentiviral Hand2 and myocardin in the presence or absence of miR-590. FIG. 21 illustrates delta Np63−/− MEFs (knockout of only the DeltaN isoform) either with no factor, GFP, or GMT in the presence of both primary and secondary antibodies. For FIG. 22, TAp63−/− MEFs (knockout of only the TA isoform) were exposed to either no factor, GFP, or GMT in the presence of both primary and secondary antibodies. FIG. 23 summarizes an experiment, illustrating the percentage of cells expressing cTnT as a marker for cardiomyocyte lineage. FIG. 24 demonstrates the expression of certain pro-cardiogenic factors as measured by qPCR of p63 knockout MEFs (H/M=human Hand2/Myocardin lentivirus (SystemsBio).

Furthermore, given the targets that the inventors have identified, it is feasible to use a viral vector, mRNA delivery, nanoparticle delivery system, etc., in order to create the desired effects. The example diagram (FIG. 25) provided shows a lentiviral vector with p63 shRNA and transcription factors Hand2 and Myocardin. Other similar approaches would involve an adenoviral vector or the use of modified mRNA for Hand2 and Myocardin combined with p63 siRNA oligonucleotides. Other methods of silencing p63 would involve the use of small molecule inhibitors or shRNA targeting other downstream regulatory genes. In summary, any of these approaches would allow for inactivation of the p63 gene with the addition of factors Hand2 and Myocardin, resulting in the desired effect.

Example 3

P63 Inactivation and the Addition of Several Other Factors May Further Enhance the Transdifferentiation of Fibroblasts into Cardiomyocytes Examples 1 and 2 illustrated two embodiments of applications of this disclosure. However, there are several other transcription factors that may be used to further enhance the efficiency: Gata4, Mef2c, Tbx5, miR-133, miR-1, Oct4, Klf4, c-myc, Sox2, Mesp1, Brachyury, Nkx2.5, ETS2, ESRRG, Mrtf-A, MyoD, ZFPM2 (in nucleic acid or polypeptide or peptide form, in specific embodiments). Adjunctive therapy could comprise ITD-1 (TGF beta inhibitor), VEGF, surgery (coronary artery bypass), PCI, or medial therapy, for example.

Example 4

Adjunct Therapy Comprising Downregulation of SNAI1

Figure 26:
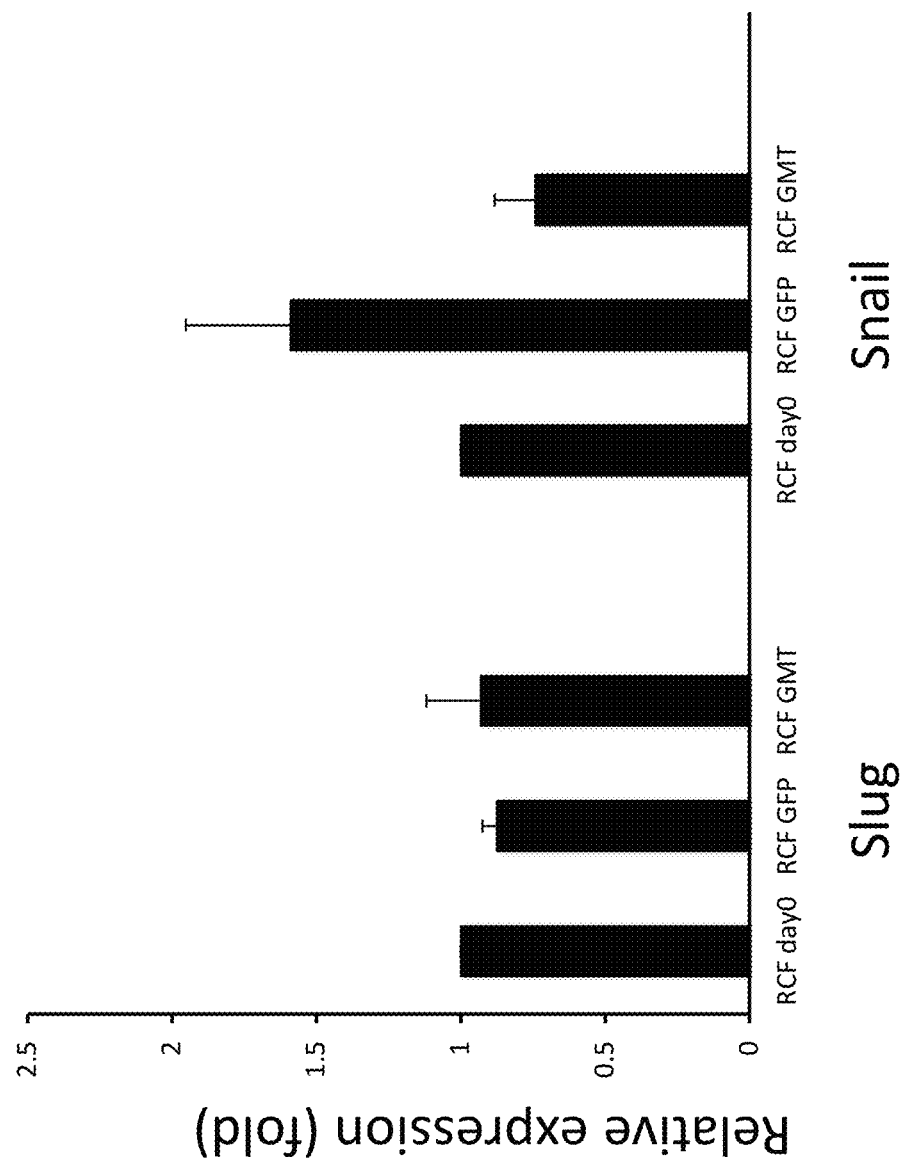
FIG. 26 shows downregulation of Snail expression in rat cardiac fibroblasts treated with GMT; qPCR analysis of Slug and Snail expression is shown. After 14 days treatment with human lentiviral GMT or GFP alone, rat cardiac fibroblasts were analyzed for levels of the mRNAs (n=2 biological replicates, each performed in triplicate). Data are shown as fold change relative to day 0. RCF: rat cardiac fibroblast. Error bars show SEM.

In specific embodiments adjuncts to p63, p53, and/or p21 inactivation comprise anti-fibrotic therapy, with or without the addition of cardiac cell reprogramming factors, chromatin destabilizing agents, and/or angiogenic therapy. FIG. 26 confirms that GMT-treated cells have lower Snail expression, which plays a role in fibrosis. Snail ("Snail") is a downstream effector of TGF-beta, which has been implicated in fibrosis or scar formation post-myocardial infarction. In specific embodiments, one can combine the reprogramming efficiency of p63, p53, and/or p21 inactivation with one or more anti-fibrotic agents, such as an anti-Snail agent (for example, siRNA, antibody, small molecule such as ITD-1, etc.) in order to regenerate at least part of the myocardium after a cardiac medical condition, such as a heart attack.

Example 5

P63 Knockdown in Mammalian Cells

Figure 28:
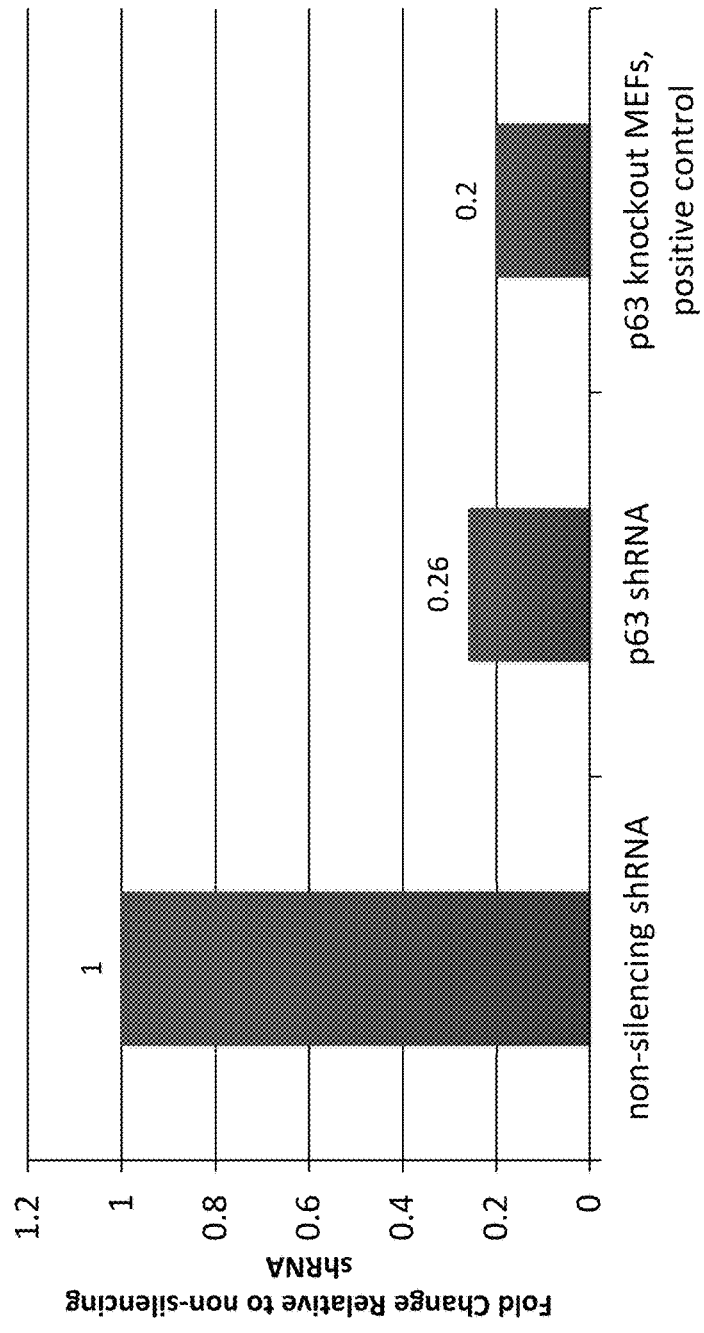
FIG. 28 demonstrates p63 shRNA knockdown efficiency in MEFs.
Figure 29:
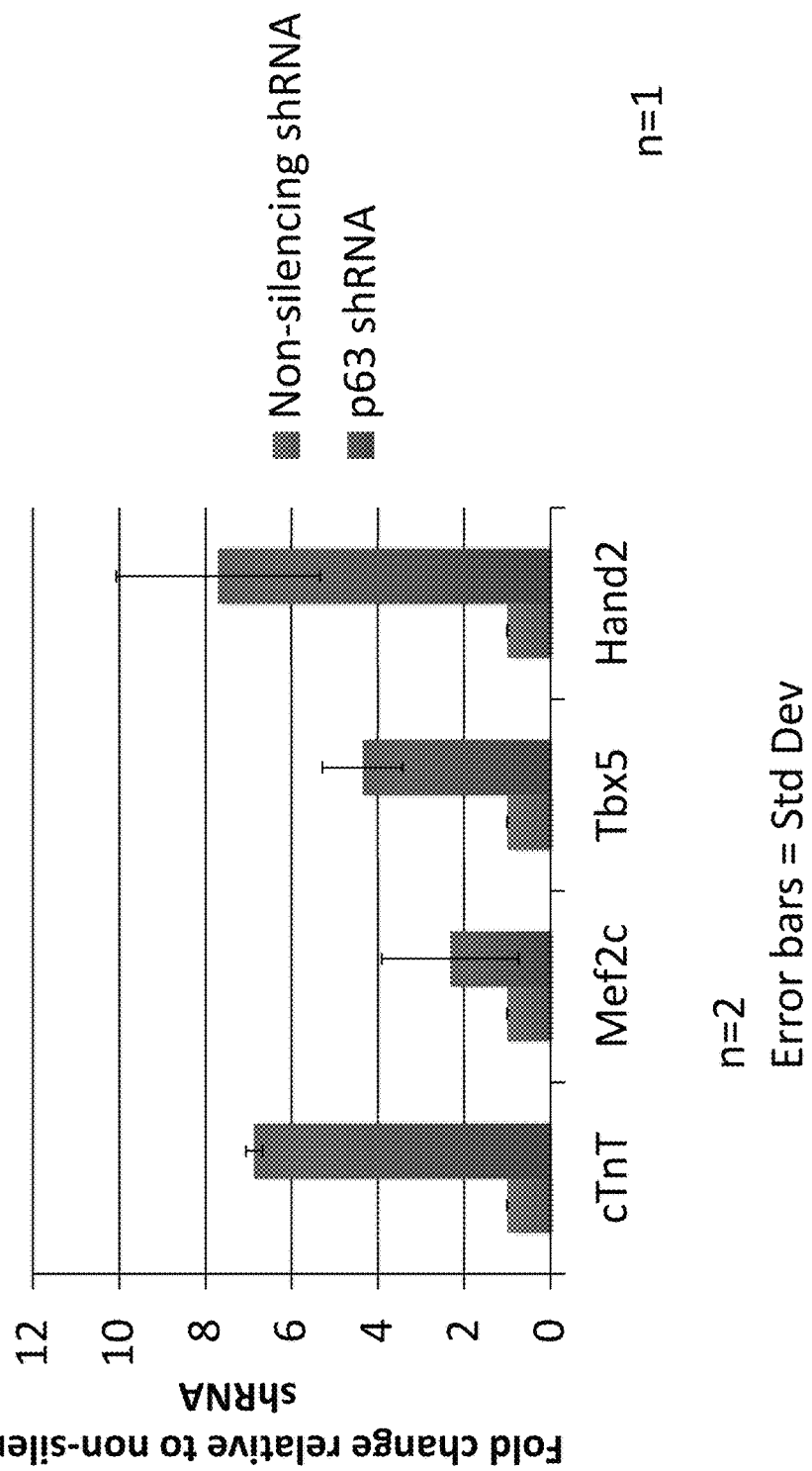
FIG. 29 demonstrates that p63 knockdown MEFs, i.e. those treated with shRNA, also express pro-cardiogenic factors Gata4, Mef2c, Tbx5, Hand2 and Myocardin (tested at three weeks).

FIG. 27 illustrates an example protocol of how p63 can be knocked down using shRNA in mouse embryonic fibroblasts (MEFs) in vitro. The efficiency of p63 knockdown in mouse embryonic fibroblasts (MEFs) is demonstrated in FIG. 28. In the figure, it is shown by qPCR the p63 knockdown efficiency in the MEFs using shRNA lentivirus as an example of a vector. Puromycin selection (1 ug/mL) was performed after infection, and knockdown efficiency was measured by quantitative PCR 5-7 days after selection. FIG. 28 demonstrates efficient knockdown of p63 using an exemplary p63 shRNA on a lentivirus vector. FIG. 29 demonstrates maintenance of p63 knockdown at 3 weeks. In particular, qPCR data was gathered at 3 weeks following infection of MEFs with p63 shRNA lentivirus. Outcome was measure as the fold change of knockdown relative to non-silencing shRNA. The data shows that silencing p63 with shRNA results in upregulation of cTnT and pro-cardiogenic factors Mef2c, Tbx5, Hand2 and Myocardin.

Figure 30:
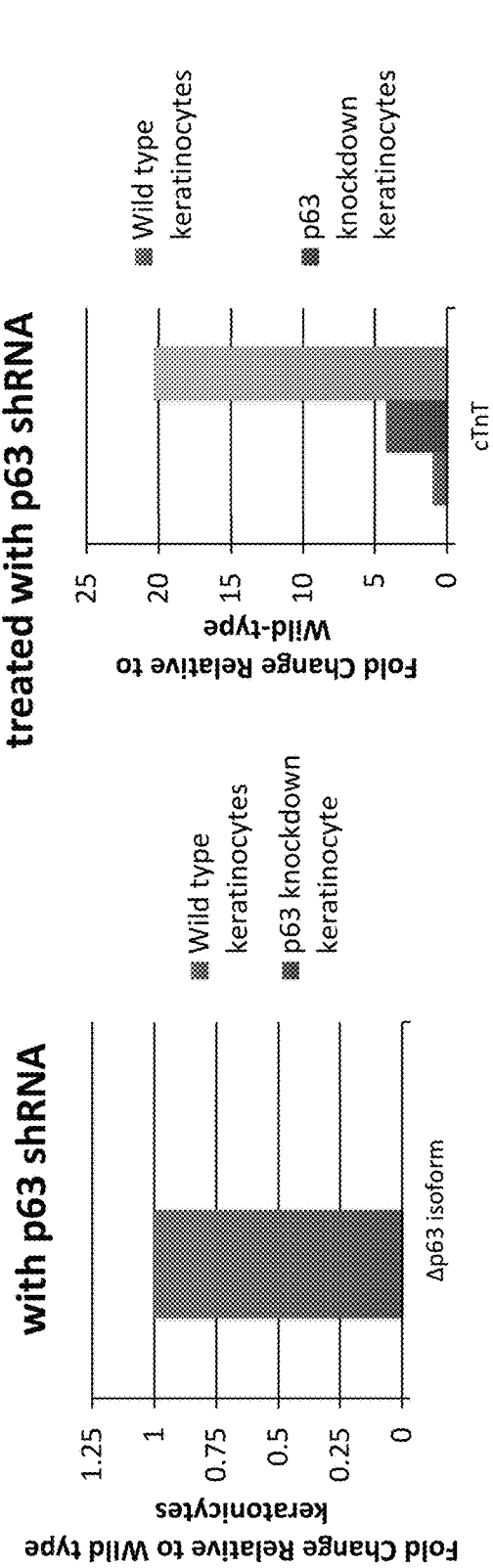
FIG. 30 demonstrates p63 knockdown efficiency in adult human keratinocytes. P63 knockdown also reults in upregulation of cTnt, which is further enhanced with Hand2, Myocardin.

FIG. 30 demonstrates that p63 knockdown is efficient in other types of cells than MEFs by demonstrating p63 knockdown in adult human keratinocytes, or skin cells. According to the left panel, using qPCR the p63 knockdown efficiency was determined in adult human keratinocytes treated with p63 shRNA. Thus, adult human keratinocytes may also be reprogrammed into cardiomyocyte-like cells using p63 knockdown with shRNA. The right panel in FIG. 30 shows by qPCR that there is increased cardiac troponin T expression in adult human keratinocytes treated with p63 shRNA. p63 knockdown alone results in a 5-fold higher expression of cTnT while p63 knockdown in addition to Hand2/Myocardin results in a 20-fold higher expression of cTnT. Therefore, FIG. 30 provides data that silencing p63 works in adult human cells.

Figure 31:
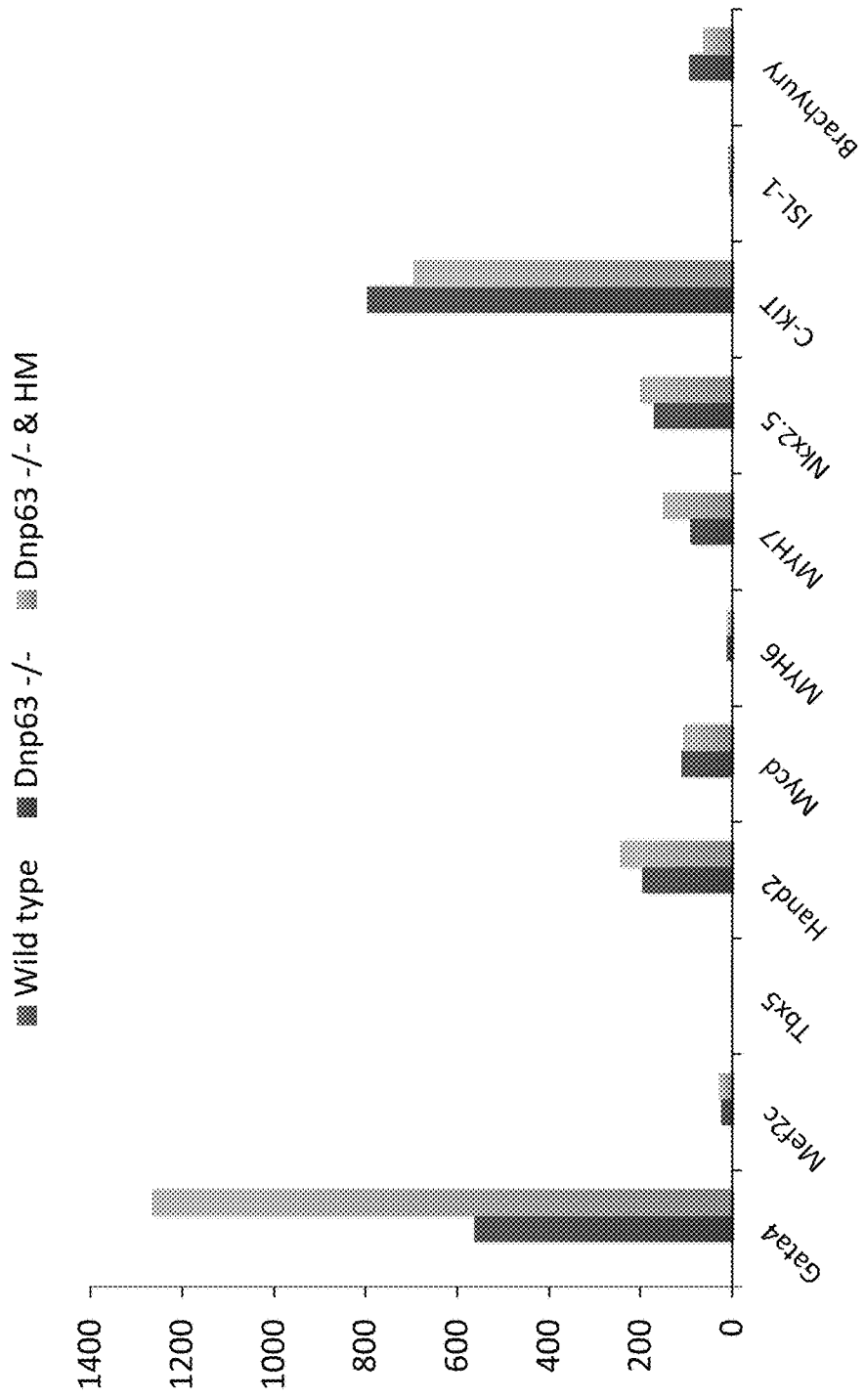
FIG. 31 shows that adult human keratinocytes treated with p63 shRNA lentivirus express pro-cardiogenic markers as well as cardiac structural markers Myosin Heavy Chain 6 (MYH6) and Myosin Heavy Chain 7 (MYH7).

FIG. 31 demonstrates by qPCR that there is increased expression of pro-cardiogenic factors and cardiac structural markers in adult human keratinocytes treated with p63 shRNA. In particular, p63 knockdown enhances reprogramming via induction of Gata4, Mef2c, Tbx5, Hand2 and Myocardin. This parallels findings with p63 knockout MEFs which also expressed these markers. p63 knockdown also leads to increased expression of cardiac structural markers MYH6, MYH7 and cardiac progenitor markers Nkx2.5, c-kit, Is1-1 and Brachyury.

In specific embodiments, one or more p63, p53, and/or p21 inactivation agents are provided to an individual in need thereof and the individual also receives one or more anti-fibrotic agents. In some cases the anti-fibrotic agent is provided to the individual before, during, and/or after the one or more anti-fibrotic agents. In cases wherein the individual also receives one or more cardiac cell reprogramming factors and/or one or more chromatin destabilizing agents, the one or more anti-fibrotic agent may be provided to the individual before, during, and/or after the respective factors or agents.

Although the present disclosure and its advantages have been described in detail, it should be understood that various changes, substitutions and alterations can be made herein without departing from the spirit and scope of the disclosure as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present disclosure, processes, machines, manufacture, compositions of matter, means, methods, or steps, presently existing or later to be developed that perform substantially the same function or achieve substantially the same result as the corresponding embodiments described herein may be utilized according to the present disclosure. Accordingly, the appended claims are intended to include within their scope such processes, machines, manufacture, compositions of matter, means, methods, or steps.

What is claimed is:

1. A composition for reprogramming differentiated cardiac cells to cardiomyocyte-like cells, the composition comprising one or more nucleic acid vectors, said vectors comprising one or more agents that inactivates p63 and comprising one or more cardiac cell reprogramming factors, wherein the cardiac cell reprogramming factors comprise Hand2 nucleic acids and myocardin nucleic acids.

2. The composition of claim 1, wherein the vector comprising one or more agents that inactivates p63 is the same vector that comprises one or more cardiac cell reprogramming factors.

3. The composition of claim 1, wherein the vector comprising one or more agents that inactivates p63 is a different vector than the vector that comprises one or more cardiac cell reprogramming factors.

4. The composition of claim 1, further comprising a vector that comprises one or more chromatin destabilizing agents.

5. The composition of claim 4, wherein the vector that comprises one or more agents that inactivates p63 is the same vector that comprises one or more chromatin destabilizing agents.

6. The composition of claim 4, wherein the vector that comprises one or more agents that inactivates p63 and that comprises one or more cardiac cell reprogramming factors is the same vector that comprises one or more chromatin destabilizing agents.

7. The composition of claim 4, wherein the vector that comprises one or more agents that inactivates p63 and that comprises one or more cardiac cell reprogramming factors is a different vector that comprises one or more chromatin destabilizing agents.

8. The composition of claim 1, wherein the composition comprises a vector that comprises p63 shRNA and one or both of Hand 2 and myocardin nucleic acids.

9. The composition of claim 1, wherein the composition comprises a vector that comprises p63 shRNA and Hand2 nucleic acids.

10. The composition of claim 1, wherein the composition comprises a vector that comprises p63 shRNA and myocardin nucleic acids.

11. The composition of claim 1, wherein the composition comprises a vector that comprises p63 shRNA, Hand2, and myocardin nucleic acids.

12. The composition of claim 1, comprising one or more anti-fibrotic agents.

13. A kit comprising the composition of claim 1, said composition housed in a suitable container.

14. An isolated cell comprising the composition of claim 1.

15. An isolated cell comprising the composition of claim 8.

16. The composition of claim 1, wherein the agent that inactivates p63 is p63 shRNA or siRNA or a functional equivalent thereof.

17. The composition of claim 16, wherein the agent that inactivates p63 is p63 shRNA or siRNA.

18. The composition of claim 1, wherein the cardiac cell reprogramming factors consists essentially of Hand2 nucleic acids and myocardin nucleic acids.

* * * * *